(12) United States Patent
Rubin et al.

(10) Patent No.: US 6,448,000 B1
(45) Date of Patent: Sep. 10, 2002

(54) MAMMALIAN GENES INVOLVED IN VIRAL INFECTION AND TUMOR SUPPRESSION

(75) Inventors: Donald H. Rubin; Edward L. Organ, both of Nashville; Raymond N. Dubois, Franklin, all of TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/171,209

(22) PCT Filed: Apr. 11, 1997

(86) PCT No.: PCT/US97/06067
§ 371 (c)(1),
(2), (4) Date: Mar. 8, 1999

(87) PCT Pub. No.: WO97/39119
PCT Pub. Date: Oct. 23, 1997

Related U.S. Application Data

(60) Provisional application No. 60/015,334, filed on Apr. 15, 1996.

(51) Int. Cl.$^7$ .................................................. C12Q 1/68
(52) U.S. Cl. ........................ 435/6; 435/440; 435/325; 435/252.3; 536/23.1; 536/23.5
(58) Field of Search ................................ 536/23.1, 23.5; 435/6, 325, 440, 252.3

(56) References Cited

U.S. PATENT DOCUMENTS

| | | | |
|---|---|---|---|
| 5,364,783 A | 11/1994 | Ruley et al. | 435/69.1 |
| 5,627,058 A | 5/1997 | Ruley et al. | 435/69.1 |

FOREIGN PATENT DOCUMENTS

| | | |
|---|---|---|
| WO | WO 90/09192 | 8/1990 |
| WO | WO 93/09230 | 5/1993 |
| WO | WO 97/39119 | 10/1997 |

OTHER PUBLICATIONS

Evans et al. "Gene Trapping and Functional Genomics" TIG, 13(9):370–374, Sep., 1997.

Organ et al. "U3 Gene–Trap Retrovirus Selection of Cellular Mutants Resistant to Lytic Reovirus Infection" J. Invest. Med., 44(3):320A, Annual Meeting of the Association of American Physicians, May 3–6, 1996.

Skarnes, W.C. "The Identification of New Genes: Gene Trapping in Transgenic Mice" Current Opinion in Biotechnology 4:684–689, Jan. 1, 1993.

Watson, JD, M Gilman, J Witkowski and M Zoller 1992 "The Isolation of Cloned Genes", in *Recombinant DNA*, 2$^{nd}$ Ed., WH Freeman &Co., New York.

Dermody, TS, ML Nibert, JD Wetzel, X Tong and BN Fields 1993 Cells and Viruses with Mutations Affecting Viral Entry Are Selected during Persistent Infections of L Cells with Mammalian Reoviruses. *J Virol* 67:2055–2063.

Pérez, L and L Carrasco 1994 Involvement of the vacuolar $H^+$–ATPase in animal virus entry. *J Gen Virol* 75:2595–2606.

Wright, JF, A Kurosky, and S Wasi 1994 An endothelial cell–surface form of annexin II binds human cytomegalovirus. *Biochem. Biophys. Res. Comm.* 198:983–989.

Brunetti, CR, RL Burke, S Kornfeld, W Gregory, FR Masiarz, KS Dingwell, and DC Johnson 1994 Herpes simplex virus glycoprotein D acquires mannose 6–phosphate residues and binds to mannose 6–phosphate receptors. *J Biol Chem* 269:17067–17074.

Wright, JF, A Kurosky, ELG Pryzdial, and S Wasi 1995 Host cellular annexin II is associated with cytomegalovirus particles isolated from cultured human fibroblasts *J. Virol* 69:4784–4791.

Brunetti, CR, RL Burke, B Hoflack, T Ludwig, KS Dingwell, and DC Johnson 1995 Role of mannose–6–phosphate receptors in herpes simplex virus entry into cells and cell–to–cell transmission. *J Virol* 69: 3517–3528.

*Primary Examiner*—James Martinell
(74) *Attorney, Agent, or Firm*—Needle & Rosenberg, PC

(57) ABSTRACT

The present invention provides methods of identifying cellular genes necessary for viral growth and cellular genes that function as tumor suppressors. Thus, the present invention provides nucleic acids related to and methods of reducing or preventing viral infection or cancer. The invention also provides methods of producing substantially virus-free cell cultures and methods for screening for additional such genes.

13 Claims, No Drawings

MAMMALIAN GENES INVOLVED IN VIRAL INFECTION AND TUMOR SUPPRESSION

This application is a 371 of PCT/US97/06067 filed Apr. 15, 1996 is Provisional application Ser. No. 60/015,334 filed Apr. 15, 1996.

This invention was made with partial government support under National Institutes of Health Grant No. CA68283 and a grant from the Department of Veterans Affairs. The United States Government has certain rights in the invention.

BACKGROUND

1. Field of the Invention

The present invention provides methods of identifying cellular genes used for viral growth or for tumor progression. Thus, the present invention relates to nucleic acids related to and methods of reducing or preventing viral infection and for suppressing tumor progression. The invention also relates to methods for screening for additional such genes.

2. Background Art

Various projects have been directed toward isolating and sequencing the genome of various animals, notably the human. However, most methodologies provide nucleotide sequences for which no function is linked or even suggested, thus limiting the immediate usefulness of such data.

The present invention, in contrast, provides methods of screening only for nucleic acids that are involved in a specific process, i.e., viral infection or tumor progression, and further, for nucleic acids useful in treatments for these processes because by this method only nucleic acids which are also nonessential to the cell are isolated. Such methods are highly useful, since they ascribe a function to each isolated gene, and thus the isolated nucleic acids can immediately be utilized in various specific methods and procedures.

For, example, the present invention provides methods of isolating nucleic acids encoding gene products used for viral infection, but nonessential to the cell. Viral infections of the intestine and liver are significant causes of human morbidity and mortality. Understanding the molecular mechanisms of such infections will lead to new approaches in their treatment and control.

Viruses can establish a variety of types of infection. These infections can be generally classified as lytic or persistent, though some lytic infections are considered persistent. Generally, persistent infections fall into two categories: (1) chronic (productive) infection, i.e., infection wherein infectious virus is present and can be recovered by traditional biological methods and (2) latent infection, i.e., infection wherein viral genome is present in the cell but infectious virus is generally not produced except during intermittent episodes of reactivation. Persistence generally involves stages of both productive and latent infection.

Lytic infections can also persist under conditions where only a small fraction of the total cells are infected (smoldering (cycling) infection). The few infected cells release virus and are killed, but the progeny virus again only infect a small number of the total cells. Examples of such smoldering infections include the persistence of lactic dehydrogenase virus in mice (Mahy, B. W. J., *Br. Med. Bull.* 41: 50–55 (1985)) and adenovirus infection in humans (Porter, D. D. pp. 784–790 in Baron, S., ed. *Medical Microbiology* 2d ed. (Addison-Wesley, Menlo Park, Calif. 1985)).

Furthermore, a virus may be lytic for some cell types but not for others. For example, evidence suggests that human immunodeficiency virus (HIV) is more lytic for T cells than for monocytes/macrophages, and therefore can result in a productive infection of T cells that can result in cell death, whereas HIV-infected mononuclear phagocytes may produce virus for considerable periods of time without cell lysis. (Klatzmann, et al. *Science* 225:59–62 (1984); Koyanagi, et al. *Science* 241:1673–1675 (1988); Sattentau, et al. *Cell* 52:631–633 (1988)).

Traditional treatments for viral infection include pharmaceuticals aimed at specific virus derived proteins, such as HIV protease or reverse transcriptase, or recombinant (cloned) immune modulators (host derived), such as the interferons. However, the current methods have several limitations and drawbacks which include high rates of viral mutations which render anti-viral pharmaceuticals ineffective. For immune modulators, limited effectiveness, limiting side effects, a lack of specificity all limit the general applicability of these agents. Also the rate of success with current antivirals and immune-modulators has been disappointing.

The current invention focuses on isolating genes that are not essential for cellular survival when disrupted in one or both alleles, but which are required for virus replication. This may occur with a dose effect, in which one allele knock-out may confer the phenotype of virus resistance for the cell. As targets for therapeutic intervention, inhibition of these cellular gene products, including: proteins, parts of

DETAILED DESCRIPTION OF THE INVENTION

The present invention utilizes a "gene trap" method along with a selection process to identify and isolate nucleic acids from genes associated with a particular function. Specifically, it provides a means of isolating cellular genes necessary for viral infection but not essential for the cell's survival, and it provides a means of isolating cellular genes that suppress tumor progression.

The present invention also provides a core discovery that virally infected cells become dependent upon at least one factor present in serum for survival, whereas non-infected cells do not exhibit this dependence. This core discovery has been utilized in the present invention in several ways. First, inhibition of the "serum survival factor" can be utilized to eradicate persistently virally infected cells from populations of non-infected cells. Inhibition of this factor can also be used to treat virus infection in a subject, as further described herein. Additionally, inhibition of or withdrawal of the serum survival factor in tissue culture allows for the detection of cellular genes required for viral replication yet nonessential for an uninfected cell to survive. The present invention further provides several such cellular genes, as well as methods of treating viral infections by inhibiting the functioning of such genes.

Furthermore, the present invention provides a method for isolation of cellular genes utilized in tumor progression.

The present method provides several cellular genes that are necessary for viral growth in the cell but are not essential for the cell to survive. These genes are important for lytic and persistent infection by viruses. These genes were isolated by generating gene trap libraries by infecting cells with a retrovirus gene trap vector, selecting for cells in which a gene trap event occurred (i.e., in which the vector had inserted such that the promoterless marker gene was inserted such that a cellular promoter promotes transcription of the marker gene, i.e., inserted into a functioning gene), starving the cells of serum, infecting the selected cells with the virus of choice while continuing serum starvation, and adding back serum to allow visible colonies to develop, which colonies were cloned by limiting dilution. Genes into which the retrovirus gene trap vector inserted were then isolated from the colonies using probes specific for the retrovirus proteins (modification enzymes that include, but are not restricted to glycosylation, lipid modifiers [myriolate, etc.]), lipids, transcription elements and RNA regulatory molecules, may be less likely to have profound toxic side effects and virus mutation is less likely to overcome the 'block' to replicate successfully.

The present invention provides a significant improvement over previous methods of attempted therapeutic intervention against viral infection by addressing the cellular genes required by the virus for growth. Therefore, the present invention also provides an innovative therapeutic approach to intervention in viral infection by providing methods to treat viruses by inhibiting the cellular genes necessary for viral infection. Because these genes, by virtue of the means by which they are originally detected, are nonessential to the cell's survival, these treatment methods can be used in a subject without serious detrimental effects to the subject, as has been found with previous methods. The present invention also provides the surprising discovery that virally infected cells are dependent upon a factor in serum to survive. Therefore, the present invention also provides a method for treating viral infection by inhibiting this serum survival factor. Finally, these discoveries also provide a novel method for removing virally infected cells from a cell culture by removing, inhibiting or disrupting this serum survival factor in the culture so that non-infected cells selectively survive.

The selection of tumor suppressor gene(s) has become an important area in the discovery of new target for therapeutic intervention of cancer. Since the discovery that cells are restricted from promiscuous entry into the cell cycle by specific genes that are capable of suppressing a 'transformed' phenotype, considerable time has been invested in the discovery of such genes. Some of these genes include the gene associated by rhabdomyosarcoma (Rb) and the p53 (apoptosis related) encoding gene. The present invention provides a method, using gene-trapping, to select cell lines that have transformed phenotype from cells that are not transformed and to isolate from these cells a gene that can suppress a malignant phenotype. Thus, by the nature of the isolation process, a function is associated with the isolated genes. The capacity to select quickly tumor suppressor genes can provide unique targets in the process of treating or preventing, and even for diagnostic testing of, cancer. gene trap vector. Thus nucleic acids isolated by this method are isolated portions of genes.

Thus the present invention provides a method of identifying a cellular gene necessary for viral growth in a cell and nonessential for cellular survival, comprising (a) transferring into a cell culture growing in serum-containing medium a vector encoding a selective marker gene lacking a functional promoter, (b) selecting cells expressing the marker gene, (c) removing serum from the culture medium, (d) infecting the cell culture with the virus, and (e) isolating from the surviving cells a cellular gene within which the marker gene is inserted, thereby identifying a gene necessary for viral growth in a cell and nonessential for cellular survival. The present invention also provides a method of identifying a cellular gene used for viral growth in a cell and nonessential for cellular survival, comprising (a) transferring into a cell culture growing in serum-containing medium a vector encoding a selective marker gene lacking a functional promoter, (b) selecting cells expressing the marker gene, (c) removing serum from the culture medium, (d) infecting the cell culture with the virus, and (e) isolating from the surviving cells a cellular gene within which the marker gene is inserted, thereby identifying a gene necessary for viral growth in a cell and nonessential for cellular survival. In any selected cell type, such as Chinese hamster ovary cells, one can readily determine if serum starvation is required for selection. If it is not, serum starvation may be eliminated from the steps.

Alternatively, instead of removing serum from the culture medium, a serum factor required by the virus for growth can be inhibited, such as by the administration of an antibody that specifically binds that factor. Furthermore, if it is believed that there are no persistently infected cells in the culture, the serum starvation step can be eliminated and the cells grown in usual medium for the cell type. If serum starvation is used, it can be continued for a time after the culture is infected with the virus. Serum can then be added back to the culture. If some other method is used to inactivate the factor, it can be discontinued, inactivated or removed (such as removing the anti-factor antibody, e.g., with a bound antibody directed against that antibody) prior to adding fresh serum back to the culture. Cells that survive are mutants having an inactivating insertion in a gene necessary for growth of the virus. The genes having the insertions can then be isolated by isolating sequences having the marker gene sequences. This mutational process disturbs a wild type function. A mutant gene may produce at a lower level a normal product, it may produce a normal product not normally found in these cells, it may cause the overproduction of a normal product, it may produce an altered product that has some functions but not others, or it may completely disrupt a gene function. Additionally, the mutation may disrupt an RNA that has a function but is never translated into a protein. For example, the alpha-tropomyosin gene has a 3' RNA that is very important in cell regulation but never is translated into protein. (*Cell* 75 pg 1107–1117, Dec. 17, 1993).

As used herein, a cellular gene "nonessential for cellular survival" means a gene for which disruption of one or both alleles results in a cell viable for at least a period of time which allows viral replication to be inhibited for preventative or therapeutic uses or use in research. A gene "necessary for viral growth" means the gene product, either protein or RNA, secreted or not, is necessary, either directly or indirectly in some way for the virus to grow, and therefore, in the absence of that gene product (i.e., a functionally available gene product), at least some of the cells containing the virus die. For example, such genes can encode cell cycle regulatory proteins, proteins affecting the vacuolar hydrogen pump, or proteins involved in protein folding and protein modification, including but not limited to: phosphorylation, methylation, glycosylation, myrislation or other lipid moiety, or protein processing via enzymatic processing. Some examples of such genes are exemplified herein, wherein some of the isolated nucleic acids correspond to genes such as vacuolar H+ATPase, alpha tropomyosin, gasS gene, ras complex, N-acetyl-glucosaminyltransferase I mRNA, and calcyclin.

Any virus capable of infecting the cell can be used for this method. Virus can be selected based upon the particular infection desired to study. However, it is contemplated by the present invention that many viruses will be dependent upon the same cellular genes for survival; thus a cellular gene isolated using one virus can be used as a target for therapy for other viruses as well. Any cellular gene can be tested for relevancy to any desired virus using the methods set forth herein, i.e., in general, by inhibiting the gene or its gene product in a cell and determining if the desired virus can grow in that cell. Some examples of viruses include HIV (including HIV-1 and HIV-2); parvovirus; papillomaviruses; hantaviruses; influenza viruses (e.g., influenza A, B and C viruses); hepatitis viruses A to G; caliciviruses; astroviruses; rotaviruses; coronaviruses, such as human respiratory coronavirus; picornaviruses, such as human rhinovirus and enterovirus; ebola virus; human herpesvirus (e.g., HSV-1-9); human cytomegalovirus; human adenovirus; Epstein-Barr virus; hantaviruses; for animal, the animal counterpart to any above listed human virus, animal retroviruses, such as simian immunodeficiency virus, avian immunodeficiency virus, bovine immunodeficiency virus, feline immunodeficiency virus, equine infectious anemia virus, caprine arthritis encephalitis virus or visna virus.

The nucleic acids comprising cellular genes of this invention were isolated by the above method and as set forth in the examples. The invention includes a nucleic acid comprising the nucleotide sequence set forth in SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74 or SEQ ID NO:75 (this list is sometimes referred to herein as "SEQ ID NO:5 through SEQ ID NO:75" for brevity). Thus these nucleic acids can contain, in addition to the nucleotides set forth in each SEQ ID NO in the sequence listing, additional nucleotides at either end of the molecule. Such additional nucleotides can be added by any standard method, as known in the art, such as recombinant methods and synthesis methods. Examples of such nucleic acids comprising the nucleotide sequence set forth in any entry of the sequence listing contemplated by this invention include, but are not limited to, for example, the nucleic acid placed into a vector; a nucleic acid having one or more regulatory region (e.g., promoter, enhancer, polyadenylation site) linked to it, particularly in functional manner, i.e. such that an mRNA or a protein can be produced; a nucleic acid including additional nucleic acids of the gene, such as a larger or even full length genomic fragment of the gene, a partial or full length cDNA, a partial or full length RNA. Making and/or isolating such larger nucleic acids is further described below and is well known and standard in the art.

The invention also provides a nucleic acid encoding the protein encoded by the gene comprising the nucleotide sequence set forth in SEQ ID NO:5, SEQ ID NO:6, SEQ ID NO.7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74 or SEQ ID NO:75, as well as allelic variants and homologs of each such gene. The gene is readily obtained using standard methods, as described below and as is known and standard in the art. The present invention also contemplates any unique fragment of these genes or of the nucleic acids set forth in any of SEQ ID NO:5 through SEQ ID NO:75. Examples of inventive fragments of the inventive genes are the nucleic acids whose sequence is set forth in any of SEQ ID NO:5 through SEQ ID NO:75. To be unique, the fragment must be of sufficient size to distinguish it from other known sequences, most readily determined by comparing any nucleic acid fragment to the nucleotide sequences of nucleic acids in computer databases, such as GenBank. Such comparative searches are standard in the art. Typically, a unique fragment useful as a primer or probe will be at least about 20 to about 25 nucleotides in length, depending upon the specific nucleotide content of the sequence. Additionally, fragments can be, for example, at least about 30, 40, 50, 75, 100, 200 or 500 nucleotides in length. The nucleic acids can be single or double stranded, depending upon the purpose for which it is intended.

The present invention further provides a nucleic acid comprising the regulatory region of a gene comprising the nucleotide sequences set forth in SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75. Additionally provided is a construct comprising such a regulatory region functionally linked to a reporter gene. Such reporter gene constructs can be used to screen for compounds and compositions that affect expression of the gene comprising the nucleic acids whose sequence is set forth in any of SEQ ID NO: 5 through SEQ ID NO: 75.

The nucleic acids set forth in the sequence listing are gene fragments; the entire coding sequence and the entire gene that comprises each fragment are both contemplated herein and are readily obtained by standard methods, given the nucleotide sequences presented in the sequence listing (see. e.g., Sam brook et al., *Molecular Cloning: A Laboratory Manual,* 2nd Ed., Cold Spring Harbor Laboratory, Cold Spring Harbor, N.Y., 1989; *DNA cloning: A Practical Approach,* Volumes I and II, Glover, D. M. ed., IRL Press Limited, Oxford, 1985). To obtain the entire genomic gene, briefly, a nucleic acid whose sequence is set forth in any of SEQ ID NO: 1 through SEQ ID NO:83, or preferably in any of SEQ ID NO:5 through SEQ ID NO:83, or a smaller fragment thereof, is utilized as a probe to screen a genomic library under high stringency conditions, and isolated clones are sequenced. Once the sequence of the new clone is determined, a probe can be devised from a portion of the new clone not present in the previous fragment and hybridized to the library to isolate more clones containing fragments of the gene. In this manner, by repeating this process in organized fashion, one can "walk" along the chromosome and eventually obtain nucleotide sequence for the entire gene. Similarly, one can use portions of the present fragments, or additional fragments obtained from the genomic library, that contain open reading frames to screen a cDNA library to obtain a cDNA having the entire coding sequence of the gene. Repeated screens can be utilized as described above to obtain the complete sequence from several clones if necessary. The isolates can then be sequenced to determine the nucleotide sequence by standard means such as dideoxynucleotide sequencing methods (see, e.g., Sambrook et al., *Molecular Cloning: A Laboratory Manual,* 2nd Ed., Cold Spring Harbor Laboratory, Cold Spring Harbor, N.Y., 1989).

The present genes were isolated from rat; however, homologs in any desired species, preferably mammalian, such as human, can readily be obtained by screening a human library, genomic or cDNA, with a probe comprising sequences of the nucleic acids set forth in the sequence listing herein, or fragments thereof, and isolating genes specifically hybridizing with the probe under preferably relatively high stringency hybridization conditions. For example, high salt conditions (e.g., in 6×SSC or 6×SSPE) and/or high temperatures of hybridization can be used. For example, the stringency of hybridization is typically about 5° C. to 20° C. below the $T_m$ (the melting temperature at which half of the molecules dissociate from its partner) for the given chain length. As is known in the art, the nucleotide composition of the hybridizing region factors in determining the melting temperature of the hybrid. For 20mer probes, or example, the recommended hybridization temperature is typically about 55–58° C. Additionally, the rat sequence can be utilized to devise a probe for a homolog in any specific animal by determining the amino acid sequence for a portion of the rat protein, and selecting a probe with optimized codon usage to encode the amino acid sequence of the homolog in that particular animal. Any isolated gene can be confirmed as the targeted gene by sequencing the gene to determine it contains the nucleotide sequence listed herein as comprising the gene. Any homolog can be confirmed as a homolog by its functionality.

Additionally contemplated by the present invention are nucleic acids, from any desired species, preferably mammalian and more preferably human, having 98%, 95%, 90%, 85%, 80%, 70%, 60%, or 50% homology, or greater, in the region of homology, to a region in an exon of a nucleic acid encoding the protein encoded by the gene comprising the nucleotide sequence set forth in any of SEQ ID NO:5 through SEQ ID NO:75 of the sequence listing or to homologs thereof. Also contemplated by the present invention are nucleic acids, from any desired species, preferably mammalian and more preferably human, having 98%, 95%, 90%, 85%, 80%, 70%, 60%, or 50% homology, or greater, in the region of homology, to a region in an exon of a nucleic acid comprising the nucleotide sequence set forth in any of SEQ ID NO:5 through SEQ ID NO:75 of the sequence listing or to homologs thereof. These genes can be synthesized or obtained by the same methods used to isolate homologs, with stringency of hybridization and washing, if desired, reduced accordingly as homology desired is decreased, and further, depending upon the G-C or A-T richness of any area wherein variability is searched for. Allelic variants of any of the present genes or of their homologs can readily be isolated and sequenced by screening additional libraries following the protocol above. Methods of making synthetic genes are described in U.S. Pat. No. 5,503,995 and the references cited therein.

The nucleic acid encoding any selected protein of the present invention can be any nucleic acid that functionally encodes that protein. For example, to functionally encode, i.e., allow the nucleic acid to be expressed, the nucleic acid can include, for example, exogenous or endogenous expression control sequences, such as an origin of replication, a promoter, an enhancer, and necessary information processing sites, such as ribosome binding sites, RNA splice sites, polyadenylation sites, and transcriptional terminator sequences. Preferred expression control sequences can be promoters derived from metallothionine genes, actin genes, immunoglobulin genes, CMV, SV40, adenovirus, bovine papilloma virus, etc. Expression control sequences can be selected for functionality in the cells in which the nucleic acid will be placed. A nucleic acid encoding a selected protein can readily be determined based upon the amino acid sequence of the selected protein, and, clearly, many nucleic acids will encode any selected protein.

The present invention additionally provides a nucleic acid that selectively hybridizes under stringent conditions with a nucleic acid encoding the protein encoded by the gene comprising the nucleotide sequence set forth in any sequence listed herein (i.e., any of SEQ ID NO:5 through SEQ ID NO:75). This hybridization can be specific. The degree of complementarity between the hybridizing nucleic acid and the sequence to which it hybridizes should be at least enough to exclude hybridization with a nucleic acid encoding an unrelated protein. Thus, a nucleic acid that selectively hybridizes with a nucleic acid of the present protein coding sequence will not selectively hybridize under stringent conditions with a nucleic acid for a different, unrelated protein, and vice versa. Typically, the stringency of hybridization to achieve selective hybridization involves hybridization in high ionic strength solution (6×SSC or 6×SSPE) at a temperature that is about 12–25° C. below the $T_m$ (the melting temperature at which half of the molecules dissociate from its partner) followed by washing at a combination of temperature and salt concentration chosen so that the washing temperature is about 5° C. to 20° C. below the $T_m$ of the hybrid molecule. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The washing temperatures can be used as described above to achieve selective stringency, as is known in the art. (Sambrook et al., *Molecular Cloning: A Laboratory Manual*, 2nd Ed., Cold Spring Harbor Laboratory, Cold Spring Harbor, N.Y., 1989; Kunkel et al. *Methods Enzymol.* 1987:154:367, 1987). Nucleic acid fragments that selectively hybridize to any given nucleic acid can be used, e.g., as primers and or probes for further hybridization or for amplification methods (e.g., polymerase chain reaction (PCR), ligase chain reaction (LCR)). A preferable stringent hybridization condition for a DNA:DNA hybridization can be at about 68° C. (in aqueous solution) in 6×SSC or 6×SSPE followed by washing at 68° C.

The present invention additionally provides a protein encoded by a nucleic acid encoding the protein encoded by the gene comprising any of the nucleotide sequences set forth herein (i.e., any of SEQ ID NO: 5 through SEQ ID NO:75). The protein can be readily obtained by any of several means. For example, the nucleotide sequence of coding regions of the gene can be translated and then the corresponding polypeptide can be synthesized mechanically by standard methods. Additionally, the coding regions of the genes can be expressed or synthesized, an antibody specific for the resulting polypeptide can be raised by standard methods (see, e.g., Harlow and Lane, *Antibodies: A Laboratory Manual*, Cold Spring Harbor Laboratory, Cold Spring Harbor, N.Y., 1988), and the protein can be isolated from other cellular proteins by selective hybridization with the antibody. This protein can be purified to the extent desired by standard methods of protein purification (see, e.g., Sambrook et al., *Molecular Cloning: A Laboratory Manual*, 2nd Ed., Cold Spring Harbor Laboratory, Cold Spring Harbor, N.Y., 1989). The amino acid sequence of any protein, polypeptide or peptide of this invention can be deduced from the nucleic acid sequence, or it can be determined by sequencing an isolated or recombinantly produced protein.

The terms "peptide," "polypeptide" and "protein" are used interchangeably herein and refer to a polymer of amino acids and includes full-length proteins and fragments thereof As used in the specification and in the claims, "a" can mean one or more, depending upon the context in which it is used. An amino acid residue is an amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. Standard polypeptide nomenclature (described in *J. Biol. Chem.*, 243:3552–59 (1969) and adopted at 37 CFR §1.822(b)) is used herein.

As will be appreciated by those skilled in the art, the invention also includes those polypeptides having slight variations in amino acid sequences or other properties. Amino acid substitutions can be selected by known parameters to be neutral (see, e.g., Robinson W E Jr, and Mitchell W M., AIDS 4:S151–S162(1990)). Such variations may arise naturally as allelic variations (e.g., due to genetic polymorphism) or may be produced by human intervention (e.g., by mutagenesis of cloned DNA sequences), such as induced point, deletion, insertion and substitution mutants. Minor changes in amino acid sequence are generally preferred, such as conservative amino acid replacements, small internal deletions or insertions, and additions or deletions at the ends of the molecules. Substitutions may be designed based on, for example, the model of Dayhoff, et al. (in *Atlas of Protein Sequence and Structure* 1978, Nat'l Biomed. Res. Found., Washington, D.C.). These modifications can result in changes in the amino acid sequence, provide silent mutations, modify a restriction site, or provide other specific mutations. Likewise, such amino acid changes result in a different nucleic acid encoding the polypeptides and proteins. Thus, alternative nucleic acids are also contemplated by such modifications.

The present invention also provides cells containing a nucleic acid of the invention. A cell containing a nucleic acid encoding a protein typically can replicate the DNA and, further, typically can express the encoded protein. The cell can be a prokaryotic cell, particularly for the purpose of producing quantities of the nucleic acid, or a eukaryotic cell, particularly a mammalian cell. The cell is preferably a mammalian cell for the purpose of expressing the encoded protein so that the resultant produced protein has mammalian protein processing modifications.

Nucleic acids of the present invention can be delivered into cells by any selected means, in particular depending upon the purpose of the delivery of the compound and the target cells. Many delivery means are well-known in the art. For example, electroporation, calcium phosphate precipitation, microinjection, cationic or anionic liposomes, and liposomes in combination with a nuclear localization signal peptide for delivery to the nucleus can be utilized, as is known in the art.

The present invention also contemplates that the mutated cellular genes necessary for viral growth, produced by the present method, as well as cells containing these mutants can also be useful. These mutated genes and cells containing them can be isolated and/or produced according to the methods herein described and using standard methods.

It should be recognized that the sequences set forth herein may contain minor sequencing errors. Such errors can be corrected, for example, by using the hybridization procedure described above with various probes derived from the described sequences such that the coding sequence can be reisolated and resequenced.

As described in the examples, the present invention provides the discovery of a "serum survival factor" present in serum that is necessary for the survival of persistently virally infected cells. Isolation and characterization of this factor have shown it to be a protein, to have a molecular weight of between about 50 kD and 100 kD, to resist inactivation in low pH (e.g., pH2) and chloroform extraction, to be inactivated by boiling for about 5 minutes and in low ionic strength solution (e.g., about 10 mM to about 50 mM). The present invention thus provides a purified mammalian serum protein having a molecular weight of between about 50 kD and 100 kD which resists inactivation in low pH and resists inactivation by chloroform extraction, which inactivates when boiled and inactivates in low ionic strength solution, and which when removed from a cell culture comprising cells persistently infected with reovirus selectively substantially prevents survival of cells persistently infected with reovirus. The factor, fitting the physical characteristics described above, can readily be verified by adding it to non-serum-containing medium (which previously could not support survival of persistently virally infected cells) and determining whether this medium with the added putative factor can now support persistently virally infected cells, particularly cells persistently infected with reovirus. As used herein, a "purified" protein means the protein is at least of sufficient purity such that an approximate molecular weight can be determined.

The amino acid sequence of the protein can be elucidated by standard methods. For example, an antibody to the protein can be raised and used to screen an expression library to obtain nucleic acid sequence coding the protein. This nucleic acid sequence is then simply translated into the corresponding amino acid sequence. Alternatively, a portion of the protein can be directly sequenced by standard amino acid sequencing methods (amino-terminus sequencing). This amino acid sequence can then be used to generate an array of nucleic acid probes that encompasses all possible coding sequences for a portion of the amino acid sequence. The array of probes is used to screen a cDNA library to obtain the remainder of the coding sequence and thus ultimately the corresponding amino acid sequence.

The present invention also provides methods of detecting and isolating additional serum survival factors. For example, to determine if any known serum components are necessary for viral growth, the known components can be inhibited in, or eliminated from, the culture medium, and it can be observed whether viral growth is inhibited by determining if persistently infected cells do not survive. One can add the factor back (or remove the inhibition) and determine whether the factor allows for viral growth.

Additionally, other, unknown serum components can also be found to be essential for viral growth. Serum can be fractionated by various standard means, and fractions added to serum free medium to determine if a factor is present in a reaction that allows viral growth previously inhibited by the lack of serum. Fractions having this activity can then be further fractionated until the factor is relatively free of other components. The factor can then be characterized by standard methods, such as size fractionation, denaturation and/or inactivation by various means, etc. Preferably, once the factor has been purified to a desired level of purity, it is added to cells in serum free medium to confirm that it bestows the function of allowing virus to grow when serum-free medium alone did not. This method can be repeated to confirm the requirement for the specific factor for any desired virus, since each serum factor found to be required by any one virus can also be required by many other viruses. In general, the closer the viruses are related and the more similar the infection modes of the viruses, the more likely that a factor required by one virus will be required by the other.

The present invention also provides methods of treating virus infections utilizing applicants' discoveries. The subject of any of the herein described methods can be any animal, preferably a mammal, such as a human, a veterinary animal, such as a cat, dog, horse, pig, goat, sheep, or cow, or a laboratory animal, such as a mouse, rat, rabbit, or guinea pig, depending upon the virus.

The present invention provides a method of reducing or inhibiting, and thereby treating, a viral infection in a subject, comprising administering to the subject an inhibiting amount of a composition that inhibits functioning of the serum protein described herein, i.e. the serum protein having a molecular weight of between about 50 kD and 100 kD which resists inactivation in low pH and resists inactivation by chloroform extraction, which inactivates when boiled and inactivates in low ionic strength solution, and which when removed from a cell culture comprising cells persistently infected with the virus prevents survival of at least some cells persistently infected with the virus, thereby treating the viral infection. The composition can comprise, for example, an antibody that specifically binds the serum protein, or an antisense RNA that binds an RNA encoded by a gene functionally encoding the serum protein.

Any virus capable of infecting the selected subject to be treated can be treated by the present method. As described above, any serum protein or survival factor found by the present methods to be necessary for growth of any one virus can be found to be necessary for growth of many other viruses. For any given virus, the serum protein or factor can be confirmed to be required for growth by the methods described herein. The cellular genes identified by the examples using reovirus, a mammalian pathogen, and a rat cell system have general applicability to other virus infections that include all of the known as well as yet to be discovered human pathogens, including, but not limited to: human immunodeficiency viruses (e.g., HIV-1, HIV-2); parvovirus; papillomaviruses; hantaviruses; influenza viruses (e.g., influenza A, B and C viruses); hepatitis viruses A to G; caliciviruses; astroviruses; rotaviruses; coronaviruses, such as human respiratory coronavirus; picornaviruses, such as human rhinovirus and enterovirus; ebola virus; human herpesvirus (e.g., HSV-1-9); human cytomegalovirus; human adenovirus; Epstein-Barr virus; hantaviruses; for animal, the animal counterpart to any above listed human virus, animal retroviruses, such as simian immunodeficiency virus, avian immunodeficiency virus, bovine immunodeficiency virus, feline immunodeficiency virus, equine infectious anemia virus, caprine arthritis encephalitis virus or visna virus.

A protein inhibiting amount of the composition can be readily determined, such as by administering varying amounts to cells or to a subject and then adjusting the effective amount for inhibiting the protein according to the volume of blood or weight of the subject. Compositions that bind to the protein can be readily determined by running the putatively bound protein on a protein gel and observing an alteration in the protein's migration through the gel. Inhibition of the protein can be determined by any desired means such as adding the inhibitor to complete media used to maintain persistently infected cells and observing the cells' viability. The composition can comprise, for example, an antibody that specifically binds the serum protein. Specific binding by an antibody means that the antibody can be used to selectively remove the factor from serum or inhibit the factor's biological activity and can readily be determined by radio immune assay (RIA), bioassay, or enzyme-linked immunosorbant (ELISA) technology. The composition can comprise, for example, an antisense RNA that specifically binds an RNA encoded by the gene encoding the serum protein. Antisense RNAs can be synthesized and used by standard methods (e.g., *Antisense RNA and DNA*, D. A. Melton, Ed., Cold Spring Harbor Laboratory, Cold Spring Harbor, N.Y. (1988)).

The present methods provide a method of screening a compound for treating a viral infection, comprising administering the compound to a cell containing a cellular gene functionally encoding a gene product necessary for reproduction of the virus in the cell but not necessary for survival of the cell and detecting level of the gene product produced, a decrease or elimination of the gene product indicating a compound for treating the viral infection. The present methods also provide a method of screening a compound for effectiveness in treating a viral infection, comprising administering the compound to a cell containing a cellular gene functionally encoding a gene product necessary for reproduction of the virus in the cell but not necessary for survival of the cell and detecting the level of the gene product produced, a decrease or elimination of the gene product indicating a compound effective for treating the viral infection. The cellular gene can be, for example, any gene provided herein, i.e., any of the genes comprising the nucleotide sequences set forth in any of SEQ ID NO:1 through SEQ ID NO:75, or any other gene obtained using the methods provided herein for obtaining such genes. Level of the gene product can be measured by any standard means, such as by detection with an antibody specific for the protein. The level of gene product can be compared to the level of the gene product in a control cell not contacted with the compound. The level of gene product can be compared to the level of the gene product in the same cell prior to addition of the compound. Relatedly, the regulatory region of the gene can be functionally linked to a reporter gene and compounds can be screened for inhibition of the reporter gene. Such reporter constructs are described herein.

The present invention provides a method of selectively eliminating cells persistently infected with a virus from an animal cell culture capable of surviving for a first period of time in the absence of serum, comprising propagating the cell culture in the absence of serum for a second time period which a persistently infected cell cannot survive without serum, thereby selectively eliminating from the cell culture cells persistently infected with the virus. The second time period should be shorter than the first time period. Thus one can simply eliminate serum from a standard culture medium composition for a period of time (e.g. by removing serum containing medium from the culture container, rinsing the cells, and adding serum-free medium back to the container), then, after a time of serum starvation, return serum to the culture medium. Alternatively, one can inhibit a serum survival factor from the culture in place of the step of serum starvation. Furthermore, one can instead interfere with the virus-factor interaction. Such a viral elimination method can periodically be performed for cultured cells to ensure that they remain virus-free. The time period of serum removal can greatly vary, with a typical range being about 1 to about 30 days, a preferable period can be about 3 to about 10 days, and a more preferable period can be about 5 days to about 7 days. This time period can be selected based upon ability of the specific cell to survive without serum as well as the life cycle of the virus, e.g., for reovirus, which has a life cycle of about 24 hours, 3 days' starvation of cells provides dramatic results.

Furthermore, the time period can be shortened by also passaging the cells during the starvation; in general, increasing the number of passages can decrease the time of serum starvation (or serum factor inhibition) needed to get full clearance of the virus from the culture. While passaging, the cells typically are exposed briefly to serum (typically for about 3 to about 24 hours). This exposure both stops the action of the trypsin used to dislodge the cells and stimulates the cells into another cycle of growth, thus aiding in this selection process. Thus a starvation/serum cycle can be repeated to optimize the selective effect. Other standard culture parameters, such as confluency of the cultures, pH, temperature, etc. can be varied to alter the needed time period of serum starvation (or serum survival factor inhibition). This time period can readily be determined for any given viral infection by simply removing the serum for various periods of time, then testing the cultures for the presence of the infected cells (e.g., by ability to survive in the absence of serum and confirmed by quantitating virus in cells by standard virus titration and immunohistochemical techniques) at each tested time period, and then detecting at which time periods of serum deprivation the virally infected cells were eliminated. It is preferable that shorter time periods of serum deprivation that still provide elimination of the persistently infected cells be used. Furthermore, the cycle of starvation, then adding back serum and determining amount of virus remaining in the culture can be repeated until no virtually infected cells remain in the culture.

Thus, the present method can further comprise passaging the cells, i.e., transferring the cell culture from a first container to a second container. Such transfer can facilitate the selective lack of survival of virally infected cells. Transfer can be repeated several times. Transfer is achieved by standard methods of tissue culture (see, e.g., Freshney, *Culture of Animal Cells, A Manual of Basic Technique,* 2nd Ed. Alan R. Liss, Inc., New York, 1987).

The present method further provides a method of selectively eliminating from a cell culture cells persistently infected with a virus, comprising propagating the cell culture in the absence of a functional form of the serum protein having a molecular weight of between about 50 kD and 100 kD which resists inactivation in low pH and resists inactivation by chloroform extraction, which inactivates when boiled and inactivates in low ionic strength solution, and which when removed from a cell culture comprising cells persistently infected with reovirus substantially prevents survival of cells persistently infected with reovirus. The absence of the functional form can be achieved by any of several standard means, such as by binding the protein to an antibody selective for it (binding the antibody in serum either before or after the serum is added to the cells; if before, the serum protein can be removed from the serum by, e.g., binding the antibody to a column and passing the serum over the column and then administering the survival protein-free serum to the cells), by administering a compound that inactivates the protein, or by administering a compound that interferes with the interaction between the virus and the protein.

Thus, the present invention provides a method of selectively eliminating from a cell culture propagated in serum-containing medium cells persistently infected with a virus, comprising inhibiting in the serum the protein having a molecular weight of between about 50 kD and 100 kD which resists inactivation in low pH and resists inactivation by chloroform extraction, which inactivates when boiled and inactivates in low ionic strength solution, and which when removed from a cell culture comprising cells persistently infected with reovirus substantially prevents survival of cells persistently infected with reovirus. Alternatively, the interaction between the virus and the serum protein can be disrupted to selectively eliminate cells persistently infected with the virus.

Any virus capable of some form of persistent infection may be eliminated from a cell culture utilizing the present elimination methods, including removing, inhibiting or otherwise interfering with a serum protein, such as the one exemplified herein, and also including removing, inhibiting or otherwise interfering with a gene product from any cellular gene found by the present method to be necessary for viral growth yet nonessential to the cell. For example, DNA viruses or RNA viruses can be targeted. One can readily determine whether cells infected with a selected virus can be selectively removed from a culture through removal of serum by starving cells permissive to the virus of serum (or inhibiting the serum survival factor), adding the selected virus to the cells, adding serum to the culture, and observing whether infected cells die (i.e., by titering levels of virus in the surviving cells with an antibody specific for the virus).

A culture of any animal cell (i.e., any cell that is typically grown and maintained in culture in serum) that can be maintained for a period of time in the absence of serum, can be purified from viral infection utilizing the present method. For example, primary cultures as well as established cultures and cell lines can be used. Furthermore, cultures of cells from any animal and any tissue or cell type within that animal that can be cultured and that can be maintained for a period of time in the absence of serum can be used. For example, cultures of cells from tissues typically infected, and particularly persistently infected, by an infectious virus could be used.

As used in the claims "in the absence of serum" means at a level at which persistently virally infected cells do not survive. Typically, the threshold level is about 1% serum in the media. Therefore, about 1% serum or less can be used, such as about 1%, 0.75%, 0.50%. 0.25% 0.1% or no serum can be used.

As used herein, "selectively eliminating" cells persistently infected with a virus means that substantially all of the cells persistently infected with the virus are killed such that the presence of virally infected cells cannot be detected in the culture immediately after the elimination procedure has been performed. Furthermore, "selectively eliminating" includes that cells not infected with the virus are generally not killed by the method. Some surviving cells may still produce virus but at a lower level, and some may be defective in pathways that lead to death by the virus. Typically, for cells persistently infected with virus to be substantially all killed, more than about 90% of the cells, and more preferably less than about 95%, 98%, 99%, or 99.99% of virus-containing cells in the culture are killed.

The present method also provides a nucleic acid comprising the regulatory region of any of the genes. Such regulatory regions can be isolated from the genomic sequences isolated and sequenced as described above and identified by any characteristics observed that are characteristic for regulatory regions of the species and by their relation to the start codon for the coding region of the gene. The present invention also provides a construct comprising the regulatory region functionally linked to a reporter gene. Such constructs are made by routine subcloning methods, and many vectors are available into which regulatory regions can be subcloned upstream of a marker gene. Marker genes can be chosen for ease of detection of marker gene product.

The present method therefore also provides a method of screening a compound for treating a viral infection, comprising administering the compound to a cell containing any of the above-described constructs, comprising a regulatory region of one of the genes comprising the nucleotide sequence set forth in any of SEQ ID NO:1 through SEQ ID NO:75 functionally linked to a reporter gene, and detecting the level of the reporter gene product produced, a decrease or elimination of the reporter gene product indicating a compound for treating the viral infection. Compounds detected by this method would inhibit transcription of the gene from which the regulatory region was isolated, and thus, in treating a subject, would inhibit the production of the gene product produced by the gene, and thus treat the viral infection.

The present invention additionally provides a method of reducing or inhibiting a viral infection in a subject, comprising administering to the subject an amount of a composition that inhibits expression or functioning of a gene product encoded by a gene comprising the nucleic acid set forth in any of SEQ ID NO:1 through SEQ ID NO:75, or a homolog thereof, thereby treating the viral infection. the composition can comprise, for example, an antibody that binds a protein encoded by the gene. The composition can also comprise an antibody that binds a receptor for a protein encoded by the gene. Such an antibody can be raised against the selected protein by standard methods, and can be either polyclonal or monoclonal, though monoclonal is preferred. Alternatively, the composition can comprise an antisense RNA that binds an RNA encoded by the gene. Furthermore, the composition can comprise a nucleic acid functionally encoding an antisense RNA that binds an RNA encoded by the gene. Other useful compositions will be readily apparent to the skilled artisan.

The present invention further provides a method of reducing or inhibiting a viral infection in a subject comprising mutating ex vivo in a selected cell from the subject an endogenous gene comprising the nucleic acid set forth in any of SEQ ID NO:1 through SEQ ID NO:75, or a homolog thereof, to a gene form incapable of producing a functional gene product of the gene or a gene form producing a reduced amount of a functional gene product of the gene, and replacing the cell in the subject, thereby reducing viral infection of cells in the subject. The cell can be selected according to the typical target cell of the specific virus whose infection is to be reduced, prevented or inhibited. A preferred cell for several viruses is a hematopoietic cell. When the selected cell is a hematopoietic cell, viruses which can be reduced or inhibited from infection can include, for example, HIV, including HIV-1 and HIV-2.

The present invention also provides a method of reducing or inhibiting a viral infection in a subject comprising mutating ex vivo in a selected cell from the subject an endogenous gene comprising a nucleic acid isolated by a method comprising (a) transferring into a cell culture growing in serum-containing medium a vector encoding a selective marker gene lacking a functional promoter, (b) selecting cells expressing the marker gene, (c) removing serum from the culture medium, (d) infecting the cell culture with the virus, and (e) isolating from the surviving cells a cellular gene within which the marker gene is inserted, to a mutated gene form incapable of producing a functional gene product of the gene or to a mutated gene form producing a reduced amount of a functional gene product of the gene, and replacing the cell in the subject, thereby reducing viral infection of cells in the subject. Thus the mutated gene form can be one incapable of producing an effective amount of a functional protein or mRNA, or one incapable of producing a functional protein or mRNA, for example. The method can be performed wherein the virus is HIV. The method can be performed in any selected cell in which the virus may infect with deleterious results. For example, the cell can be a hematopoietic cell. However, many other virus-cell combinations will be apparent to the skilled artisan.

The present invention additionally provides a method of increasing viral infection resistance in a subject comprising mutating ex vivo in a selected cell from the subject an endogenous gene comprising a nucleic acid isolated by a method comprising (a) transferring into a cell culture growing in serum-containing medium a vector encoding a selective marker gene lacking a functional promoter, (b) selecting cells expressing the marker gene, (c) removing serum from the culture medium, (d) infecting the cell culture with the virus, and (e) isolating from the surviving cells a cellular gene within which the marker gene is inserted, to a mutated gene form incapable of producing a functional gene product of the gene or a gene form producing a reduced amount of a functional gene product of the gene, and replacing the cell in the subject, thereby reducing viral infection of cells in the subject. The virus can be HIV, particularly when the cell is a hematopoietic cell. However, many other virus-cell combinations will be apparent to the skilled artisan.

The present invention provides a method of identifying a cellular gene that can suppress a malignant phenotype in a cell, comprising (a) transferring into a cell culture incapable of growing well in soft agar or Matrigel a vector encoding a selective marker gene lacking a functional promoter, (b) selecting cells expressing the marker gene, and (c) isolating from selected cells which are capable of growing in soft agar or Matrigel a cellular gene within which the marker gene is inserted, thereby identifying a gene that can suppress a malignant phenotype in a cell. This method can be performed using any selected non-transformed cell line, of which many are known in the art.

The present invention additionally provides a method of identifying a cellular gene that can suppress a malignant phenotype in a cell, comprising (a) transferring into a cell culture of non-transformed cells a vector encoding a selective marker gene lacking a functional promoter, (b) selecting cells expressing the marker gene, and (c) isolating from selected and transformed cells a cellular gene within which the marker gene is inserted, thereby identifying a gene that can suppress a malignant phenotype in a cell. A non-transformed phenotype can be determined by any of several standard methods in the art, such as the exemplified inability to grow in soft agar, or inability to grow in Matrigel.

The present invention further provides a method of screening for a compound for suppressing a malignant phenotype in a cell comprising administering the compound to a cell containing a cellular gene functionally encoding a gene product involved in establishment of a malignant phenotype in the cell and detecting the level of the gene product produced, a decrease or elimination of the gene product indicating a compound effective for suppressing the malignant phenotype. Detection of the level, or amount, of gene product produced can be measured, directly or indirectly, by any of several methods standard in the art (e.g., protein gel, antibody-based assay, detecting labeled RNA) for assaying protein levels or amounts, and selected based upon the specific gene product.

The present invention further provides a method of suppressing a malignant phenotype in a cell in a subject, comprising administering to the subject an amount of a composition that inhibits expression or functioning of a gene product encoded by a gene comprising the nucleic acid set forth in SEQ ID NO:76, SEQ ID NO:77, SEQ ID NO:78, SEQ ID NO:79, SEQ ID NO:80, SEQ ID NO:81, SEQ ID NO:82 or SEQ ID NO:83, or a homolog thereof, thereby suppressing a malignant phenotype. The composition can, for example, comprise an antibody that binds a protein encoded by the gene. The composition can, as another example, comprise an antibody that binds a receptor for a protein encoded by the gene. The composition can comprise an antisense RNA that binds an RNA encoded by the gene. Further, the composition can comprise a nucleic acid functionally encoding an antisense RNA that binds an RNA encoded by the gene.

Diagnostic or therapeutic agents of the present invention can be administered to a subject or an animal model by any of many standard means for administering therapeutics or diagnostics to that selected site or standard for administering that type of functional entity. For example, an agent can be administered orally, parenterally (e.g., intravenously), by intramuscular injection, by intraperitoneal injection, topically, transdermally, or the like. Agents can be administered, e.g., as a complex with cationic liposomes, or encapsulated in anionic liposomes. Compositions can include various amounts of the selected agent in combination with a pharmaceutically acceptable carrier and, in addition, if desired, may include other medicinal agents, pharmaceutical agents, carriers, adjuvants, diluents, etc.

Parental administration, if used, is generally characterized by injection. Injectables can be prepared in conventional forms, either as liquid solutions or suspensions, solid forms suitable for solution or suspension in liquid prior to injection, or as emulsions. Depending upon the mode of administration, the agent can be optimized to avoid degradation in the subject, such as by encapsulation, etc.

Dosages will depend upon the mode of administration, the disease or condition to be treated, and the individual subject's condition, but will be that dosage typical for and used in administration of antiviral or anticancer agents. Dosages will also depend upon the composition being administered, e.g., a protein or a nucleic acid. Such dosages are known in the art. Furthermore, the dosage can be adjusted according to the typical dosage for the specific disease or condition to be treated. Furthermore, viral titers in culture cells of the target cell type can be used to optimize the dosage for the target cells in vivo, and transformation from varying dosages achieved in culture cells of the same type as the target cell type can be monitored. Often a single dose can be sufficient; however, the dose can be repeated if desirable. The dosage should not be so large as to cause adverse side effects. Generally, the dosage will vary with the age, condition, sex and extent of the disease in the patient and can be determined by one of skill in the art. The dosage can also be adjusted by the individual physician in the event of any complication.

For administration to a cell in a subject, the composition, once in the subject, will of course adjust to the subject's body temperature. For ex vivo administration, the composition can be administered by any standard methods that would maintain viability of the cells, such as by adding it to culture medium (appropriate for the target cells) and adding this medium directly to the cells. As is known in the art, any medium used in this method can be aqueous and non-toxic so as not to render the cells non-viable. In addition, it can contain standard nutrients for maintaining viability of cells, if desired. For in vivo administration, the complex can be added to, for example, a blood sample or a tissue sample from the patient, or to a pharmaceutically acceptable carrier, e.g., saline and buffered saline, and administered by any of several means known in the art. Examples of administration include parenteral administration, e.g., by intravenous injection including regional perfusion through a blood vessel supplying the tissues(s) or organ(s) having the target cell(s), or by inhalation of an aerosol, subcutaneous or intramuscular injection, topical administration such as to skin wounds and lesions, direct transfection into, e.g., bone marrow cells prepared for transplantation and subsequent transplantation into the subject, and direct transfection into an organ that is subsequently transplanted into the subject. Further administration methods include oral administration, particularly when the composition is encapsulated, or rectal administration, particularly when the composition is in suppository form. A pharmaceutically acceptable carrier includes any material that is not biologically or otherwise undesirable, i.e., the material may be administered to an individual along with the selected complex without causing any undesirable biological effects or interacting in a deleterious manner with any of the other components of the pharmaceutical composition in which it is contained.

Specifically, if a particular cell type in vivo is to be targeted, for example, by regional perfusion of an organ or tumor, cells from the target tissue can be biopsied and optimal dosages for import of the complex into that tissue can be determined in vitro, as described herein and as known in the art, to optimize the in vivo dosage, including concentration and time length. Alternatively, culture cells of the same cell type can also be used to optimize the dosage for the target cells in vivo.

For either ex vivo or in vivo use, the complex can be administered at any effective concentration. An effective concentration is that amount that results in reduction, inhibition or prevention of the viral infection or in reduction or inhibition of transformed phenotype of the cells.

A nucleic acid can be administered in any of several means, which can be selected according to the vector utilized, the organ or tissue, if any, to be targeted, and the characteristics of the subject. The nucleic acids, if desired in a pharmaceutically acceptable carrier such as physiological saline, can be administered systemically, such as intravenously, intraarterially, orally, parenterally, subcutaneously. The nucleic acids can also be administered by direct injection into an organ or by injection into the blood vessel supplying a target tissue. For an infection of cells of the lungs or trachea, it can be administered intratracheally. The nucleic acids can additionally be administered topically, transdermally, etc.

The nucleic acid or protein can be administered in a composition. For example, the composition can comprise other medicinal agents, pharmaceutical agents, carriers, adjuvants, diluents, etc. Furthermore, the composition can comprise, in addition to the vector, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a vector and a cationic liposome can be administered to the blood afferent to a target organ or inhaled into the respiratory tract to target cells of the respiratory tract. Regarding liposomes, see, e.g., Brigham et al. *Am. J Resp. Cell. Mol. Biol.* 1:95–100 (1989); Feigner et al. *Proc. Natl. Acad. Sci USA* 84:7413–7417 (1987); U.S. Pat. No. 4,897,355.

For a viral vector comprising a nucleic acid, the composition can comprise a pharmaceutically acceptable carrier such as phosphate buffered saline or saline. The viral vector can be selected according to the target cell, as known in the art. For example, adenoviral vectors, in particular replication-deficient adenoviral vectors, can be utilized to target any of a number of cells, because of its broad host range. Many other viral vectors are available, and their target cells known.

EXAMPLES
Selective Elimination of Virally Infected Cells from a Cell Culture

Rat intestinal cell line-1 cells (RIE-1 cells) were standardly grown in Dulbecco's modified eagle's medium, high glucose, supplemented with 10% fetal bovine serum. To begin the experiment, cells persistently infected with reovirus were grown to near confluence, then serum was removed from the growth medium by removing the medium, washing the cells in PBS, and returning to the flask medium not supplemented with serum. Typically, the serum content was reduced to 1% or less. The cells are starved for serum for several days, or as long as about a month, to bring them to quiescence or growth arrest. Media containing 10% serum is then added to the quiescent cells to stimulate growth of the cells. Surviving cells are found to not be persistently infected cells by immunohistochemical techniques used to establish whether cells contain any infectious virus (sensitivity to 1 infectious virus per ml of homogenized cells).

Cellular Genomic DNA Isolation

Gene Trap Libraries: The libraries are generated by infecting the RIE-1 cells with a retrovirus vector (U3 gene-trap) at a ratio of less than one retrovirus for every ten cells. When a U3 gene trap retrovirus integrates within an actively transcribed gene, the neomycin resistance gene that the U3 gene trap retrovirus encodes is also transcribed, this confers resistance to the cell to the antibiotic neomycin. Cells with gene trap events are able to survive exposure to neomycin while cells without a gene trap event die. The various cells that survive neomycin selection are then propagated as a library of gene trap events. Such libraries can be generated with any retrovirus vector that has the properties of expressing a reporter gene from a transcriptionally active cellular promoter that tags the gene for later identification.

Reovirus selection: Reovirus infection is typically lethal to RIE-1 cells but can result in the development of persistently infected cells. These cells continue to grow while producing infective reovirus particles. For the identification of gene trap events that confer reovirus resistance to cells, the persistently infected cells must be eliminated or they will be scored as false positives. We have found that RIE-1 cells persistently infected with reovirus are very poorly tolerant to serum starvation, passaging and plating at low density. Thus, we have developed protocols for the screening of the RIE-1 gene trap libraries that select against both reovirus sensitive cells and cells that are persistently infected with reovirus.

1. RIE-1 library cells are grown to near confluence and then the serum is removed from the media. The cells are starved for serum for several days to bring them to quiescent or growth arrest.
2. The library cells are infected with reovirus at a titer of greater than ten reovirus per cell and the serum starvation is continued for several more days.
3. The infected cells are passaged, (a process in which they are exposed to serum for three to six hours) and then starved for serum for several more days.
4. The surviving cells are then allowed to grow in the presence of serum until visible colonies develop at which point they are cloned by limiting dilution.

MEDIA: DULBECCO'S MODIFIED EAGLE'S MEDIUM, HIGH GLUCOSE (DME/HIGH) Hyclone Laboratories cat. no. SH30003.02.

NEOMYCIN: The antibiotic used to select against the cells that did not have a U3 gene trap retrovirus. We used GENETICIN, from Sigma. cat. no. G9516.

RAT INTESTINAL CELL LINE-1 CELLS (RIE-1 CELLS): These cells are from the laboratory of Dr. Ray Dubois (VAMC). They are typically cultured in Dulbecco's Modified Eagle's Medium supplemented with 10% fetal calf serum.

REOVIRUS: Laboratory strains of either serotype 1 or serotype 3 are used. They were originally obtained from the laboratories of Bernard N. Fields (deceased). These viruses have been described in detail.

RETROVIRUS: The U3 gene trap retrovirus used here were developed by Dr. Earl Ruley (VAMC) and the libraries were produced using a general protocol suggested by him.

SERUM: FETAL BOVINE SERUM Hyclone Laboratories cat. no. A-1115-L.

Genes Necessary for Viral Infection

Characteristics of some of the isolated sequences include the following:

SEQ ID NO:1—rat genomic sequence of vacuolar H+ATPase (chemically inhibiting the activity of the gene product results in resistance to influenza virus and reovirus)

SEQ ID NO:2—rat alpha tropomyosin genomic sequence

SEQ ID NO:3—rat genomic sequence of murine and rat gasS gene (cell cycle regulated gene)

SEQ ID NO:4—rat genomic sequence of p162 of ras complex, mouse, human (cell cycle regulated gene)

SEQ ID NO:5—similar to N-acetyl-glucosaminyltransferase I mRNA, mouse, human (enzyme located in the Golgi region in the cell; has been found as part of a DNA containing virus)

SEQ ID NO:6—similar to calcyclin, mouse, human, reverse complement (cell cycle regulated gene)

SEQ ID NO:7—contains sequence similar to :LOCUS AA254809 364 bp mRNA EST DEFINITION mz75a10.r1 Soares mouse lymph node NbMLN Mus musculus cDNA clone 719226 5'

SEQ ID NO:8—contains a sequence similar to No SW:RSP1_MOUSE Q01730 RSP-1 PROTEIN SEQ ID NO:9—contains 5' UTR of gb|U25435|HSU25435 Human transcriptional repressor (CTCF) mRNA, complete cds, Length=3780

SEQ ID NO:38—similar to cDNA of retroviral origin

SEQ ID NO: 50—trapped AYU-6 genetic element

Isolation of Cellular Genes that Suppress a Malignant Phenotype

We have utilized a gene-trap method of selecting cell lines that have a transformed phenotype (are potentially tumor cells) from a population of cells (RIE-1 parentals) that are not transformed. The parental cell line, RIE-1 cells, does not have the capacity to grow in soft agar or to produce tumors in mice. Following gene-trapping, cells were screened for their capacity to grow in soft agar. These cells were cloned and genomic sequences were obtained 5' or 3' of the retrovirus vector (SEQ ID NO:76, SEQ ID NO:77, SEQ ID NO:78, SEQ ID NO:79, SEQ ID NO:80, SEQ ID NO:81, SEQ ID NO:82, SEQ ID NO:83). All of the cell lines behave as if they are tumor cell lines, as they also induce tumors in mice.

Of the cell lines, two are associated with the enhanced expression of the prostaglandin synthetase gene II or COX 2. The COX 2 gene has been found to be increased in pre-malignant adenomas in humans and overexpressed in human colon cancer. Inhibitors of COX 2 expression also arrests the growth of the tumor. One of the cell lines, x18 (SEQ ID NO:76), has disrupted a gene that is now represented in the EST (dbest) database, but the gene is not known (not present in GenBank). (SEQ ID NO:76): >02-X18H-t7 . . . , identical to: gb|W55397|W55397 mb13h04.r1 Life Tech mouse brain Mus at 1.0e-114. x18 has also been sequenced from the vector with the same EST being found. (SEQ ID NO:77): >x8_b4_2. (SEQ ID NO:78): >x7_b4. (SEQ ID NO:79): >x4-b4 . . . (SEQ ID NO:80): >x2-b4 . . . (SEQ ID NO:81): >x15-b4 . . . (SEQ ID NO:82): >x13-re . . . , reverse complement. (SEQ ID NO:83): >x12_b4 . . .

Each of the genes from which the provided nucleotide sequences is isolated represents a tumor suppressor gene. The mechanism by which the disrupted genes other than the gene comprising the nucleic acid which sequence is set forth in SEQ ID NO:76 may suppress a transformed phenotype is at present unknown. However, each one represents a tumor suppressor gene that is potentially unique, as none of the genomic sequences correspond to a known gene. The capacity to select quickly tumor suppressor genes may provide unique targets in the process of treating or preventing (potential for diagnostic testing) cancer.

Isolation of Entire Genomic Genes

An isolated nucleic acid of this invention (whose sequence is set forth in any of SEQ ID NO:1 through SEQ ID NO: 83), or a smaller fragment thereof, is labeled by a detectable label and utilized as a probe to screen a rat genomic library (lambda phage or yeast artificial chromosome vector library) under high stringency conditions, i.e., high salt and high temperatures to create hybridization and wash temperature 5–20° C. Clones are isolated and sequenced by standard Sanger dideoxynucleotide sequencing methods. Once the entire sequence of the new clone is determined, it is aligned with the probe sequence and its orientation relative to the probe sequence determined. A second and third probe is designed using sequences from either end of the combined genomic sequence, respectively. These probes are used to screen the library, isolate new clones, which are sequenced. These sequences are aligned with the previously obtained sequences and new probes designed corresponding to sequences at either end and the entire process repeated until the entire gene is isolated and mapped. When one end of the sequence cannot isolate any new clone, a new library can be screened. The complete sequence includes regulatory regions at the 5' end and a polyadenylation signal at the 3' end.

Isolation of cDNAs

An isolated nucleic acid (whose sequence is set forth in any of SEQ ID NO:1 through SEQ ID NO:83, and preferably any of SEQ ID NO:5 through SEQ ID NO:83), or a smaller fragment thereof, or additional fragments obtained from the genomic library, that contain open reading frames, is labeled by a detectable label and utilized as a probe to screen a portions of the present fragments, to screen a cDNA library. A rat cDNA library obtains rat cDNA; a human cDNA library obtains a human cDNA. Repeated screens can be utilized as described above to obtain the complete coding sequence of the gene from several clones if necessary. The isolates can then be sequenced to determine the nucleotide sequence by standard means such as dideoxynucleotide sequencing methods.

Serum Survival Factor Isolation and Characterization

The lack of tolerance to serum starvation is due to the acquired dependence of the persistently infected cells for a serum factor (survival factor) that is present in serum. The serum survival factor for persistently infected cells has a molecular weight between 50 and 100 kD and resists inactivation in low pH (pH2) and chloroform extraction. It is inactivated by boiling for 5 minutes [once fractionated from whole serum (50 to 100 kD fraction)], and in low ionic strength solution [10 to 50 mM].

The factor was isolated from serum by size fraction using centriprep molecular cut-off filters with excluding sizes of 30 and 100 kd (Millipore and Amnicon), and dialysis tubing with a molecular exclusion of 50 kd. Polyacrylamide gel electrophoresis and silver staining was used to determine that all of the resulting material was between 50 and 100 kd, confirming the validity of the initial isolation. Further purification was performed on using ion exchange chromatography, and heparin sulfate adsorption columns, followed by HPLC. Activity was determined following adjusting the pH of the serum fraction (30 to 100 kd fraction) to different pH conditions using HCl and readjusting the pH to pH 7.4 prior to assessment of biologic activity. Low ionic strength sensitivity was determined by dialyzing the fraction containing activity into low ionic strength solution for various lengths of time and readjusting ionic strength to physiologic conditions prior to determining biologic activity by dialyzing the fraction against the media. The biologic activity was maintained in the aqueous solution following chloroform extraction, indicating the factor is not a lipid. The biologic activity was lost after the 30 to 100 kd fraction was placed in a 100° C. water bath for 5 minutes.

Isolated Nucleic Acids

Tagged genomic DIAS isolated were sequenced by standard methods using Sanger dideoxynucleotide sequencing. The nucleotide sequences of these nucleic acids are set forth herein as SEQ ID NO:1 through SEQ ID NO:75 (viral infection genes) and SEQ ID NO:76 through SEQ ID NO:83 (tumor suppressor genes). The sequences were run through computer databanks in a homology search. Sequences for some of the "6b" sequences [obtained from genomic library 6, flask b] (i.e., SEQ ID NO:37, 38, 39, 42, 61, 65, 66, 69) correspond to a known gene, alpha tropomyosin, and some of the others correspond to the vacuolar-$H^+$-ATPase. These sequences are associated with both acute and persistent viral infection and the cellular genes which comprise them, i.e., alpha tropomyosin and vacuolar-$H^+$-ATPase, can be targets for drug treatments for viral infection using the methods described above. These genes can be therapy targets particularly because disruption of one or both alleles results in a viable cell.

What is claimed is:

1. An isolated nucleic acid consisting of a nucleotide sequence set forth in SEQ ID NO: 2, SEQ ID NO:8, SEQ ID NO:20, SEQ ID NO:22, SEQ ID NO:40, SEQ ID NO:41, SEQ ID NO:45, SEQ ID NO:46, SEQ ID NO:69 or SEQ ID NO:73.

2. A host cell containing the nucleic acid of claim 1.

3. The isolated nucleic acid of claim 1, wherein the nucleotide sequence is SEQ ID NO: 2.

4. The isolated nucleic acid of claim 1, wherein the nucleotide sequence is SEQ ID NO: 8.

5. The isolated nucleic acid of claim 1, wherein the nucleotide sequence is SEQ ID NO: 20.

6. The isolated nucleic acid of claim 1, wherein the nucleotide sequence is SEQ ID NO: 22.

7. The isolated nucleic acid of claim 1, wherein the nucleotide sequence is SEQ ID NO: 40.

8. The isolated nucleic acid of claim 1, wherein the nucleotide sequence is SEQ ID NO: 41.

9. The isolated nucleic acid of claim 1, wherein the nucleotide sequence is SEQ ID NO: 45.

10. The isolated nucleic acid of claim 1, wherein the nucleotide sequence is SEQ ID NO: 46.

11. The isolated nucleic acid of claim 1, wherein the nucleotide sequence is SEQ ID NO: 69.

12. The isolated nucleic acid of claim 1, wherein the nucleotide sequence is SEQ ID NO: 73.

13. A method of identifying a cellular gene necessary for viral growth in a cell and nonessential for cellular survival, comprising (a) transferring into a cell culture growing in serum-containing medium a vector encoding a selective marker gene lacking a functional promoter,
(b) selecting cells expressing the marker gene,
(c) removing serum from the culture medium,
(d) infecting the cell culture with the virus, and
(e) isolating from the surviving cells a cellular gene within which the marker gene is inserted, thereby identifying a gene necessary for viral growth in a cell and nonessential for cellular survival.

\* \* \* \* \*

SEQUENCE LISTING (1) GENERAL INFORMATION:

(iii) NUMBER OF SEQUENCES: 83

(2) INFORMATION FOR SEQ ID NO: 1:

(i) SEQUENCE CHARACTERISTICS:
        (A) LENGTH: 828 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 1:

```
AAAAAAAAAT TACCATTTTT GGGNGAACCT TTNATANTTN GTTCCTAGAG GGNGAGTCAG      60

GGGTAAAAAA AACGATNAAG GGAGTTGNGG CGATTGGAGA AGCTATTATG AAGGGATAAA     120

ANACTTAGGT TGAGCCGGCG GGTGGGGTGT ATTCTTGGGG TGGNGAAAAG NNAGATCAAC     180

ATGAGATTTT TTTGTTTTAG GTTTTGCATG TTGTAATGCA ATANTTTAAC CTGATTTTAT     240

GTGCAGGATG CCTGAGGTTT GTGAGCAGGA ACACAGGAAA AGGAACACCG GTANTCGAAC     300

ACCGGTGAGT CCGCGCAGCC GCAGAGAAGG CGGGTATCAT TCGNTCCACC CTGTATGNTA     360

ATATGGAGCG CTACGGCCCC GCCCCTGGGG CCGATGGGCC CAAAAAGGTA GGGTTCGAGA     420

AGACGTCTGC ATGGAGCAGT GGACCAGTGA AGACCCAGGC AAGGCCGAAC GTTGGGCCCC     480

GGGCCCCGGG GGCGGGTAGC AGGGCCCATA CATTGTCCAA GGGCTGCTGG AGAGCCTGGA     540

GCCTCGCTCC CCCACCGGCG CAAAGTGGTA CAGCCCATGG GGGCGTGGCC CATATCATGG     600

ACGCGAGCGC GGCCGCCATC TTGNTCTGCG GTGCTGGTAT TTAGAGCGCA GCGCCTGACT     660

GGCGGGGTCG CCTTCGCATC CGCCGCTTCG AGAATCTTCT TTCGTCTGCT CGCTCTCTCT     720

CCCGTCGTCC TAGCCCGCCG CCGCCTGCTG AGCTTGCCCT CTTCCCCGCT TGCAGACATG     780

GNGGACATTG AAAGACCCTA CCTNAAGGGC CNGCANGCNA GAAAAAGT                  828
```

(2) INFORMATION FOR SEQ ID NO: 2:

(i) SEQUENCE CHARACTERISTICS:
        (A) LENGTH: 845 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 2:

```
TCNCCTAAGA NANGAGANAG GTTAGATGGN AATGGAGANT ANATACCGGG CTTAGCTTCG      60

CCNNGGACCC ACCNAGGGGA AAAGAGCCNT CNNGCAACAA ACNAAAGGAN CGGAAAGAGG     120
```

| | | |
|---|---|---|
| AAGGGNANGN GGNNAAACAN ATTGGGCGAA TTTAAAANCT NNGNCCNGTT TGAAATAGNG | | 180 |
| CNCGGCCGNT CCNTGGGCCN GATCCANCCT TCCNTNACTT TTCNTCCCCN GCNTTAAATT | | 240 |
| GCGNCGNCGG CCCCCCCAAC CATNTNTTCC GTTTTNANCA CCNGNGGCCC CGGCAGTGCN | | 300 |
| GATGNNGGGG AATTGNNAAT GCCCCCCANC CATTTTGNNT CNGNNCCTGG GGAGAGANTN | | 360 |
| AAACGGTGNG NGNAGNNGTT AATATGGCGG CAGCGGNGAC ANCAGTAGCC AGNGCAGGCA | | 420 |
| CGCGNAGTTG GCNGGGACG CCANGTGNCN GGAGANNTGG AGCGGCGGCG GAGCGGGCNC | | 480 |
| CNAAAAAAAA AAANAANNGN TGGTAAGGGG GCCCGGGGTG GANGANATTT CNNGGGCNGC | | 540 |
| TTCTAGGNGT CANGNTGNGG CCGCTNCGTT CGGCCCTGGA TGNAGCCCNG NGCCNGTGCC | | 600 |
| NCCNCCGGGG GGAGTTTGTT TCCNTCTACC GTNCCCTGCT GNGGAGCGAC GANCTGCANT | | 660 |
| CCCCNGGAGC GTCTANNAGG CCGTGGCNAA CCCCATCNAN GCNCNCCAGT NAGCTTCCTT | | 720 |
| CNTCCCGACA TAGTAGGCGT CNGGNGGCGT TGNCGACAGN GGCCNNCGTC GATGGGANNN | | 780 |
| TCTATTTNNG NTTCATGGGC CGTATGTTAG ACCTNTCGAA GGACGCGNNA AATAGATAGG | | 840 |
| GGGGG | | 845 |

(2) INFORMATION FOR SEQ ID NO: 3:

(i) SEQUENCE CHARACTERISTICS:
        (A) LENGTH: 818 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 3:

| | | |
|---|---|---|
| TACACCTTTG NGNGTGTTGA AAATTACGGG GGANANGAAN AAAAANGTAT CCTTTTGGAN | | 60 |
| GCCCCGGNCT CTTGTGGAAT TTGTGATTTA CGGCGGNANT CATATGATTT CGGAAANAAG | | 120 |
| ATAAAGCCNN NCNNNNNGGG GTAGGGAAGA AGGATTTTGN AAACAAANTN TGGGTNTATA | | 180 |
| TAANNGTGGG GGGGGGAGNT CATTGAGGNG GGGNGGAATA TNNAATNTTT TTTTTTTNNT | | 240 |
| TNNNNGGCAA GAGGGATGAA GGTAAGGTTA GTATGAAATG GCCNNNCCAG AGAAGTTNGA | | 300 |
| TGAAAAAGAT AGTGCCACCA AGAGANATNA TTTGTTATTT TTAACAGTGG GGGGAGGTAG | | 360 |
| TTNTAGACCA CCATTTATTA NAACTGAGGC ACAAAGAAGA TGATTGGGGG GCACTTACAG | | 420 |
| AGTAAGCAGT ATTTACATAA AGATTTNTTC CCCAGGAATN ANGAGGAAGN TGGATAACTG | | 480 |
| AACAAAGCCA TGTAAGCAGG CTTTTTGGTA TGCATGTGGT CCCATTACAA GGAATACCCA | | 540 |
| ATAAATAGCA AATGCACACT GCCATTCACA AGCAATTGCA GAGAATGGGT GGGGGATGTG | | 600 |
| AAACTAAAGA GCTTTGTAGC TGCCTGAGGA GGTGGGTTCT CTATATCCGT GGGAGCTAGT | | 660 |
| GATCCCCCAC AGGTCTTAGC TGGTGCCATG ATTGTGATCT TAGGCCAGAT TTGATGTCCC | | 720 |
| CCACATGGCC GAGTCCGCCA TGGATGCAAC AGGGCAGCTT TATTTGCTGT GGGCNGGTAN | | 780 |
| TGAAGGATNT CACAAATGAA CTTGGCAAGT AGAGAGGT | | 818 |

(2) INFORMATION FOR SEQ ID NO: 4:

(i) SEQUENCE CHARACTERISTICS:
        (A) LENGTH: 857 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 4:

```
TGGAAAGANT GNGNTAAAGT TNAGTTNNNA GATATTGANN AANNTNGGGN AAAANAAGGT      60

GNNNNACAAT CTCNCAANNA TTTNAANGAA GGGGGAATAA ATGNAAANTG GGANTTAAAA     120

AAANAGGGGN NANANGNTTN NGGTTNAANA NAAGGGGGGT NTNCCCGTTT TTTTTTTAGG    180

ATCCTGGGAG TAACCNACAG GAACCNAAAA TTNGNANAAG GGNGNTCCTT CCCTTCCNGT    240

CAGTAAGGGA TGGGGCCCTA TTTTTANCAA CGAACACCAT TGACAGGANA CCGGTCAGNA    300

TTCCGTTAAG TATTTTGACC TTTCCAGGGG ATGTNTCCGC ACAGCCGTTG NGACCTTAAA    360

CGCGNCCAGA TTNTGCGAAN GTCATTTTGG GAATGACTGT TGTAGACACT GCTTTTTTAG    420

TCGCAGATNT GACCGCAGAT TTTCNTTTCC CACCTTATGT CCGNTGGAGC AGTGGTGGCC    480

GGAGAAAATT TCTTGGGGTT CCNTCCCGNG ACCCAAAGAA CACAACTGTT CTCGCTGCCC    540

GGCACCCATC GCCACGTCAG CTCACGCTCG CGACGCCAGC ACGCNTGCGC GCAGAGAAAG    600

GCGGAGCATG CGCAAAGGCC TGCNTNTAAC ATCCGGGGCT CGGGCGGCGG CGCTGCCGCC    660

GCGAGGGATT AANGGGGTCT TTCNTTTCNG TCTCTGGCCG GCTGGGCGCG GGCGACTGCT    720

GGCGAGGCGC GTGGAAGCTC GCGATAGTTC CCCTCCGCCT CCTCTTCCCG GTCCAGGCCA    780

CTAGGGAGTT CGCTGACGCC GGGTGAACTG AGCGTACCGC CTGAAAGACC CCACAAGTAG    840

GTTTGGCAAG TAGAAAG                                                   857

(2) INFORMATION FOR SEQ ID NO: 5:

(i) SEQUENCE CHARACTERISTICS:
        (A) LENGTH: 896 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 5:

GGGAGAAAGG GGCGACNTTT ATTGGTCCNG GAGNGGGGGG NCAAATGGGT TTTTATCCAN     60

TTTAACGGGG GGAGGCCCCG GNNGAGGAAT TCCCGGGGGA GGAANAAAAA CAAGATCCGC    120

NTAAGAGGGN GGGGGTNTCC GNNNTTNTTN GAATNGTGGN GCACCGGGGG GGCAAGGAAG    180

AGGGTTCCCG GAGAATGGGG NGGATAAAAN GATTGGCAAC TCACCCCGGN TAGTTGTACC    240

AGGTGTTTTT TTTTTTTTTT TTTGTTCANA AANAGGAAAA TGATTCAAGT TAAAAAAGTA    300

ATTGGCAAGG AAATTTTTTT CCTANCCTCC TTGAAAAATA GTGGGAACAG GGGTTCCCAA    360

GGGGAAAGGT CCCCNATTNA ACAAAATGNG TTTCAGNGGA GTGTGGCCCA CCCATTGTGT    420

NTCCATGGAA GAGTGGCTTT TNTGGNGAAG TTCATTTTCC TTAACCTTNA NNACTGTAAN    480

GGNTCTTGTG CTTGAGAATA TTGTTGGCCA GCTTTATNGT CTTCATTTNT AANACTATTT    540

AGACTAGAGT GTTNTAGATT NTAGGTCTTC ANGTTTCCAG TCACCAGTCC TTGGCTTTTT    600

AGTATGGAAA TCACCAGTAA TGGCAATATA ACATCCCTGC TTCTGTTTCT TAGAAGGCTN    660

NATTACAGTG TGTTCAAACT CCGTGTCATT GCAACAGGTT AAACTAACTT TNTACGTAGG    720

ACATCAGGGT ATTGACATTC TCATCCTAAA GTCAGTTTGT CTGTTTCCAG AGGAGGAACT    780

GAAGCAGTGG TTCTTTAAGT AACTGACTCA GGGCTTTCCT GCCTGGCGCG CCTGCCAGGC    840

ATNGTGTAGC ATTGTACTGC ATCTTCTTTG ACCAGTTTCC CCAGGTGAAG AGCCTG        896

(2) INFORMATION FOR SEQ ID NO: 6:

(i) SEQUENCE CHARACTERISTICS:
        (A) LENGTH: 937 base pairs
```

(B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO: 6:

```
GGGCCCCCCC CCCCCNANTT AATTTTNGGG AAGAAAAAAG GGAAAAAANT TTGGGGTCAG      60

GAAAAANGAA GTTGGNAANC GNNGGGGNGN CAGNATTNGA ANAGTGGGGG ANNTTAATTT     120

NAGAGGTCCC TTNNTTCCNN GGAAAAGTTT AAAAGGGGTT CAATTAACTT NGGATCNCCA     180

TTTATCAGAT TACCCGNGNG TCACCTGGGG ACCCTTTACN GGTGGCGGGA CATTNGAAAN     240

ACATATTAGT CAGATTATAC ATAGCAAANA TAGTTAGGAG CACAANGAAT CATTTATGGT     300

GGNGGTCACC ACACAGGAGA TGTATTATCC GCAGTATTAG AGAGTTGAGA ACCATATNTT     360

AGAGATGCGG TAGACTGACT GTTCCCTTTT CGNTTGGAGT GACCTTGCCA TTAGAGGCAA     420

CAGCATCAGT ATTGTTCCCA GTCCCCNTCA CACTGATTCG AACTTTAAGG ACACTGATCT     480

NTGGCTGGTA GAGGTTCAGC ACACATACCA GAGTTACGAG TCACGTGCCA GAAGGGCAAA     540

CTGAACACGG AATTAGAGGG AACTCGATGT CTCCGGCTTG CACTGGTCTT CTCTTGCANT     600

AGAATCCTTC ATCCTGCTCC CAGTCCGGAC GTCCAGGCAA CAAGGGCGTG GAAAGTGAGG     660

GGGCTGGGAG GTGTGTTTGC CTTGCCTCAG GCGNTGGGTG GGGTTGGGGC GTGCCAGCAC     720

TCCCCTGGGC GGGCNTCACC GATGCTGGCC ACTATAAGGC CAGCCAGACT GCGACACAGT     780

CCATCCCCTC GACCACTCTT TTGGCGCTTC ATTGTCGACG TGTGGTGAGC TCTCACTGGG     840

GCGTCCCTCT AAGATCTGTC CACTNCCTGG TCTAGGGGTT AAGCNTTTTC CTGCCCTGAA     900

AGACCCCACA ATGTAGNTTT GGCAAGCTAG CAAAGGT                             937
```

(2) INFORMATION FOR SEQ ID NO: 7:

(i) SEQUENCE CHARACTERISTICS:
        (A) LENGTH: 888 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 7:

```
AAAAGGGGGC CCCAGCGGNG GGGGGTTGTC CAAGGAATCA AAANGTGGGG NGGGGGGGAA      60

AAAANTACTT TTAAAAAAGG CNGCCNNANA ATANANGACG TTCNGGGGNG TTTGAAAAAA     120

GGCCGGAAGC CTCGGACNGG TTTCNNTGTT AGGACAAGGA AAAAGGGNAC GCACNGGGAT     180

TTCCTTTCCT TATNTTAGCA AATNGCCGGC CAGGAAACCA NCGAGTTGGG NGGGNTTNGG     240

TTTTCNGTNA AAGGAAAGCA GGGGGGGGAN AAACACGGAN AAAAAGGGAA GAANNGGGTT     300

NATTNNGGTT AGNAATTGGN TCCCAGAGAG NGCCAAGAAA ATNGGCCTGT CCAAAATTCT     360

TTTTCCCNGC TTTTAAGACA GGCANGATAN TATNNGGCAG CAGGTNATTA CCANAGGTAA     420

GTAAATTACA ATGGGTAAGG GCTTGGCACA GGCCAGGGTA AGTAGGGCAN GTATGGATGT     480

TAAACATTAC CCTTCATCCN GAGGNAGTTA ACACAAGCAT TCNTGGCGGG TCTCACATAT     540

CCCAAANAAA AATNTTCAAA AGNAGCCCCN TGGGAACGT TAAGCCAAGC NTANGACTCA     600

CAAGGGANGA CATGGGCAGG NTAGGGNACA GAATCAGTGN TCAGAGACTC CAGGGGCACC     660

CCTGATTCCN TTTGNTGTCA CACAGACANT GCTCCAGGGA CAACCTTCCC GGANGTGAGT     720

ATANGACTTT CCTGATGGNG ACGCTGCCGT GANGGGACAC TNCCTCGTGG TAGCACACAT     780
```

| TCCTCAGTCA GCTTCTGAGC CTCAGGGTCC CAGCAGGCAC AGTGGCAANG ACCTCATTCT | 840 |
| TCTCGTCTGT CCCACTGAAA GACNNTCACN AAGGAGCTGG CTAGTAGA | 888 |

(2) INFORMATION FOR SEQ ID NO: 8:

(i) SEQUENCE CHARACTERISTICS:
        (A) LENGTH: 980 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 8:

| AGAAATGAAA AAGAAGGAAA GCTAAAAATA GATTATAAGT GTTCTATTTG AAAAAAGAAA | 60 |
| GAAAAAAAG AAAAAGAACA CAGAGAAGAA TAAAGGAGAA GAAAAAGGAA GAGAAAAAAA | 120 |
| AGAAAGAAAA AACGGAAAAG AAACCTAGAA AATAAAAAAA CAAAGTATCC GATAAGGAAG | 180 |
| AGAAAGGAGA AAGACTTACC TAGAGCCCAG AAATAGAGAA ACTAGAACAA AAAATGGAGA | 240 |
| AGAGAGGAG AGAAAAAGGA TTAGAGAGGG TGAGGTAGAA GGAAGAAAAG ACAAGAAAGC | 300 |
| AGAAAAAAAC TAACAAAGAT GCATATAAAC AGAGAGAAGA TGATTAAGAT TAGAGAAAAA | 360 |
| GACCAAAGAG AGAAGGTAGA CAGGACAAAT AAAACAAAAA CAGGAGGGGA GAAGGGGAAA | 420 |
| GAAGAAAGAG GGCAAAAGCA AAGGAATAAG ATAATAGCAC CAATAGCAGG ACAGTAAAGG | 480 |
| GTAGAGAAGG GACCATTCCC TACCCCATAG GGGGGAACGA CCCCGGAATC AAAATACAAG | 540 |
| GCACCGAGCT GAACCTGGTT ATCACACAGG CAGGAGTGGT ATAGCACGGC GTTCCGGGCA | 600 |
| AAAAAAAAAA TGAAAAATAA ATTCCTTCGG GCGGAGAACT AGAAGAGGAT GGGAACTCCT | 660 |
| TGACAGAAGT AGCAGGCAGG AAGCCAGCCA GCACCCCAGC CCAAACAGAA GCAGCCGCAA | 720 |
| TGAAACGGGC GGCAGATCCA CATCCGCAAA GTCCTCAAGG GAGCATCGGC GAGGCCCGGA | 780 |
| GCCAATGAGG AAGGGCAGGA AACCATATCA AGCCGAGCGT CGGGACGGCT GCCATGAGAC | 840 |
| ACCCGGAGAG GTAATTTTTT TTTTACGGGA AGCGTCCAGC CAAGTTAGTG GGCCGGAAGC | 900 |
| GACGGTACTT TAGTATACAT CGTTTTGCCC GAGTGGTCAG ATTCTTTTGT TATCCCCAAC | 960 |
| AGAACCGTAA GCTAGAAATA | 980 |

(2) INFORMATION FOR SEQ ID NO: 9:

(i) SEQUENCE CHARACTERISTICS:
        (A) LENGTH: 845 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 9:

| TCNCCTAAGA NANGAGANAG GTTAGATGGN AATGGAGANT ANATACCGGG CTTAGCTTCG | 60 |
| CCNNGGACCC ACCNAGGGGA AAAGAGCCNT CNNGCAACAA ACNAAAGGAN CGGAAAGAGG | 120 |
| AAGGGNANGN GGNNAAAACAN ATTGGGCGAA TTTAAAANCT NNGNCCNGTT TGAAATAGNG | 180 |
| CNCGGCCGNT CCNTGGGCCN GATCCANCCT TCCNTNACTT TTCNTCCCCN GCNTTAAATT | 240 |
| GCGNCGNCGG CCCCCCCAAC CATNTNTTCC GTTTTNANCA CCNGNGGCCC CGGCAGTGCN | 300 |
| GATGNNGGGG AATTGNNAAT GCCCCCCANC CATTTTGNNT CNGNNCCTGG GGAGAGANTN | 360 |
| AAACGGTGNG NGNAGNNGTT AATATGGCGG CAGCGGNGAC ANCAGTAGCC AGNGCAGGCA | 420 |
| CGCGNAGTTG GCNGGGGACG CCANGTGNCN GGAGANNTGG AGCGGCGGCG GAGCGGGCNC | 480 |

| | | | | |
|---|---|---|---|---|
| CNAAAAAAAA | AAANAANNGN | TGGTAAGGGG | GCCCGGGGTG | GANGANATTT | CNNGGGCNGC | 540 |
| TTCTAGGNGT | CANGNTGNGG | CCGCTNCGTT | CGGCCCTGGA | TGNAGCCCNG | NGCCNGTGCC | 600 |
| NCCNCCGGGG | GGAGTTTGTT | TCCNTCTACC | GTNCCCTGCT | GNGGAGCGAC | GANCTGCANT | 660 |
| CCCCNGGAGC | GTCTANNAGG | CCGTGGCNAA | CCCCATCNAN | GCNCNCCAGT | NAGCTTCCTT | 720 |
| CNTCCCGACA | TAGTAGGCGT | CNGGNGGCGT | TGNCGACAGN | GGCCNNCGTC | GATGGGANNN | 780 |
| TCTATTTNNG | NTTCATGGGC | CGTATGTTAG | ACCTNTCGAA | GGACGCGNNA | AATAGATAGG | 840 |
| GGGGG | | | | | 845 |

(2) INFORMATION FOR SEQ ID NO: 10:

(i) SEQUENCE CHARACTERISTICS:
        (A) LENGTH: 528 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 10:

| | | | | | |
|---|---|---|---|---|---|
| GGATTTNNTA | ACCTTTCNGG | GAAGGGNGNG | GAAAAGGNGC | CAAACAAAAA | GACCCCNNTG | 60 |
| CCCGGAAATN | CTTGGGGGNN | ATTGNGGAGC | GTTTTTTANN | GGGGATTGGG | GGGNTNGGGN | 120 |
| TGCNCCCNNA | TATTCCCGGC | TNAGGGGCAA | CCCGAGGGGT | NNTNTCCGAC | CATGTAACTT | 180 |
| GTTTCGGAAT | GAGGGGGAAT | GCNNATTNTG | ANTATTGAAN | NGNGACCCGG | NGGGGNCNTG | 240 |
| TTNNAATTAA | CCTNNTACCC | GGAATTTCNG | CGAGANCGNG | ANGATNNCTG | GCACTTNTTC | 300 |
| CGTATTACGN | GTGGCGTTCN | NGANTGCAGG | GGNTGCCCTT | GTTTGNNTTT | CTGAGGGTTT | 360 |
| CTTATANGCA | GATTGTGGGG | TTGGAAACGA | GANATCCCTN | ANGTAATGCC | ANNTCACACG | 420 |
| GGATGGAGCA | GGAACNCCCT | ACGNATAGTT | NACCTTCANT | CAGGGTGGGG | AANCGATNGA | 480 |
| CCNGAGGTAT | ATGGGCNGAA | CNGGACATGT | NGGGNNANCC | GTTCAATC | | 528 |

(2) INFORMATION FOR SEQ ID NO: 11:

(i) SEQUENCE CHARACTERISTICS:
        (A) LENGTH: 927 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 11:

| | | | | | |
|---|---|---|---|---|---|
| AANACGGTTT | AATAAGGGGG | ATGTTCAAAA | CNCCACTCCG | GGGGAANAAA | ANAAAAAATT | 60 |
| AGGGGGGGAG | AANGGATTGG | NGTATAGTTT | CCCACCACAA | ACCTNGTTCC | ATTTTTTCGG | 120 |
| GGGGGNAACG | GAGGNCATGA | TTATGGGGTG | AAGGCAGCAC | CCACCCATTT | TTCGGGGGNA | 180 |
| AGTCAGTTTT | TTTTGGTANA | ATCAAAGTTC | CTTCGAACAT | NTCGTTTTAT | CCAAGGAGTT | 240 |
| TTGGTGTTAA | ATTAGCANTT | TNTGNGAGTT | TCAAAGTTNT | GGTTCCNGAG | NAGNTTTGTA | 300 |
| ATTGGTTCAC | CGGTTNTTTT | GNGCCAGGAA | AGCAGACCCN | TGTTNGGAGG | GGAGATTCCN | 360 |
| ATTTTTAGTT | CCCATTTGGT | GTTTCCNTAG | GTAATGGAGT | CTGCAGACAG | TTTGAGTNTA | 420 |
| NTGAGTTGAG | TCCCTTNTCC | TATCAGCCGG | GGTGGCATTC | TGTCCAAAGG | AGGAATCCAG | 480 |
| CAGCCAGATT | AGATTTCAGT | NTCNTTTNTA | ACAGGGAAGT | TAGACACACC | CGGCCAGNTT | 540 |
| GCAGCCTTTC | CACCCCCAAN | GAGTGAACCC | TGCCNTTTCA | GCTTTTACCC | AATTTACTTT | 600 |

```
CGTTGGCTTA GCATGCAGAT TNTTTGGCTC CATGCCCGGA GCAGCTGACA TGGGAGGCTT    660

TGAAACTTCC ATTATCATAG AATGGCAGGC AGGTCCTTTG CGGTTAAAAC CAGGAGCCTG    720

GGCCNAATGA GATGGNTCAN TGAGCAAAGG CGNTTACTGC CAACCCTGAT GCCTTCAGTT    780

TAGTNTTGGA ATTCACAGGG TAGAAGTTGA ANACNTTTGA CTCTTCAAAA GTTGTCCCTG    840

TAGCAGGGCA GNNGTGGTGC ATNCCTTTAA TTTGGGCTAC TTTGTGAAAG ATATCCACAA    900

NGAACCTTGG CAAGTAGAGG ANGTCGT                                       927

(2) INFORMATION FOR SEQ ID NO: 12:

(i) SEQUENCE CHARACTERISTICS:
        (A) LENGTH: 911 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 12:

GGGAGTTTGC TCTCAGAGNG CCNATTACGC NACAGGGGGN GTCTCACANT ATAANCTCAT     60

ATANNATACT CTACNNTNCC CCCCCTNANG TNTCAAGGGC AAGAGAATAT NNTCTCTCTC    120

NTATCGTCTN GGGGNNTCTN AAATGTTTGN GCTCCCCGGG NAAAATANNT CTCTNTCNCG    180

NCTCTATNTT CTCNCCTCAC ATATNTGCGN ACTCTTTCTC NNCCACANNA AAAGCGCCCA    240

GTGNGGGGAN CTCNNAGAGT GTATNGNGAA GAACTGNNAG TGTNTNTGGG GCGCGTTCTC    300

GGGGAGANNA TACNCTTCTC TCNTCTCTCT NTAGAGTGNG ATGTANAAAA CCNCANNTGT    360

TGCANAGANA AATGGGGCTC NGAGNCTCTT ATATTTCCCC NCCCCTCTCN CCATATATNA    420

CCTNCGGGGG CTTNTNTNTA AATCNCCTNT CNCCATTNTT NNNANNNGCG TGTTTNTATT    480

GTNNGTNTCC NCNTGNTCCA AAAATCTCAA ATTTGTGTCT CTTNTCCCAA ACNCTATNTC    540

TCCCNTANCC CTGGGGGNGT NTATTATNTN TNTNTATATN CNTATNTTAT ATACNTATAN    600

TNTATNTNNT ATATATTTGG GGTCNTTACC AAAACCCCNT TTTTNTCTCA CTTTTCNTCN    660

ACTCCCTTCC CGGGGCCTNG AAANTTTATT NCCNNCCNTT NNGNTCCTTT TCTNTTAAAT    720

TCNTTNCNTN NGGAAAACCC TTTTCNAAAC NGGNTTTCCC CTTTTNNCNT CCCNCTCAAA    780

CCCCCCAAAT TNGGGCATTT TTTCTTTTCC CCTCACCNAA CCCCNTTTNC CTCCCCCCNC    840

CCCCCCCAAA NTGNGAATAC CCTGNTTTTC AGNGGNNNNG AAAAATCCCT CCCCGANGGN    900

GCCCCCCTCC T                                                        911

(2) INFORMATION FOR SEQ ID NO: 13:

(i) SEQUENCE CHARACTERISTICS:
        (A) LENGTH: 880 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 13:

GGGCACCAAC GGNGGAAGAG TTTTCCANGG TANAAGAAAG NAGGANTGGG NCGANAANAA     60

TTANTTTTNA AAAAGGNCAC CAGATANAAA AAACTTTTNA GGGGNGTTAA NAAAAANGCN    120

GAAACCCTCN GACGGTTTTC NNGANTNTTA AANAGATTCA GGGGAAGCAC GAGATTATCT    180

TTTCNTTTTT GAGCAAATTG CCAGCAGGGA ACNGACNAGA GGNTNGGTTT TTGNATNCNN    240

TTAAACGTAA CGCAGNTTTG GANAAACACA GNTNACATGG AAAGACCTGG GNNATTAGGG    300
```

```
TAANGNAAGN GGTTCAAGAG AGAGCCGATG AAATNGCCNG GTCCAAAATC TTTTTCCTTG      360

NCTTTAANAC AGGTNNNAAA AATNNGGCTG CTGTTTATAA CNATAGNTAA GTGAANNACA      420

ANGGGTAAGT GNTTGGCACA GNCCAGGGTA AGTAGGCATN NAAGGAATGT TAAACATNAC      480

CNTTGATCGN GNGGTTGTTT ACACCGCNTT AAAGAAANGT TTAAAAATAT CCCTGGGCTG      540

TTTCTTCCTN GGTGCCNCAN GGNGAACGAC AAGCCAAGCG NATGANTCAC AGGAGACGAC      600

ATGGGCAGGT TGGGTACAGA ATCAGTGTTC AGAGACTCCA GGGGCACCCA GATTCCNTCA      660

GNCTGTCACA CAGACACTGC TCCCAGGGAC AACCCTCCGG GATGTGAGGN NANGACTTCC      720

GNGNNGGAGA CGCTNCAGNG ANGGGACACT CCTGGTGGTA GCACACATTC TTCAGTCNGA      780

TTNTGAGCNT CTGGTCCCNG CAGAGNACAG TGGNAATGAC TTTTTTCTTA CTTGNGNCTC      840

CAAGGGCGTC TCCACAAGAC AGCGTGNCNA GTAGATAAGT                          880

(2) INFORMATION FOR SEQ ID NO: 14:

(i) SEQUENCE CHARACTERISTICS:
        (A) LENGTH: 923 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 14:

GGGAGGAGTA CNGGANGGGT CCGACGTAAN TNTNTCACAG GNAAGNCGAN ANGAGGAGGG       60

GTNGCGTAGG NNACAAAGAG ATAGGAACGG GGNCGNNAAC NTNNCNTNTN GAAAAGGCCG      120

CCANNGTNAA NCAACTNTGG CGGGGGTGGG ACNNAAGGCG NGNGGCNNNA GAAGGTTTNN      180

TTNNTTGNAA CCNAGATTCG AGGGACGGAC NGGANTATCN TATCCNTNTT NGTTNCGANT      240

GCCNGCGNGN ATCNGGCNAG GGAGGGTNGG TTNNNNGGTT TCNGGNGACN NCCCCAGTTT      300

NTGGNNNATA CCCNGCTCTC ACANGNNGGA CGNGGGTNTT TNNGGTGAGG AAGNNGCNTC      360

CCCGCGAGAG CCCGNGGNAA GGGCGNGTCC AAAANTCTTN TTCCCTGCTT NTNCNACAGG      420

CTNNGANANN ATNNGGCTGN TGTTNATCNC NATAGGTAGN TCAACCNNCA NGGGGANGTG      480

CTNNCACACC CCAGGTTAGT GTCCCNTNCA NGGTATGTTA ANACGTTACC NNTGATCGGG      540

GGTTNTTTAC NNAAAANNAA AAAAAAANTC ACCNTCCCGG GCNTGNTGNT TCCTNGGGGC      600

CCCANGGTGA ACGACNANCC AANCTNTTGA NTNACAAGGG ACGACGTGNG CAGGTTGNCG      660

TNCNGAGTCA GTGTTCAGAG ANTTCNGGGG CACCCCTGAT TCCCNCGGNN GTNACACAGA      720

NACTGNTCCA GGNNCNNCCC TCCGGTTGNG AGTCNAAGAC TTCNGGNNGG TGACNCTACN      780

GTGANNGGAC ACTTCGTGGN GGTGNCNCAC ATTCGTCGGT CGGCTTANGA NCNTCTNGGT      840

CCCNGCGAGA CACTNTNGCA ATGNCTTTNT TTGTTCTGGG GCTTCCNAAT GGGTCCTCCC      900

AAAAGNCNGC TTTAGCTGTA ATA                                            923

(2) INFORMATION FOR SEQ ID NO: 15:

(i) SEQUENCE CHARACTERISTICS:
        (A) LENGTH: 880 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 15:
```

```
ANANAGAGTA ANTAANANAA GAGGAAGAGA NAAGAAAGNA GAAGGNAAGG ANANAAANGG        60

GNNGGCGAGG AAAAAAGGAA AGGAGAANAA TAAAAGAAAA AGTGAGGAAG GAAGGAGTAN       120

NAGAAAAAAG NAAAGNGGAG ATAGNAGAAA GGNCCGGNGG ANAAAAGANT AGATTAANGA       180

NAGNTGAAAG AATAAAGANN ANGGCGANAA GGAAAGAAGA NCGAGNATTA GAAANAAGAG       240

AGGAAAGANN NGGGGGGAGG GAANGAGGCG AANTCNNGAG ANCAGTNNAN AAGGCAAGAG       300

AATNAGGAGN AGANANGAAG NNNANGANGA AGGAGGGGAA AGAGGGNACA GAAAAAACAA       360

GTANAGTAAC CNACNNCNGC GAGNGNGCCA AATAGGTNGC GCCAGCNACA NGGCCCGAGC       420

CCNGGGCGAG GGGGCATCAN GAGCCAAGGG GAGCGGGTCC AGNCNTAGTT NTGAAAGGAA       480

AGGGGAGGNG GGNAGATATT ATATGGTCGN GCCCCCCCCN GTGTCTCGGT GAAAAAAAAA      540

AGGNGTGANN AGCAGGGCCN TNTTGGNTGN GGGATCGNGC ATGATCAGAG ACCNGAGGCC      600

GGACNTTCCG CNGNGCCTTC CGTAGGCCCA NTGTCAAATG TATTCAAGCC GGTTNGAAGG      660

ATGCCGGNGN TAGNGANTGA TGCGGGGGCC NGCCCCCCCG GNTTTCCGCC CCCGCAGCCN      720

CNGTGGCCGC CATNACGGAG TTCCCAGTGG TGAGNGTGCG GAGNTGAGGC CCCGCGGGTC      780

GCCGCCGGTC CCCGCAGACA GGAACGCGGA GCGNNCCCTG CGCTNGAACG TANGGGNCCA      840

CTTGAAAGAC TNNACNAAAN GACGCNGATT TGTAGAAAAG                           880

(2) INFORMATION FOR SEQ ID NO: 16:

(i) SEQUENCE CHARACTERISTICS:
        (A) LENGTH: 166 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 16:

ATTCTTCAGC TTTTGCNTAG AGGAAAAAGA ATGGATTGTT TCTAGGACAA CCTGCTGAGG       60

TGCTCACCNA GNGTTCTCTC TCTCTCTCTC TCTCTCTCTC TCTCTCTCTC TCTCTCTCTC      120

TNTGNCTCTC TCCTGAANNT CCCCANAGGN NCTTNGCAGN AAAANG                    166

(2) INFORMATION FOR SEQ ID NO: 17:

(i) SEQUENCE CHARACTERISTICS:
        (A) LENGTH: 162 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 17:

CNTTTTNCTG CNAAGNNCCT NTGGGGANNT TCAGGAGAGA GNCANAGAGA GAGAGAGAGA       60

GAGAGAGA GAGAGAGAGA GAGAGAGAGA GAACNCTNGG TGAGCACCTC AGCAGGTTGT       120

CCTAGAAACA ATCCATTCTT TTTCCTCTAN GCAAAAGCTG AA                        162

(2) INFORMATION FOR SEQ ID NO: 18:

(i) SEQUENCE CHARACTERISTICS:
        (A) LENGTH: 871 base pairs
        (B) TYPE: nucleic acid
        (C) STRANDEDNESS: double
        (D) TOPOLOGY: linear (ii) MOLECULE TYPE: DNA (genomic)
```

-continued (xi) SEQUENCE DESCRIPTION: SEQ ID NO: 18:

| | |
|---|---|
| GAATAAAACC CCAGAAAGGT TTTAAAACAT TCCGTATAGA AGTTGATNAA TTNAAATAAT | 60 |
| TGGAGGTGAA ATACACAGAG GGTTTTTCAA TTAATCAATA AAAAAATAAA TTACNTACNT | 120 |
| NTTTTGGGGG GTTTTATGNA NAAANGAATT GGAGGGATCA ATTTGCAAGA AATTTATTTT | 180 |
| TTNGTATTAT TTAAAAACCG TTANGGATTC NGTTGATTTT AAATCAAGCA GTAAATATAT | 240 |
| TAAAAGGTAG GAGAATGGTA TCAATAGGCC AAGATAACAG AGTGTAAAAG TTAAAAGTAT | 300 |
| TGGACAGAAA TATTAAGAGT TATTGTTAAG ATCCNGGACT TTGGAAAATT TAAAACCAAG | 360 |
| CGATTTAGGC CAAGTTATTT CCACAGTATG GTATCAGAAG GAGTAAAGAG ACAGCACAGG | 420 |
| TGCAGATNTG ACGGCTTGGT TCCTTAGGTT ATTGCCACAG CAACGGTCTT GGCCGCAAGG | 480 |
| CAGGCTTGGG CCCAGCATGA GAAGAGAGGG GGAACCAAGT TCTTCAGGGA CCNGACGGGC | 540 |
| GGCGCCGGTG AGAAAGGACT TCATCTTGCC ATGNTCANTC AGCGAAACTG CAAACGCTTN | 600 |
| TGGCAGAGAC AACGCCAGAT CTGCAGAGGC ATTCCGGCCT TTAACCGCTT TCCCACAGTC | 660 |
| GGCCCACAGG CCTTACCGCA GCAGAAAGCG CGCGACCCGG AGGTCCCGCC AGTCAAAAGA | 720 |
| AAAAGGGGGG CGCAAAACCA TATAAGGCNT GGAGCAGGCG GCCCGGCCCC GCCCCCAGGA | 780 |
| CATGGGCCCG GCCCCAATCA TGCCCCGCCC CCAGGATTCG GTCCCGCCTC CTCCCGCTCC | 840 |
| CGGGATGGGC CGTTATGCTC CCGATACGCA T | 871 |

(2) INFORMATION FOR SEQ ID NO: 19:

(i) SEQUENCE CHARACTERISTICS:
        (A) LENGTH: 936 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 19:

| | |
|---|---|
| TGGGATTCAA AAATTGGAAG TTANTTTTTN AGGAAATTTN TTTTTAAAAT TNTAATTGGG | 60 |
| GGGNNTNGCC ACCAATTAAA ANGNGTTTGA ATTNAAAANG ATTGCCGGGG GAAAAANCCA | 120 |
| TTTNCTGCAN GGAATTAACC AAGTAATTTG GNTTGGNAGC ACTNGTTTTG GGCCTNTAAA | 180 |
| AGGCATTTTA AANACAAATT AACAGGGCNG GCATNTTCAA CGGGNGNTAG NTTGTTTTNA | 240 |
| TGAAACNGAG GNTTTTGGGG GCGGGCCTTT CCNATTNGTT TCCTTTTTTA GGATTAACAG | 300 |
| ATGNGAAAAA AAATNATGGT TTTATATCAT CGTTNTTGGC ATCAGCAGAT TGGCNATTCA | 360 |
| ATTAAAACAG ATCATTCATG ATNGGCTTTT TGGCCATTAC CATGNAAACA CAAAGAGCCA | 420 |
| GGGTTTGATT GCCCTGACCC GCCNACCTTC GGTTGCTTAG GTGAGGTGCA GCACTGCGTT | 480 |
| TTTCCTTTTC GGACTGAAAA CAGGCGAATG AATCATTTCN GTCGTGTCTT GAGGGTGCAT | 540 |
| TTTTNACATT TTTGTGCCNT GCTGTGCGCC GGTGTGTGAT TTCCCTGTTT TAAGTGGCCC | 600 |
| CTGAGGATAA CAGTGAAGTG CTGTCTAGCA TTCTTCTGCG CAGGAAGGCG GAGATCTGCC | 660 |
| CTGCGGAGAA AGTATGCGTG CTGGATAAGC ATTACTGAGC ATGACACAGA GCACCGTTGA | 720 |
| CCCCGAGTGC AGCGTTAGTG AACCGGCCAA TGTGCTGGGG GATTTTAAAT GGAATCACAC | 780 |
| AGAAGCTGAG GCTGAGGATT GATCTGTGAG TAACAAGTTG TGAATGAGGC TGGCAGGAGC | 840 |
| TAGCCTGGGA GTAAGATTCA GTGTTTGNTA ACAGCGTGCA GGCATTAAGC CAGGGAACTG | 900 |
| AAAGTNCCCA CANNGNCTTT GGCAAGTAAG AAGTCG | 936 |

(2) INFORMATION FOR SEQ ID NO: 20:

(i) SEQUENCE CHARACTERISTICS:
    (A) LENGTH: 888 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO: 20:

```
AGGNNGGGGG GGGAAACTTN TTTATNTGGA AAANTTTTGT TTNGGCGGGN AAGGAGTTTT      60

TAANAANGTT AANGGAAAAA GCTTTTANTT AANATGACCT TTTTGGGGGA AANACAAANT     120

TGGTNNGTGT ATTNGNGAAA AAGATTTATT ATAAGATTTT TTATAANATT TTNGGGGGGG     180

AAATATTTCA AANAAAATTC TGTAACAAAA GGNTTTTTGT TTTTTGTTNT CCAAGNAGTT     240

NTCCAGGTAG TTNTCAACAA CNNANGCCNT AGGGAAGGAC ATCATATGGA TATTTTCANA     300

GATTTGTTTT TAGGAAACAT TNTAAAGTCA AGGTTAAGAT GACAGTCAAN TCCCANGAGN     360

GNGGTAACTG TNTGCTTCTT TATTTAAAAT TCAATATTCA GGATTTCATT TATACTAACA     420

AGANTAATTA CCATCTTAAT GAAACATAAT TTGAATAATT TGCAAACAAT NTGATTTTTC     480

TTGAATATAC ATGTTACTAA AATATTANGG ATGCAAATAG NTAATAAACA AATAGATANG     540

NAACCATGGN ACACCCCTTC TGTGATTGGN GGGACNTGGG CATAAGGCTT GTTTGTATAA     600

TAATGTTCAT ATTTTACATT CTTCCTNNGA GGANGGTCCT CCCTGTTAAG AAAANGACTC     660

CAGGATAAGG AGACAGCACC AGTNTAGGAA GTGAGGNTCT GTTTAATGTC TTAGCAAAGT     720

AGTAAATGNT GGGACCATCA GAATAGCCCN TAAGGNTGTG GANAGAACTC TAAAAGCNTG     780

ATATATATAT ATATATATAT ATATATATAT ATATATATAT ATATATNTAT ATAAAGAGGC     840

AGTATTGAAA GACNTNCACC AATNGAGCTG GCNAGCTAGA AGAGGTCG                 888
```

(2) INFORMATION FOR SEQ ID NO: 21:

(i) SEQUENCE CHARACTERISTICS:
        (A) LENGTH: 903 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 21:

```
CTTGGAAGGT TTTTTTNNCA AAANCCNGGG NGGGTTTTTT TTAANAAANA GGNGAAAAGA      60

TTTGGAAACT TTTTTTTTTG GTTGAAGTTA NTTGGGGATT GGGGGAAAAA TTAAAAGGAT     120

TCAAAGTTCC CATGGNTTGG AAGTANAACT TTTATTCAGA AGNGAAAGTT TTAATAATGA     180

AANATGTTTT TTTGGATTNA CGGNGGNGGA ATTGGGGAGN GGAGAGAGAA GAGAGAGAGA     240

GAGGGAGAGA GAGCCGGATC CGCANTCGGG GGTTTCTACC GGCAGAGCCA GGACGGAGAG     300

GGTTTTCGGC AGCCGCNGCG GGTTCGGAGN TTTTAAGGTT TNTTAATCTT GGAAGGTGTC     360

TGANATNACC CCGTTTCTTG TCGGTGATGT TTNGTACAAG CTTTCATTTC TTCAGGATTT     420

CGGAGCGCCA ATTACTGCCC CGATNTGGTG TTTATGTTTG CCCGTTCNTG CGCNTGGCCC     480

CGCGCCCGCC CGNGAGCTGC GTTTTCCCTG GCCGCGCGGC CCGAGGGGGT GGGTGGGGGG     540

CCTTGGCCCG CGCACCCCAG CGCAAGGGAG GGGTCCCCTT CATTTTTTTT CATTGACTTC     600

AGCACCATGT GATCAGGAAG TCTGGCTCCN TCCATTTCCC NTCCCGACTG AAGGGAAACA     660

TTGTGTAGCA GCCCGCCGCG GCCACTGGTG GGATGGCNTT CGCTGGCCTG ANGTAGGGGG     720

ATAAAAATAA CCGGCATATT TAAGGCCGGA GCAGGAATCC CGGCGCTCAC ACGCGGCCTG     780
```

```
GTCAGTTCCC GAAGCCGCCA GCAGCGCTCT GCGCAGCGAG CTGCTGCTGC GCCAGCCAGN      840

TCGGGAGTGC GGACACCGTG AAAGACCTTC ACCTATAGNG CNTGGCAAGC TAGAAGAGGT      900

CGT                                                                   903
```

(2) INFORMATION FOR SEQ ID NO: 22:

(i) SEQUENCE CHARACTERISTICS:
        (A) LENGTH: 918 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 22:

```
TCGGGGGCAG GAAAANTTTG GGGTTTTCGN AAAAAAAAAA ANGGGCANAA ACCCGGTNAA       60

CNTATTNGTT TTNGGCCCNG AAAGTAAANA ATTTTTTTTT NAAAANATGG AAAAATTGAA      120

AAGGGANANG CAGGGAAGGG NGGNATTTTA TNTCCAANTT TCNGGTTCCT ACTTTTTTCC      180

NGATTCTGTC AGTTTCGCTT TAAGCAAAGG NGANGAAGGG NNAGTTTCAG AAGTTAGGCT      240

TGCCTGAGAA AATTTCAATG GGTGGCAATT CTTAGGACTC AGGACAGGAT TCAGNGNGGA      300

CTAATNTGCA TTTNGGGATN TGTCCCTGGG GTCCNTAAGN TCCGGACCGG GANAGATGTT      360

CNAGGGGGAG ACCCAANTAA CCCAAAGGAC TGAAATTATC ATGGCAGCNA CNNACCAGTA      420

GTTGNTCTGG TAATAGAGCA GATTGCTCAN AAACACGGTT GTTCCATTTG GATATATCCN      480

TGAAGTCCGG CCGTGCGAAA CGATCAGAGC CCGGGAAGAA ATCATCCCAG GCACGGAGCG      540

GGGCAAGGTT TAACGTCCAT GTTCTTTTGC TTGGCGAGCT TCGCCTTCGG AATCCGGAGG      600

CGGCGGCGGT AGCAACCAGC TGAATGAAAG ATGACAGCGG CTCNTTCGGA TTGGCTCTGC      660

GGTTAGAGCA CCGCAGGGCC CAGAAAATTG GCCGCGGGCC GGTGTGTTGG TCTTTCTGTG      720

ATTGGCTGGA AGTGGTTAGT GACGGAAAAC TGTGGGCTTT ACCAAATGTA AAACGGAGTA      780

CTAACAAAAA GTAACCAGCG GAAATGCCCC CCTAAACTAA AGGTGGTGTC AGTAGTCTCT      840

CTGGCAGTTT AAATACAAAC NATCTCTTTT TAGGCATTGT TTTGAAAGTC CCCACAAGGN      900

TTTGCAAGTA ANAAGTCG                                                   918
```

(2) INFORMATION FOR SEQ ID NO: 23:

(i) SEQUENCE CHARACTERISTICS:
        (A) LENGTH: 309 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 23:

```
AGAGAGGGTT TAGCACAGGC AGCNTATTCC CAGTTTGTGC TGTAGAACTG GAACCTCAGG       60

CCTCATTCTG AAAATNTGCAG CCNTCCCCAG CATCCTTCNT GGCACAGCNT GGCACAGACN     120

TGNTAAGTGT CTATTAGTGA CTAATACAAA GGAGTATTTC AGAACGTTGG CACATCTCAG      180

CACGTTGCAA CTGGCTGGAG CTGGTTGAGC TCTTGCTGCT TCCATATCCC TTTGTAGCTG      240

CTCTCCACTT TTCTGAACCC CGGGTCCATG TGAAAGTCCC CACAAGGNNC TTTGCAAGTA      300

GAGAAGNCG                                                              309
```

(2) INFORMATION FOR SEQ ID NO: 24:

(i) SEQUENCE CHARACTERISTICS:
        (A) LENGTH: 904 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 24:

```
TTTCATTTAA AACNCGGGGG NTGAACCCAA TCTTNANGGT GGCAGTGNGG NNGATCTTAA      60
CGGTTTTTNA GAAAAAAAAN TNCTTCGCTC NCACCCCCAA GCCTCCCNTT CTTANCAGCT     120
TTTTTATANG AAAAAAGATG ATAACGAAAT TTTAAAAACC GTCGTTAGAG GAAATGAAGG     180
TTCAGCCGAC CATTACCTGA NAGTAATGAA GGTNTTCCGG AGGGTTGCCT TCCAATCCCA     240
GATGGATTTG AGTTTCAGGA TCAATTCAGT TACCGNTGAC CATCCACCNN CCTCCNGTAT     300
AATCATTNGA TGAGGATGAA TGGTGAGTGA GTGATGATGA TGATGATGAT GATGAAGGGA     360
TGAGAAGNAC ACTATGATAA CAAGTGTCTC AGTCCACATT AAGGTTTGCC TGNAAATTAG     420
TGCATAAGCC ATGGGAGACA AATTCTTTTC NNACACAATT AATAGTNTCT TANTCCTTCC     480
CATCTTCTCT GCCCCATTCT GTTTTCCACC ACAGGTCTGC AGCGGGCTAC AGCTTCCAGT     540
CTCCAAGCAA ATACCAGAAC TGGAGGAGAA AATTCCAGTC CAGTGAGTCA TGGGCAGGGG     600
GAGGGGTGGG GTAAGGGCAG TGGCGCTCAT TCCTNACATG GTGTCTTCTC TTGCCTAGCC     660
TGGGATCTGA GGGCAAGAGA ACCTGTAAGC TTGATTTGAT TTCCACTGCT GACTGGAGTC     720
ACTGCCAAGG GATTTGGGAC TTCTCCATCT CTCTCTCTAA CCTGAAATCC TTAGGATTCT     780
ATTATTTCAC CGGACCAGAG CTGTAGCAGA GATGAGCTCC AAGTTTGAAA TGAGAAAGGG     840
GAAATTGAGA GCTATGAGCT AGGNGCGAAA GNCCCCACAA AGNNTTTGGC AAGTAGAAAA     900
GNCG                                                                 904
```

(2) INFORMATION FOR SEQ ID NO: 25:

(i) SEQUENCE CHARACTERISTICS:
        (A) LENGTH: 883 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 25:

```
GGGGGGGGAA ACTTNTTTAT NTGGAAAANT TTTGTTTNGG CGGGNAAGGA GTTTTTAANA      60
ANGTTAANGG AAAAAGCTTT TANTTAANAT GACCTTTTTG GGGGAAANAC AAANTTGGTN     120
NGTGTATTNG NGAAAAAGAT TTATTATAAG ATTTTTTATA ANATTTTNGG GGGGGAAATA     180
TTTCAAANAA AATTCTGTAA CAAAAGGNTT TTTGTTTTTT GTTNTCCAAG NAGTTNTCCA     240
GGTAGTTNTC AACAACNNAN GCCNTAGGGA AGGACATCAT ATGGATATTT TCANAGATTT     300
GTTTTTAGGA AACATTNTAA AGTCAAGGTT AAGATGACAG TCAANTCCCA NGAGNGNGGT     360
AACTGTNTGC TTCTTTATTT AAAATTCAAT ATTCAGGATT TCATTTATAC TAACAAGANT     420
AATTACCATC TTAATGAAAC ATAATTTGAA TAATTTGCAA ACAATNTGAT TTTTCTTGAA     480
TATACATGTT ACTAAAATAT TANGGATGCA AATAGNTAAT AAACAAATAG ATANGNAACC     540
ATGGNACACC CCTTCTGTGA TTGGNGGGAC NTGGGCATAA GGCTTGTTTG TATAATAATG     600
TTCATATTTT ACATTCTTCC TNNGAGGANG GTCCTCCCTG TTAAGAAAAN GACTCCAGGA     660
TAAGGAGACA GCACCAGTNT AGGAAGTGAG GNTCTGTTTA ATGTCTTAGC AAAGTAGTAA     720
```

| | |
|---|---:|
| ATGNTGGGAC CATCAGAATA GCCCNTAAGG NTGTGGANAG AACTCTAAAA GCNTGATATA | 780 |
| TATATATATA TATATATATA TATATATATA TATATATATA TNTATATAAA GAGGCAGTAT | 840 |
| TGAAAGACNT NCACCAATNG AGCTGGCNAG CTAGAAGAGG TCG | 883 |

(2) INFORMATION FOR SEQ ID NO: 26:

(i) SEQUENCE CHARACTERISTICS:
        (A) LENGTH: 924 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 26:

| | |
|---|---:|
| TTTGGAAGGN TTTTNAGGAA AGAAANTGTN TTTNAGGGNA GGGAACCCTA TTCCGACGGG | 60 |
| TTGGGGGAAA ATTTTGGGTT GACCCTTCGT TAAAAAGGGT TNCGGTAAAA GGGGGCNANG | 120 |
| TNTTNNAANA AAAATAATAG TAATAGTAGT AGTAATAGTA TTAATAATAA TAATAATTGC | 180 |
| AGGAATCCTG TNACCNTCAG GAATTGGGGA AGTAGTTTCT TATTTTAGGA CCAGGTGTTT | 240 |
| TGTTTCAGGG GAGTTATTTT TTGTTTTGTG GATGGGATGA GTGGTNTCAA TTGCTTTNAA | 300 |
| AAACCTGTAT TAGTTTTGGC ACAGTTAGTG TGTNTCNGNT TCGTTNGAGG AGTTTGAACT | 360 |
| GGATGGTAGG CAATGGNTGC ACAGATTCAT AGTGGCCAGA GTTAGAGTAA ATGCTTGCGG | 420 |
| AGCAGTCAGA ATAGATGAGA NTCAGGGACC CGGCAGATGA TGCAGGGAGA ATGTAAGAGC | 480 |
| AGAAGGTGGT GGGTAGCATG TGGAATGCAC ATTTCCAGGC GTGACATGAN TCGGAACAGC | 540 |
| TGTGACTGCT TAGACCAAAG TGATCCCATC AACACGGCCA TTCAGTAAGG AAGGGTCATG | 600 |
| GGNTCCCCCC NTCCCTTAGG ATTNACATAC AGATAATGAT TGATTGGTGG ACCAGGGGAA | 660 |
| TGGGGAAAAA TGTCNTTTTC GTTGGTATAG TCACTGGTAG CTGCCCATGT TTNTATAAAC | 720 |
| AAATTNTAAA GAAANTCATT GGTTCATACA CGTAAGAAGA CATCAAAACA GAACTGAGGC | 780 |
| AAGTTGGGAA GAGAAATGGG ATTAGTAGGA GAGGGTCAAG AAAAGGCAAA GGTATGTGCA | 840 |
| CATGCATGAA TACATTGTAT ACATGTATGA AAGNGCCACA ATGATGANTT ACCCCANATG | 900 |
| GNNGTTTGGC AAGTAAAAGA GTCG | 924 |

(2) INFORMATION FOR SEQ ID NO: 27:

(i) SEQUENCE CHARACTERISTICS:
        (A) LENGTH: 482 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 27:

| | |
|---|---:|
| TCTCTCCTGA GGGGGGTTTT NTGGANGAAT AGAAGAANAN ACCNCCTCTT TGTTTCNTCC | 60 |
| TGTGGNGNNC CCTGCTGNTA AAGNNGATTT NCNCGGTGNT ATACANNTAA GAAGGAGGAT | 120 |
| CTCTCCCCCC ATTGTNANAG AACCCCGTGT GTGGGGAGGG GGTGTNGCCA CNANCCAGAN | 180 |
| NTGGCCCNNG GGTCNTCTCC CCACTCNTNT GNATAACNTC TNNCCTCCAC AAANACCCCA | 240 |
| NANAAAANCA CCCCNCNTGT GAGNNCNGCA GANGCGCCCT NTNACAAGAN AAGAGNNCAT | 300 |
| GTGNTGTGGC CCTGTGCTNN GACANTNTAN ACTCTTCTNT NGNGGGGNGN GGNCTGTGGT | 360 |
| TTTATAAGAG NGTGTNNCCG TGGGGGGGAG AGTANTCNTT TTATATAGAG AGANAGNGNC | 420 |

| CTGTGNAAAC | TNCCTCTGAG | AAGAGCACCN | TGGTGTTCTC | TCCCATCTNC | TAGNAGGGGA | 480 |
| GG | | | | | | 482 |

(2) INFORMATION FOR SEQ ID NO: 28:

(i) SEQUENCE CHARACTERISTICS:
        (A) LENGTH: 460 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 28:

| TAGCTTCTCT | GTGAGGGGTA | GAACTCAAGC | TCCCCCATGA | ACAGGCTTTG | GGGTTCCTGC | 60 |
| CATCCCCTGG | GGCTGTTCAT | TAGGTGCCCA | CACAGACTTC | TCATGCCATG | ACTCACACTT | 120 |
| GACGTCACAG | AGCACACAAA | GAGCACAAAA | GCAGGCTGAC | CACATCCGGC | CATGCACACC | 180 |
| CCTTTAACAG | TCCCAAGCTT | TCTCTCTCTC | TTCTAAGTCA | CTGCCCTGGG | AAGACGGTTT | 240 |
| CATACCCAAG | CTGATGTGCA | CTTATTTCTT | TGTGTTATTG | CTCTGACAGT | CTCACAGTGC | 300 |
| TCTGCAAACA | CTCTGCATTC | GCCTTTACCA | CACCAGAAGA | AATTCCTCTT | TGTGCAGGGA | 360 |
| AAAATACATT | CGTCTTAGTA | GCTTCTACTT | TCCAGCTTGT | CCCTAGTCTG | TCTGATATGT | 420 |
| GGTTACGTAN | TGTTAGGGGC | CACGGAAGGG | GGGGGGGGGG | | | 460 |

(2) INFORMATION FOR SEQ ID NO: 29:

(i) SEQUENCE CHARACTERISTICS:
        (A) LENGTH: 465 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 29:

| TCCCAAGACA | AGAGGGGCTG | AAGAACGGGG | GGGGGAAGAA | TCAGGAGTGT | GTCGCTGCTT | 60 |
| CCCACATAAA | GACGGCACCT | ANATCTGTCT | CTCTCGGTGT | CTCCTCCCCA | CCTGGGGCAG | 120 |
| GGTGAGCTCT | CTAGACAAGA | GAGAGACTGT | CACAGAGAGA | GAGAGATGTG | TCACCCCTGT | 180 |
| GGAGATCAGA | GNCNCCGACA | CCTAGGGGAC | AAATGGGGAT | CTCTTTTTTT | TTTCTCTCTC | 240 |
| GAGACAGGGG | GTCTCTGTGC | AACACTTGCT | GTTCTGGAGA | TGTTCTGTAG | ACCAGGGTGT | 300 |
| CCCCCAACTC | AGAGAGCCTC | CTCCTTTNCA | CAACTGTGTC | GCCGCCGCCG | CCGCCGCCGC | 360 |
| CATCACCAGG | CTATATTTAC | TATTATCTCT | ATTACTATTG | TTGTGTGTTG | TGTTGAGACA | 420 |
| GGATGCTCAC | GCATAACCCT | ANCTATCCTA | GTGATAGACC | CCACC | | 465 |

(2) INFORMATION FOR SEQ ID NO: 30:

(i) SEQUENCE CHARACTERISTICS:
        (A) LENGTH: 568 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 30:

| TNNCNNTTNC | CTGNGGCCGN | GTANCTCTGA | GNGANAGTNT | CCCCGAGAGG | GGGGGTCTCA | 60 |
| CNNTAGNTNT | ANANAGTATN | GNGTGCTCGA | GTTTNNAGAG | AGCTCTCTCT | NNNTCTCTCT | 120 |

```
CCCCNGAGCT ATNGNNTTAG GGNTATGGCA CNNCNCGTCT CTCNNCNCCN TATNGAGNGG      180

TGNGNTATNG GGGNGAGAGT NTCTGCCCGA GACCCACATT CTCNGAGTNN GGNAGAGTNT      240

GGGAGACACA CANCTCCGGG NANATCTNTC TCCNCCCCCC CAGGGGCGGT GGTNCANATN      300

GNCNACAGAG CCNCNGNNTT NTATGTGGAG AGGGGATATC NCANCNCACN CCCNGAGCAC      360

AGGNTCCACA CNCAGAGANG TGTCTCTCCC CANCACACAA GCACNTCTGG TGAGNTCTAN      420

GTTTTGNGAG AGACNNTGCC CTGTCTCCCT TTTCCCGCT CTNACACACA TGAGAGGGTG       480

TGCACATCTT CCCCATGTCC CTCTCTAAAA CCNCCCCAGA NTTTTGNGGT TNTGTGCAAN      540

ACCCTTTTCA CNCTCANGGG AGATNTTT                                        568

(2) INFORMATION FOR SEQ ID NO: 31:

(i) SEQUENCE CHARACTERISTICS:
        (A) LENGTH: 920 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 31:

GAGGGTTANT TGGCCCAANT CGGCAATCAT CCNGGGAAGA AGANGNCAGG GTTTNGGCAA       60

ATCGGAAGAT CAAGGACGCA ATTCGNGGGG GGGGATGGAT AGNNGCAAAA GGGNACNGAA      120

AGNNGGATTG GNAGGNAAAA TTAAACGGGA GTTGTAATCC AAAAGGACGA CAAGGCAAAA      180

ACAAATCCGG NAGTAAGCAG GAAGCACAGT GAANTTGGGG GAGGCAGNGT GGNGNAANTA      240

AAAAATNGTT TTTTTAATCC CAATANGGTC AACANGTAGG CAANTGGATN TATTAGATAT      300

TATATCTTAG CGCAAGNTTN TCACCCATTG GTCCAACCCA TATAACATGG CGGTGGTNAA      360

TNTNTGAGCN TGGCACAATT TTTNACCCAT TAGTTCCCAA GGCAGATCGC CACCATGCCA      420

GAANAAAATC CCAATTCCAT GGTGGCCCAG TGTGTCCAGC CACCAATANT TTCTTGAATT      480

CAATTAAATC ACCACATGAA GGAATACATA ACACAATAAC ATCTGATCCA ATTGATAAGA      540

TATAATTTGC TCACNTAGAC ATACAAAATC CTGTACATTC CATCTCTTAA GAATATTCAT      600

AACAAACTAT AAATGTGTAG AGAGGAATTT TAATATCCAC TTCCATGTTC TCTTGGCTGC      660

TCCTCTCTCC CAGTCTCCTC CTCCTCCTTT AAAACTTTTT TCTCCCACCC ATCATTTTTT      720

TTTGTCCNAA GGACGGGCCT TGTTNTATCC TGNACCTGCN TTCGTCTGCA TAAGGCCATC      780

ATCCCACAGG CAGGACTGGA GCAATGGCTC ATTGGTTAAG AGCACTTGCT GATCTTGAAG      840

AAGACCAGGG TGCAATTCTC AGAGCACTNC ACTGCTNCAC ACTGAAAGAC CCCACNNGTA      900

GGTTTGGCAA GTAGAAGAGA                                                 920

(2) INFORMATION FOR SEQ ID NO: 32:

(i) SEQUENCE CHARACTERISTICS:
        (A) LENGTH: 176 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 32:

TTGACCATAT TATTTTTATT CACGTTGGGA CAAAAGAGCA AACGCAAAGG ATAGGAAACG       60

AAAGGAATTA ATTTCCTTTC AATAGAGATA TCGGTTTTTT TTAGAGGGAA AAAATTGAGT      120

ATTAGAAAAT AAAAATAGGT TTCGGAATTT CCGGAAAGAC CACTAAATTG TAGGTT          176
```

(2) INFORMATION FOR SEQ ID NO: 33:

(i) SEQUENCE CHARACTERISTICS:
        (A) LENGTH: 336 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 33:

```
AAAAGGGNTN CCGAANAAAA ANAATTNGGA TCTTNTGGGG GCCCNGAGGN AAAAAAAANA    60

NTAANCNGGG GGNGACCCAG NGAANAGACA AATTNTTTTN CCNGGAGTCC TTGGGGTGNN   120

ANGCCAAACN GNCGTTTANN GNAANNNGNC GNGNTACCNC TTCGGAGNGG GGGCGCTGNA   180

AAAGAATNGT GAGAATNCNG TTACNNGTGT TGNTTNATCN GAGATAGTNG TNTGTAACAA   240

CCCCGATTCA GCCNGAAAGT TACGCATATG CGNANCGTTG TGTGAATCGA ACCTGGNNAA   300

AACAGACCCA TNGNCAAGNG GCAGACCNAA CGGAAC                             336
```

(2) INFORMATION FOR SEQ ID NO: 34:

(i) SEQUENCE CHARACTERISTICS:
        (A) LENGTH: 92 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 34:

```
TGAATAAGGG TACAAAGATT GTGTTTCAGA GGAGAGAGGT AACAAGAAAA GACTCCTAAC    60

GCAATGGCCA GAGGGCCAAG AAAAAGGGAA AA                                  92
```

(2) INFORMATION FOR SEQ ID NO: 35:

(i) SEQUENCE CHARACTERISTICS:
        (A) LENGTH: 838 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 35:

```
GGNGTNATTT TCTTCTNGTG AANTCTTTNC CAAATCCGNG GGTNTGNCCC ANNGCCCCNN    60

TTTATACACN NNATTACNCN TNNNCCAAAA CNCTATATGT NTCGANATGT CCCATNTTAA   120

ANATATGNGA CTCAGTTTGA GTNTCCCCAN NTTGGNGTTG GGGTATNTGG GTAAANACAN   180

NGACCCTCTN NGGNGNTTTA TTTATATATN NGNCCCNATA TAACNCAGAG ATCTGTGTAA   240

AAAATATNNC NNTTCGCGGG GNGGGAGATT TCTCTCTGNN GTAGNGCNCT CNNCTGAGAN   300

GCACAGNGCC CTGTGTTNTN TCCCCCTCNC CGAAAANAAT TTTNTNCAAA AANANANAAT   360

ATNNACANAC CCCNANAAAT ATNCCCCTTN TCTACCNCCC CTCAAANACA CCNCNNTTTT   420

TTTTTNCCCC TCAGAAATNT TTNTAATNTG GGNNAAAAAA ATCTNNGNTG GNNTTNTCCC   480

CCCNTTTNNA GNCGCCCCCT NNAAACCCCC NCTNTTNANA GANAAATATG TANACTCNTA   540

TTTAAAAAAN AACANTTTTT GTTNGGGCTN GGGTNTNCCA NCCCTTCACT CTCTTTGTGG   600

GTNTNCCTTN CCATATNCCC CCTNTTTGAG ACNTTTAAAN AACCCTCTCC CTAATTCCTC   660

CNCCCNCTGT TTCCCCCTTT TNNAAAAACN TCNGGCCCCT TNGCCCCCCT TTTCTNACTC   720
```

| | | |
|---|---|---|
| CCTCTTNTCC NGAGATTTTT TCCTCNTNNT NNCTAATTCC NTTNTTCNAN TCTANATNNC | 780 |
| NNTGTTNCNA NCGCANGNTN NCCCCNCCTT NNNCTNAATT NTGGGNAGG TTCCAACC | 838 |

(2) INFORMATION FOR SEQ ID NO: 36:

(i) SEQUENCE CHARACTERISTICS:
        (A) LENGTH: 314 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 36:

| | |
|---|---|
| CAAACCAGAA ATGGCCCAAG GGTCATCTCC CCACTCAGTA TGAATAACAT CTAACCTCCA | 60 |
| CAAAAACCCC AAAAAAAAAC ACCCCAGATG TGAGAACAGC AGAAGCGCCC TATAACAAGA | 120 |
| AAAGAGAACA TGTGATGTGG CCCTGTGCTA AGACAATATA AACTCTTCTA TAGAGGGGAG | 180 |
| AGGACTGTGG TTTTATAAGA GAGTGTAACC GTGGGGGGGA GAGTAATCAT TTTTATATAG | 240 |
| AGAGAAAGAG ACCTGTGAAA ACTACCTCTG AGAAGAGCAC CATGGTGTTC TCTCCCATCT | 300 |
| ACTAGAAGGG GAGG | 314 |

(2) INFORMATION FOR SEQ ID NO: 37:

(i) SEQUENCE CHARACTERISTICS:
        (A) LENGTH: 226 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 37:

| | |
|---|---|
| AGGGGGGGAA ACCCCTTCGC CNCGGGCCTA TCGNAANTTT TNNTCCACCG TAAAANATTT | 60 |
| NCCANGNGCN CCATGTANGG ATTGNGGGNG TAGTGGGGGG AACGATTNTG GAGGGGCCTA | 120 |
| AAAGGNANAT AGAGGACGTA TTGTATTTGG TTTTGCNGAG CCAGTACCTT NGAAAAAGGT | 180 |
| TGGTATTTTT GATCCGGCAA CAACCACNGT GGTAGNGTGT TTTTTT | 226 |

(2) INFORMATION FOR SEQ ID NO: 38:

(i) SEQUENCE CHARACTERISTICS:
        (A) LENGTH: 843 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 38:

| | |
|---|---|
| GAATTAAAAC GGGAAAGATT GGAATTCAAT TTCTTACAGC CAAAAGCTAG ACCGGGCATA | 60 |
| TAGGAGATTA TTTCGATTTA GCACCTTCCA AAGCCTGCCC CAGATTTAAA GTTTAGGGGT | 120 |
| ATTATTTAAA AGCAGGTTCC GGGAAGTTCC AAGATAGGCC TAGAGGTAAT GGTATGCAAG | 180 |
| CAGTCCTAGG TTTCAGAAGA GTTCAAACAC GGGTCTTCAG GAAAAGACGG AAAGTGTAGA | 240 |
| TTGATCAGGC CAGCAATCAT ACAACAGTGT TTGTTGTAGT ATTACCTTTT CTAATGGTTG | 300 |
| TCACTGAAAA GAGATTATTC TAGGTTTGGA GATACAAAAT TAAAAGAATA AACCCCAAAA | 360 |
| GGCCACAGAC CCAGGGTAAG CCCTGTAGCC AGGACTAGCA GGCCATAAAG AAAAAGGAGC | 420 |
| ACAGGAAACA CTGTCCAGGC AGGACTGGCA AGCCATAAAG ATAAGGAAAA GGAATGCAGG | 480 |

```
AACCAGCCTG AGTTAATGAG AAAAATTAAT GGGACGTCTG GCAGGAAGAC ATCTCCCCCT      540

AGCACACTCC GGGCCATATC TCAACTAGGT GTCCTCCAGC CCCTGACTTA TAGCACGTAC      600

TCTATCTGCT TTGTTATCAC AGATATGTTT GAATGAGCCA ATTGTATGTA ACCACGCCAA      660

AACCCCCTAG CTTTGTCTAT ATAACCGTCT GACTTTTGAG TTTCGTGTTC AACTCCTCTG      720

TATCTTGGGT GAGACACGTG TTGGCCCGGA GCTTCGTTAT TATTAAACGA CCTCTTGCTA      780

TTACATCATG ACCAGTCTGG TCCTGTTGTA AGACATTGGC AAAAGAGCCT GAAAACTAGA      840

AAA                                                                   843

(2) INFORMATION FOR SEQ ID NO: 39:

(i) SEQUENCE CHARACTERISTICS:
        (A) LENGTH: 943 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 39:

TTTTTTTTTT GGAAAAACGG GTTTAATAAG GGGNANGNAT CCGAACCCCC ACTCGGGNGA       60

AAGGAAANAA AANAATANGG GGGGAANAAN GANTTGGNGG TAATGCTTTA CCACGACAAA      120

CTAGTCCCAT TNTTCGGGGG GGGAAAGGGA NGGCATGAAT AATGGGGTGA AGGCNGGCAC      180

CCACCCCATT TTTTCGGGGG TAAGTCNGTT TTTTTTTGGT ANATCAAAGT TCCTTTCGGA      240

ANATGTCCGT TTNATCCAAG GNGTTTTGGG TGTTNNAATT AGNATTTNNG NGAGTTTCAA      300

AAGTTTGTGT TCNNGAGNAG TTTGTAATTG GTTCAGCNGG TTTTTTTGTG NCAGGAAAGC      360

AGACCCNTGT TTGGGAGGGA GATCCAATTT TNTAGTTCCC ATTTGGCTGT TTCCTTAGTA      420

ATGGGTCTGC AGACAGTNTG AAGTNTATGA GTTGGTCCCT TCTCNTATCA GCCCGGGGTG      480

GCATTNTGTC CAAAGGAGGA AATCCAGCAG CCAGACTAGA TTTCAGTNTC CTTTNTAACA      540

GGGAAGTTAG ACACACCCGG CCAGTTGCAG CCTTTCCACC CCCAANGAGT GAACCCTGCC      600

NTTTCAGNTT TNACCCAATT TACTTTCGTT GGCTTAGCAT GCAGANTCTT TGGCTCCATG      660

CCCGGAGCAG CTGACATGGG AGGCTTTGAA ACTTCCATTA TCATAGAATG GCAGGCAGGT      720

CNTTTGCGGT TAAAACCAGG AGCNTGGGCC AATGAGATGG NTCANTGAGC AAAGGCGCTT      780

ACTGCCAACC CTGATGCCNT CAGTTTAGTN TTGGAATTCA CAGGGTAGAA GTTGAAAACC      840

TTTGACTCTT CAAAAGTTGT CCTGTAGCAG GGCAGTGGTG GTGCANACNT TTAATTGNNG      900

TACTTGTGAT AGTCCCACAA GGANCTTNGC AAGTAAGAAG TCG                       943

(2) INFORMATION FOR SEQ ID NO: 40:

(i) SEQUENCE CHARACTERISTICS:
        (A) LENGTH: 904 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 40:

ACTTCTCTAC TTGCCATGGT CCTTGTGGAA TCTTTCAATC TGTGTCCTTA GAACGCTAAG       60

CTAAGACTTG ACCTTGGCTC CCAGGGCGGG CTGGGACTTG GCCACCCCGT GAAAAGGGCT      120

CTTTCTCAGG CAGGTGTTTT CGTTTAAGAA AATAAACCAT CCAAGTCCGG GCAGACTGAG      180
```

```
AGCTACACAC CCCTCCAAGC CAATCTGGAG TGGCTCTGCC CAACCCCCAC TGCTGGGAAA      240

ACATGGCTGC CTCAGCACCT CCCTAAATGA AGGGAACAGA GTGTCTCCTG TGGCCTTGAA      300

AATATTAATA AATGAGACTT AACCTGATGG CTCAAGGCTC TCAGGGGCT TTTTTTTGTT       360

TTTACACACT CTGTGGAGCT GTTACAAGGT CAGTCAGTCA TTTGCATGGG ACAGACAATC      420

TGTTTTAATA TTTTATATGT TTGTCTTTTA AAAAACCTAA GATCTATATC TTTTTACATT      480

TTATTGTTTT GTTCAAAAAA AAAGTTTTA CACAATGATC AAAAAGTTCA AATGAAGTCT       540

TTTTTAAACC TCTCTCCTGC CAAAGGAAAC CAAGCAAACT TTTTCCAGAA ACCTGATAAG      600

AATATCTCCC TTTTACCCTG GAAACATTAA AAATAAGGAT CCCTGAATTA AAAATTCTAT      660

TCCAGAATCC TAATTTTATT TTTTATTAAA AAAAAATAAA ACCCCCTTAA CTGACGGGCG      720

GTTTTTAAAT CACCTGCCTT CAAAACCCCC CTGGAAATTT TTAAAATTTT TTTTTTGTTC      780

CCCAACATTC CTCCCCCCCT AATAACACCT GATTGATACC CACCAATTTT CCACTGTGGG     840

TGATTGAGGT GGTCCCCCCT CTTTTTTGCC GTTTGATTTC CCCCGTTAAA AAATTTAGAA      900

AAAG                                                                    904
```

(2) INFORMATION FOR SEQ ID NO: 41:

(i) SEQUENCE CHARACTERISTICS:
        (A) LENGTH: 917 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 41:

```
AAGGGGGGNG AAATTTAGNG GACNAAAATT ATTCCTTAAG GGCCNCCTTT CTTCAGGGAA      60

NANGGGGGAA GGAGATANTN CGGCCCTTGT CCGCCTTTTN GGANACGATA GGGNCGGTTC      120

GGNTTGGAAA TTTTTCCTCC AAAATTNCCA ACAAAAATNG TTTTTCCCCT TCCTTCAAAA      180

AGAAAATTGG TTTTTTTGNN GGCTTNGGGG NGTCNGGAAG TCANAACCCN GNGTATTATT     240

GCNTTCCAGC CCCACCCGTN AGTTCATTGG TAATTCCTAT TCGTTCGGNT CAANATAATT     300

CGGNACTTCC GCTTCCNAAT GGATCCCTTC AANGATTNGG TTTTTCCGGA TTATCGCAAG    360

TCCCCNGGTT NTCCAATCCG GAGCGCNTCG GATATTTCCG GNTNTCCGTG CNTTTCTAGC    420

CCCACCCCCA NGACCACCNT TGGTTNTTTA GGTGGGTCTT TGATCCGCTT CACGTTGCTT    480

CAGTGACNTA GATCCTTNTT CGGTCTTTCC GGCTCATTTT AGTCTCGAGT TATTCTCAGC    540

TGTGTTANAA AAAAACANNA NAANAANCTC CGCCTCGCCC TTCCGNTTCG GTTCTTTCCG    600

CNNGCNTTCG GGCGGGCNGT NTCTGCCTTC TCCACGTGAC GNTTNTTCGG CNTCCCAGTN   660

ACCCCCTCCN TCCACGCCTT CNTCCAGNTT CAGCTTNTGT GCTCGTCCCG GNTGTGCCGC   720

CANNTNGTGT CAATTCCNGA CCGCGGCGGG GGCCGGGCAG NTGGGGNATN TAGGGCGGGC    780

AGACAGTCGG CCNATCTCCA TAGGCCGTTC CCTATNCTNC CCTGATTTTT TTAAACCATT    840

TCCAAAAGCT CGCTGTCCTC TTTCCGGGNC TTCCATTNNG GNGTNTCCAN AAGGAAGNAA    900

GNCNAGTAAA GGANCTC                                                      917
```

(2) INFORMATION FOR SEQ ID NO: 42:

(i) SEQUENCE CHARACTERISTICS:
        (A) LENGTH: 835 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 42:

```
GGNCCCCTAN NGATTGGCCN TTGATCAAGA NGGGACCATC CTGNACCTGG NGGTNGNTGT      60
TTCCGCTTGG GACGGAGATG GTTGTTTTTG CGGAGTAGTT TCNGNGGGTT TGAGGCGCGG     120
NTANTTTTTT TGTTNTGGTC CAGACCGTTT TGATTTAGCC GCNGCNGACA GTAATGGGGC     180
GATACCTCAG NTCCTTGTGA ACCCAGGGTG CAGNTGGTTC AGCAGGATAG ATGTACAGCC     240
TCCGAACTTT TCAATTCCCN GACTAACCAT TGATGTCAAG TTGAGTGTTT AAATGCTTGC     300
TACCAAGCTG GTTGGTAACC TGAGTTCAGT CCCTGGAACC CACATGGGGA GAGAGAACAT     360
GCTTCTGTAA CTTGTCCCCT AACTACCCCC AATACACGCA TGCGCGCGCG CGCGCACACA     420
CACACACACA CACACACACA CACACAGAGA GAGAGAGAGA GAGAGAGAGA GAGAGAAGCA     480
CAAACAATAA AAGAAAAAAA TAAAATCTCA TTTAATTTTC ATTAGTATAA TACCTTGATT     540
CTTTGAATGA CAGCAAGATA AAGTAAACCA AGCACACTG TAGAAGGGAT TACGCAACTG      600
AAAAGTGACA ATCCTTACTC CAGCCCTTCC TGCTATGTTG GCAGTCTTGC TGGGAGCCAT     660
TGATCTAATC AGTTTTATTT GAGGCAGGGG CTCATGTAGC CCAGGAGGAT GGTCAAATCC     720
ATAGCTCATC TGAGGATGAG TTTGAACCTC TGACCCTCCT CATTCTCCAG TTCTCCATAT     780
CCTGAGTGCT GGCACTGAAA GACNCCACNA GTAGCCTTGG CAGGCTAGAA ANGNT          835
```

(2) INFORMATION FOR SEQ ID NO: 43:

(i) SEQUENCE CHARACTERISTICS:
        (A) LENGTH: 924 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 43:

```
GTNTTTTNGC CGNGGGAATT TAAGGGNGAT TTGGAGACTT TNGAATTTTC GAANGTTCCA      60
AAATAGANNT TNAGGNCAAT GGGNTTGGGG CAGNGGNGCT TTTTTAAATC ANANAAGTAT     120
TAGATTTNTA TGGAAACCCT GGGGGTTCCA GTTTAATCCC TTCATCATCT TGAAATATNA     180
CTTGTTTATG GGAANGGTGN GATAGCAGCC NGAAACAGAG GTTTTTATTA TTACTGTTAG     240
AGANGAGGAT TGGGGAATAG AACAATGAGA GTCTTGGTAA TATTNTTCNG GAAACAACNG     300
ACATAATTGG AACATTAAGG AAATATATCC ATGCATTCTG TACTTGCAAA TTGCTCCAAG     360
GAAGATGGAG AGTATTGTAT TTCAGATAGA GATANGACTA TACCTGTTAT TTTTTTCATT     420
ATAGCAACAT TAAAAAAGAT AGTAATCTAA TTTCACATAA CCATTACTAC TAAAGTATAT     480
ATGTANTCTT TGTTTATCAG GTTTTACTTC TCAGAAATTG CAGCATCTCC TACAGAGCCT     540
GTCAAATGAG ACNGCATAGA TCCCCAGAGA ACAGAGAGAC TGGGAAATCA TTGAAATTAC     600
ACAATCCTAT CCCAAATGTT TGCGTAGACT CAAGCTCGTA TCAGCTCATA AGATCAGTGT     660
GTGTGTGTGT TTGTGTGTGT GTGTGTCCCG CACATGCTTG AGTATGCATG TGTGCATGCA     720
TGTGTGTATG TCTATTGCAT TAGTAGAGAT GTTAAGGTTG AATGTATTTT CTGCTCATGG     780
TCATTGTAAG ATATTGTGCT GTATGTGATA AGAATCAATG TAACAAGGCT GGAGAGATGA     840
CTTCAGCTGT TAAAGGCTAG ACTCACTACC AAAAATAGNG CNATCAGTGT GAANTTCCCC     900
ACAGGAGCTT AGCAAGNTAA TAGG                                            924
```

(2) INFORMATION FOR SEQ ID NO: 44:

(i) SEQUENCE CHARACTERISTICS:
        (A) LENGTH: 435 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 44:

```
GATTCCAGAG AGAGGAGTGA ACTGGCAGAT AAGGCAGTCA GCATAATGGC TTAGATACCA      60

TGTGCTTTCG CTCACTATGC ACCCATGACA CAAGATCACA GGGTACAGGC CTGGACCATG     120

GCAGAGTATA CACTGGTTGG GTAAATGAAG AGGAGAGACA GAGTGGGAAG TCGGCTTAGT     180

GGATATGGAC TTCAAATTTG ATGAACAAGC AATTCAAATG AGTATCGTGG GCTTGANTGG     240

TATGAAGACC CGTTTGCAAA GCAGTGGTCA TAAGAGAGAA AAGAGAGAGA GAGAGAGAGA     300

GAGAGAGAGA GAGAGAGNAA GAGAGAGAGN GTGTGTTGTT GTTGTTGTTG TTGTTGTTTA     360

TTGGTTNATA ACAANATNTA CCTTTGGGCN CTTTNGAAAG ACTNTNCACA AAGGAGCTTG     420

NCAAGCTAGA AAGGT                                                     435
```

(2) INFORMATION FOR SEQ ID NO: 45:

(i) SEQUENCE CHARACTERISTICS:
        (A) LENGTH: 919 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 45:

```
CCCCNGTTAC CCNGANGTTT ACNNGTTGGA TTAAANGGGN NNNAAAACGG GTGGGGNNAA      60

ACGAATTTTT TGTNCNCGAC CCNTCCCCGG TTGGGGNTGG NGAAATAAGT TTTAAGGTGG     120

GAAANGGAAA GGAAATAAAA ANATTTTTTT TNAAGGAAGT TCCTTNCCAC AAAAAANTNG     180

NTTNGTTCAG TAGGGTTCGG GCCCGGGAGG NAAGGCAANN TTGAANTNCA NTTAAAAATT     240

NCCNGGAANG TACCTTGGGN AGGGATTACC NTGNAATTTN TTTAAGAAAA NNTGGGTNTT     300

TTGGGGNGAT TTTNNGCCCC ACCTGGACCA NTTTNGGGAA ANGCAGAAAC GTTCCAGNGN     360

GTTTTCCTTC CAGAGAGAGG GTTAGGTTCC TTCAGGGGNT TCCAAGGACG GGACCAGAA     420

NGTGAAACAA ACCAGGNTNT GAAGAGACCA GNCGGGGGGG GGGGAGGGGG CCGTTNTAGA     480

TAGATTGAAC CTGCAGAGTT GCCTGTTACC TGAAGTTGTC ACCNTTTNAC CNACANACTT     540

NATAAANNTN TGNTGACCAT NTCAGCAAGT GTCACCTTCG TTGCCAGGAC ACAAGTTTCT     600

TAAAGCTTAT TTCAGTNTCA CCCGCTGGGG AGANACATTC AGGGCATGGG CGTCCCCCAG     660

CCNTCGGGGA GAATGTGGGA GGTGGCGATG TGGGAGGGAT TCGAGAGAAG AGAATGCTTA     720

AGAACCATCC AGGGAACCTG TGCGTTTGAA GGTNTGAGTT ACACACAGGC TGCTCAGGAA     780

GGAGCTAGAG CTCCAAATAG GAGCTGTGAT CAGGCTGTGT GTGTGTGCTG GAAGGGCCAG     840

TTAGCAGAGG TTGTNTTGAC CACCCAGNCT ATTGAATTGN GNNTNNTCCC AAANGGANNT     900

TTGGCAAGTT AATGAAGTC                                                 919
```

(2) INFORMATION FOR SEQ ID NO: 46:

(i) SEQUENCE CHARACTERISTICS:
        (A) LENGTH: 915 base pairs
        (B) TYPE: nucleic acid

```
            (C) STRANDEDNESS: double
            (D) TOPOLOGY: linear (ii) MOLECULE TYPE: DNA (genomic)

(xi) SEQUENCE DESCRIPTION: SEQ ID NO: 46:

TTTTTTGGAA TNTTGGAACC NCGNTTTGGA AGAAGACCTT TNNNNTNCAA TTGGGGAANA      60

ATAACCGGGG CCAAACCTTG GGAAGGGGGG AAAANATTCC NGGGGGGAGG TAATTTNTTG     120

GNNGGNAGGG GNGGAGGTTA NTATNNCGGT TGNGGAAGTT TGGAATTGTC CNAANGGATT     180

TTGTTTAAAA AGAGGNTTGC NGGGCNTGNT CCCTTCAACC ANGAGGTGGG GCCNTTGCAT     240

TTATTTTCCT TTTAACNTTT GAAGGTGAAG CCGGGTTATT TNTTTGTCCT TCGTACATTT     300

ATCACCACGG NGTTTAAAAN GTNTTTTTAT TTCGNTTTNA TGGAGGNGAG TTAAATNTCN     360

ATTTCCAATT AAACCTCNGT GAAACCTTCT TTGATCCTGC CTNGTGTTTC CTGAGTGNGA     420

CATACCTGCN TAGTTNTGGC CTTCCCTTTC CTTNTCGTCC TTCTTCCATT CCCTTCCGAA     480

GATTCCTGAA GGAGTGAAGG TTTGGGAAAG GGGGAGGGAC AGAGTGTCCA GGGCTTGCGT     540

GTCAGTAGAC ANNAAANAGC CGNAGGGCAG CCCGGGGTGA AACCACAAGG CAGAGGCCCC     600

AGGGTAGACA GCTGACAGGC CCGCCCACTT TGGCTCCTGC NTTCGCTGTC TCACCCCAGA     660

ATTTTCCTGG CAGGAGTGGA AGAAGTTGGT ATCGAGTCTT TGAGCCCTGA CTCATTNTCT     720

GTCCTAGCTG GGTGCTCCTC AGTTACATCT CCAAGTGTCT CTCAGGGGTT CAGTGTTAGC     780

CACATGGCTG CCTCAGNTCA AACCGGAAAC CCAAGAGGCG GAAACATGCT TCATTTAATT     840

CCCATCTGGG GACCCNTACA AATTTANGGN TTGTACTNAN GGATTNCCAC AANGNNAAAG     900

GCNAGNTAGA NAGGT                                                     915

(2) INFORMATION FOR SEQ ID NO: 47:

(i) SEQUENCE CHARACTERISTICS:
        (A) LENGTH: 849 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 47:

GTTAAANANG AAAAAGNGGG GGTGACAGGG GGNGANACCC NTTGCGCCGG GCTATGGATT      60

NTNGGCACCG ANAAGATTTN CAGGNGACAN GGAAGGTGGN NGGGGANGGG GGAAAGTTTN     120

GAGGGGCCAA AAGGANAAGG AGGANGATTG ATTGGTTNGG GAGCAGTACT TGGAAAGAGT     180

GTGTTNGATC GGNAAACAAC CACGNGNAGN GNGTTTTTGT TGCAGCAGAG ANAAGNGAGA     240

AAAAGATNTC AGGAGATCTT GATTTTTTTC GGGTCGAGCT ANGTTGGGGG ATGNGAGGGN     300

ACAATTCACA AGATTTGTTC ACAGGGAGNT CNAGGAGGTG GTCCCANTAG CCGGTAGGGG     360

GGTTTTCTCA ANAAATGGGN TCAGTCAGGT GNTTGCCTAG ATCTTTCATT AGTTCCTCCC     420

TTCAAAGGGA NTTTGAAGGA GTGCTTTGTC CTGTGGAGCA ATTGACTCAA TCAATAAACN     480

TAAGTAATCT CCCGGANTAC TGNNGANGCG TTCCCAGAGA GGTCCCCCGT AGTNACCAGT     540

GAATCACAAT TTCCTAACCA TANGANTNTT GTTAATCTCA CCACATAAAC CCACAATTCT     600

CGCGTCCTTN GTGATGGTTT CAAAGTCNGG AATATNTTTT CCTCCATCCC TCCTTTCCTT     660

CCTCCTTNTA TCCCTCCCTT CCTTTTTTCC TTTCACAGGA TCTCANNATG CAGCCCAGTC     720

AGGCCTTAAA CTTGTGATCC TCCTGTCTCA GCCTCCTAGG TGTTAAGATG ACCCAAATGT     780

AAACCATGTC CAGNNACTTC CTCCTAATCC CATCTTCAGA TATCCTTTAA GACCAAATTA     840
```

AATATTAAC 849

(2) INFORMATION FOR SEQ ID NO: 48:

(i) SEQUENCE CHARACTERISTICS:
        (A) LENGTH: 925 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 48:

```
AAAAAAANAA ATNTTGGNGG ACCNAANACC ACCAATGGGT TTTGGGGTCC GANCGNNCAA      60
ACNTGNTTTC ANTGTTNTTC TGGNTTTNTT TGNNTAAACT TGGGGTTTTA AGGGTTNAAG     120
GTTCCAAACC CNATGTTTTC GCNCAATTTA GGCGGGGNGG GGAATCCNTT TGGGGANGTT     180
TNAGTATCTA GTTAAGAGGG GCCATTTNGA GATTGACACC TGAGTTAAAC TTCNGAACNN     240
AGNTGTNTAA TNAACCCGTG AAGGGGCTGA GGGGNGTTGG TTANGATNCT CAATNNTAGG     300
GNAAAAANNA ATGTGGTANG GAGACAGTAG NNTANTCGGA NCAANTCGC ATCGGCCNTT      360
NNATTAATAA GCAGNCAATT GAGGAGGTTA TCCACGACAG NGANAGGTGC AGACCCCACG     420
CACACTGTGA CAGTGGTTTA TGTNACANNA TNTCGGGAGN GATGGNGCCA CACCNACTGA     480
GTTCCGTTTT GTTCGGNTGA AGGTAGGNCA ANACTGGCAN AGGTGTTNGG GGGCNAGACG     540
NGAGATGNGG NTTGAGCNTT CAGACCNAGN TNCANGGNNN NGGACNANGG TCCCCNGNGC     600
CNTTCTAGCC TNGAGCAGNT TCNAGAGAAN TATTCGNCGG GTATAGGTCG CCCCNANGAC     660
GCNAAACGAC CGNGAGCGAG GGCGGAACAG CCAATCAGTT CGANTTATCG TGTNTGTTNG     720
CGGGGTTTGA TCCCNGAGTT AGNTCAATGA GCCCANAACC CTGAGTGGAG GNACCGTCAT     780
GGGAGGAGAG GNGAGTCACC NGGTACCTGG CATACNGATG GACCATCCAG TANTTGGATN     840
GGAGGGCGAT ATNGTNANTC TTAGGGGNTC TCCTGAGGAG GGNATACCCG TGAGTTCCGT     900
AAGGGCGTTN GCAAGTAANA AGTCG                                          925
```

(2) INFORMATION FOR SEQ ID NO: 49:

(i) SEQUENCE CHARACTERISTICS:
        (A) LENGTH: 827 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 49:

```
GCCAGTTGCC CTCAGATGNC CNATACCCCA CNGGGGGNGT CTCNCCCCTC TCTCAANTGT      60
ACACACACTT CCCCATAGAC ACNGGGGACC ATAGCTCTAG GGGGAAAACA AAATNTTATN     120
TGTGTGTGCA CNTGTGNGTG TGTGTGNTGC CCCAAACACA GGGGTNTCTC TTCCCCAGNG     180
GCCCTAAAAT GTTNTNTGTT CNCCACTNGG NCCTCATNTN NACATACCCC CCNNGNCTCN     240
GNCCCNNATA CCCNGACANN GAATGTGTGN NTNCCCATNN GCGCTNTCAC CACCACAGNT     300
TTTNTAANAC ATCTCTCCCC NNNATATCTN TTNTTTNNTN NGGGTCTCAA TGGAGACNAC     360
ATATACACNA GTGTGTNAGA CACACCCCCA CACCCCAAAT GNGCGGGGGG AGGGCTCTTA     420
GCGCAANGAG AGNGCAGNGT GCTTACTCCT CGCCCCCTCT AGAAAACTCA CACTNTTNAG     480
ATCTCGGGAC TCNNCCTCAG CNCATTCTCT ATCTCCCANA AANACACAGA GNNACCCTNT     540
```

-continued

```
TTGNGAAAAC TCANNTGTGT ATAGTGCTCT GNGTGTNACC CCNAGNCCAC ACCCCCATAA    600

NANATNTNTC TCTCAAAACA TGTGCATGNG CGTGTAACAC TCNCCATCTC TCGGGCNNGC    660

TCTCCCCNTN ACATCTCTCG NGNNAANANA AATATATCCC CTCNNTTANC CCCCGTGTCC    720

NGGANAATAT TNCCCCCCTG NGACCANTCC CTCCCCGGAG ACCNANCCCC CCCGTGGANA    780

CCCCCCCCNG GNATCAACCC CCCCGGGTAN ACAACCCCCG GAACCCC                  827
```

(2) INFORMATION FOR SEQ ID NO: 50:

(i) SEQUENCE CHARACTERISTICS:
        (A) LENGTH: 899 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 50:

```
AAAAATTGTA AGGAGTTGGG GGNATCCCCC ATAATTNAAA NAGGGAACAA NCCNTAAAGG     60

GAGGGNNGGG AANGGCCAAN ATTGGNTTAA AAANAGTANG TTTGGTTGAT CCANACACAA    120

GGAATTTGTT ANAATTTTNN TAATGGAAAT NGGGCACTTC AATTGGGANG ATAAAACCCC    180

AGGAAGTGAT ACCNGGGTTA TCAAGTNAAA CNTGATTCTT GGNGNNGAGG GAAAGGATAT    240

TGAATTTGAG TGAGTGCAGG TGAAGTGAGA CTTGGGAGNA CAGGTCATGC CCACCCAAGG    300

GAGGAGCAAG GGNTGGGCAG TGTAGGTGGT GNGGTGGTCC TTCCTGGGGT GGGCGGGGAG    360

ACAGATGAGA ACGTTATTGG AGGACAGGCA CAAGTGTTAC TGAAATGCAA ATCCCTGTAG    420

ATNTGGAAAA GTTCTGGNTT CAGGCTTGAT GCTTGGGCCG GCAACTGTGN ACTTTCCCTG    480

TACGTTCAGC CCCCCCACCC TTACGGAAGT TNTCGTCACT GAGANTAGTG GCTAATCAGA    540

GTCTTCAATG GACCTGCCAA TCAGAAAGGA AGGCGGGCTT TTCCGGGTGC NTAGGTGTAG    600

GATTCGCTCA GTAGTTAAGC AGTCTTAACT GGTTNTGGCT GCTGTGCTCT CTGTCCTGCC    660

GTTGGATTNT NTGAGGCATG TTCAGGCAAG CTCCAAAGTT GCGACATGGT GAGCACAGGG    720

GCAGGGGGG CGGGCGGACG GGCAGGGGAC TGAGCAGTGG GAGCTGGTGT GGTGGGTCTT     780

TCCCGGGGCT GAGTTGGAAT CCGCGGCTAC CCGTGAGGTC TTAGCCACTC ACTAGACCCA    840

GCGGCAGTTT CTGAATAACT TTCCTTGTAG GGGCTGCAAC TCTTGAAAGA CCCCACCAG     899
```

(2) INFORMATION FOR SEQ ID NO: 51:

(i) SEQUENCE CHARACTERISTICS:
        (A) LENGTH: 852 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 51:

```
AAAACATTGG CNAGACTTGT AATAATTNCC NGTTNGGGGA AAANAGNGGN NTGNGCTTCG     60

GGGGNGGGGA NCCGAGGTTC CCCCCAAATT TCTTANNAAT TGAGGGANAT TNANGGGGGG    120

AACCGANNGN TCNNNAAGGN GGGGTTTTTC CCNTTNGCCC CCTTGGGGNT TNACAANTTG    180

ACCNTNAGTT AACGGGGANA ACCCGCCNTG TCCTNNGGGA GGGGGGTTCC CTNGGGAGTT    240

NCGTNGTGGG TTTCAGTTCG GACCAGGTCG TTNACTCGAA AACNGGTCCG CNGTATNCAC    300

CCGGTNGGCN GNCTGTTGAN NGCTAACGNG GTAAGTATTT TCATGTGTCC GAACGTGTTA    360

GACTCCAAGT ATGGCCATGT GCANGAACCN CCGGTTAGCN AGACGCAGAG CGTGATCNGN    420
```

```
GGAGGNTCTN CAGGNGTCCA ACCNGGNANG NCAAGATNCG TCGACACTGG CAGNACCCAN      480

TGGNGACTGG NNGATCAGAG GGAGNCAGGT ACGCNGGGAA ACAGAGTTGN TGNATTGGAT      540

CCGGNANACG GACANNCNAG NGGGNCNGTN GTTTGGTATG TGNGCTAGNA GGANGCCAGG      600

NACAGTCGGA AAGGNTGTCG GGAGGNTCNG ATCATGTCNT ACATAACCNC TCGTGAGTAT      660

GCGGTGGNTG TGGAGTTGNG CAGGCGGCAG NTAACGCACC AGAGAATTCN GATNTNTCCG      720

CAGATCGACA GATNTGTTAG GTGGGTCTCT GACGTTNAGG NCGANAGGAN NNGGGAGNGG      780

ATAACANTNT CACACAGAAT TTCACTGAGG CTGAAAGACC CCANTTGTAA NTGNCCAAGC      840

TAGCTGAAAT CG                                                         852
```

(2) INFORMATION FOR SEQ ID NO: 52:

(i) SEQUENCE CHARACTERISTICS:
        (A) LENGTH: 967 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 52:

```
AAANCCTTCC CGGNGGGGTT AAAANAGATT ANGGGTTTTC CGNGGGGAAN CCCCNNCCNC       60

CGCCTTCGTA ATTTGTCCCC AAGAAAAATT CCCGCGCCCN CAAAAANNAG GGGANTGGGG      120

GAAATNTTAG NGGCCANAAG NAAAAAAGAN AATTGTTTNG TTTTGGAGNC CACNNCGNAA      180

NAGGGGGTNT TAAACGCAAN AACACCGGGG GGGGGNTTTT TNTTNCAACG CGAAAAANGC      240

GGAAAAAGAT TTCAGGANAC NTGAATTTTT TNGGGTCGAA GTTCAGTGGG GGGATTGGGG      300

NGNNAAAATT TNANACNGAT TATTGGTCCN ACCTTTCTCC TTCCCNTCCC TNCCAAAATT      360

TTNTCCAATT TTCTTCTTTN TNTCCATTTC CCCACCAGGA GGGAGTCACC CACCTTNTGC      420

NGCAACATTC TCAGGGTTCT TCATTCTCAG TGTAACAGCA GNTCTTCGGG TTCTNGGGNA      480

NTCAGAAACT GGGCTGAATC ATGTCCAGAG TTGCNGAGTT CCCACATAAC AGATAGTGTT      540

NGNGAGATTC TCAGTCTAGA ACCATGTGAG CCAATCCCCA TCAAATCTCT TCTCTCANGN      600

ATAAATNNAA ACATNCTTAN GGGAGGCTCT ATTTCTATGG AGAAACCAGN ACCCATATTT      660

NGGGCTGGAT CACTCTTTAT TTCCATTATG GGATGTTTAA CAGTAATCCT GGTCTGCATT      720

CCNTAGGTGC CAGTAGCCAT CTCCTAGTTG TGACAATCAT CATTTTCTGG GGATGAGGGT      780

GGAGAAGGGG GCAGATATCA AAACTATCCT GNATCTAAGA AATGTTAGTT GAAATGAAGT      840

TGTCATGGGT CATAAAGTCT AGGATAAAGA GTGATGAGAT GTCACTAACC CAACTCTTTT      900

GGCCAGAACT CAATGAGGTN GTCCCATTTG ANTTACCCCA AAGGNGCNTT AGCAAGTAAA      960

AGGGNCG                                                               967
```

(2) INFORMATION FOR SEQ ID NO: 53:

(i) SEQUENCE CHARACTERISTICS:
        (A) LENGTH: 700 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 53:

```
GGNGTGCTGG GATTATAGAT GCACTCCCCC AAATCCAGCT TTTTACCTGA TACCGGAGGA       60
```

```
AGGAACGGAA GTCCNCCGGC TTGCACCGGA AGCAGTTTCA CCCACTGAGC CATCTCCCTG        120

GTCTGTCTGT CTCAGCTTCC TGAGCTGGTG TTATGGCTGT GCACCACCAT AGCTGGCTTC        180

TTTATTATTT ATGTATGACT NGGGTCTNTC TGGGGGTCTG TTAGNCAGTC TGTTAACTAC        240

CATCTTTTGN CTCAGGCAGC TGCAACAGAA AACAACNGGC TGTAAATNGT TTTGACAAAT        300

GGGTCTGGGG AGAAGTCTGT NATGCAGGGA GATCTNGAGT TTATNCAGAG GAAAAGGTGT        360

CTNTCAGNGN ATCTAGGGNA GCATNTCCTN TCNGCGTCTT GGTTTGGGNG AANGANGGAT        420

CAAGAGCCCC NNAGCNNNNN AANTTNCCNT CGAGCAGCCC AGGGATTTTN GCTTTCAACG        480

NANCTNNAGG GAACCCCCNA NCAACCTNGG CNACAATTGG GGNNTTTCCC CCNCCCCCCC        540

CGATTACTTT TNCAAACCNT TGCCACNCCC TCGCNCNATG CCNANCCCCC AAAACGTCGT        600

NNTTCATAAN CNCNNCNCTC NCNCTTNNCC CATGGGGNGC ACACTCCCTT CNCCCNCNTN        660

TNTTAACNGG NGGCGCAAGN CCTTTCTTNC CCCCTNCCCC                              700

(2) INFORMATION FOR SEQ ID NO: 54:

(i) SEQUENCE CHARACTERISTICS:
        (A) LENGTH: 229 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 54:

NCNACGAGAN GTCAANGTGN AANCTGNCGA TGATNAAAAN AACCGANCTT AGGGTGNCAA         60

NGGGTTACCC AGGANGGGGN CAAAGCAAGN TCCAGGCCCA TNANGGACCT GCTGGTNCAT        120

NGCCNGNAAA NACCTACTTA TCCTNGAANA GCCCGAAANG TCCGCTNNGA CCANNTAAGT        180

NCANNNCAAN ANGNACCACN CCNTTAACAC CACCGTATGA NCCCNAANT                    229

(2) INFORMATION FOR SEQ ID NO: 55:

(i) SEQUENCE CHARACTERISTICS:
        (A) LENGTH: 465 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 55:

CCCCTTTCGN NGGCCTCAAT NANTNATTGN CTACCCNANA GTGGCGGTCT NNCATCATGA         60

CAAATAAANC AGCCTTCATG AAATACGATG GCGGGGGGAT TAGAGGNNTT TNTTGAAAGA        120

GCTGAAGGGG CTTGCAACCC CATAAGAACA ACAATGCCAA CCACCCAGAG CTTCNAGGGC        180

ATTAAAACAC TACTGAAAGA CTATACATGG ACTGACCCTG GNCTCCAACT GCATATGTAG        240

CAGAGCAAGA GCCTNGTTGG NGCACCAGTG GAAGGGGAAG CCCTTGNTCC TGCCAAGGTT        300

GGNCTCCCAG NCCAGGGGTA ATNTNGGGGG CGGNGGAGCA GTAAGGGAGG GTGGATGGCG        360

GGGCTACCCA TATNGNGTGG CGGAGGAGAT CGNNGCTNAT GGACAGGAAA CTGGNAAACG        420

GGAATNACAT TGGANATCTC NATAAAGNNN NCATTTCTTA TTCNA                       465

(2) INFORMATION FOR SEQ ID NO: 56:

(i) SEQUENCE CHARACTERISTICS:
        (A) LENGTH: 564 base pairs
        (B) TYPE: nucleic acid
        (C) STRANDEDNESS: double
```

(D) TOPOLOGY: linear (ii) MOLECULE TYPE: DNA (genomic)

(xi) SEQUENCE DESCRIPTION: SEQ ID NO: 56:

```
TTGGGGCCGN TNAACTCTGN GTNNNAGTAT NCCCNANAGG GGGGGTCTCA CANCGGGTCN      60
CACCNCATNT GNGGGNGCCC NTTCNCNACA ACACATTTTG TCNGGNGGTT ATAGNGAGAG     120
CACANATTTT GAGAGTCNCC NGANAGGGGA GAGAGACNCA CACNAGTCTC TTCTCCCCGT     180
GTTCGCGAGN GNACNCTTCT CTNCACATCT ANAGTATANC CCAGNGTCAC ATATGTGGCG     240
GGGGGGTNGT GTCAGNNACA GNGTTTCCCC CNCCNGTNTT TCCCCCTNCC CCCCCCNCAG     300
GGGNAGACAA NGTNNTAGAG AGAACAGGGG TTATCCACAC ATCNCACTGN GNGGCACAGG     360
AGGANNANAN TTGTGCTNAG AGCCCCTGCN CTTCTGGTGG TANCTCTGGG GCCCATATTC     420
TCTNCTCTGG GTCCCCCCCG GGGGGGTGTN NCCCTCNCCG GGAGAGAGTN TTAGAGANAA     480
ATCTCCATCN CANATGANAA AATNTGNGGG NGAGAANCCC GGGGGATATC ACTNTTTTAN     540
AANNGACCCC ACCCCCCCCC CCCT                                            564
```

(2) INFORMATION FOR SEQ ID NO: 57:

(i) SEQUENCE CHARACTERISTICS:
        (A) LENGTH: 822 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 57:

```
GATTTGCNCT CATATNTCNT TTACCAAACA GNGGGNGTCT GCCCCCCTGT NATANACCTC      60
TTGTTNTCGC GGGGTGCTNN TNGGGGCCCC CCNTGTAGAA AAAGAACANN NGNTGTGGGN     120
GGGGGATTTC TCTCTGNTGT AGANCTNTNC NCTGAGACAC ACAGNGCCCT GTGTGGGGTC     180
CCCCTCNCCG AAAAAGANAC CCCNAAAAAA AAAAAAAAAN AGACCGCGNG GGGNNGAAAA     240
ATATCTCTNG NNATCTTCTC TCTAANCTCG CTTTTANTCC TCAGAAAACC CCACCCCNCC     300
NCTCTNCCCA GAAATATNAT ACANNNNGNG TTCCCCTNCC CAAAACCCCA AAGGGNNTCC     360
CCTCTCNTCT NCCCCNAATA CTCTTCCNCC CCTTNATTCT CNTATCTCTN NGGACTCANA     420
CTCTAAAACA CANGNNNCTT NTCTGTGCCG CAATNTNTTN TGTNACANGG CNCCCTGAAA     480
AAAACCCCCG TGTTCTCCAC ATCNCCTCTN TNATATCTCT GCCCCCTTCC NCTATATCNC     540
TGNGTTTATA ATTTCCAAGG AGAATGTNCN CAGGGGGGCC CCAATCTCCC CCCCTNGTTT     600
CNNCGAGNAG GGCTCTTTTN TATATTTTTN NTCNAAACCN CCNTTGTCCT TTTAAATNGG     660
CNTTNACNCC CNGNCCCNCC CAACNNCCCG ANCGGGGGAA ACGTTCCCCA NTTTTCCNTT     720
TCCCCCCGCC CNCCCNNACC CCAATNCCCT TTTTTCGCGT TCCGGGGGCC CTGTTTCCCT     780
AANCCCGGAA TNAANTNCNT TNTTCAANCC CCCCCCTTTT TT                        822
```

(2) INFORMATION FOR SEQ ID NO: 58:

(i) SEQUENCE CHARACTERISTICS:
        (A) LENGTH: 553 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 58:

```
TTTGGGTGCG GTCTCCTCTG TGTTAGTGTA TCCCCCATAG GGGGGGTCTC ACAGGGAGCC      60

CTTCTCTTTT GGGGGGTTAT ACACAGGGGA CACACATGTG ATATAGAGAG AACACATGAG     120

AGTGGGAGAG TGGGGGGGTG GGTGGAAGTG AGAAACAGAG AGAGAGAGAC TTTATTTTTT     180

GTGGTGTAAA ATGTGTTGAA TCTCTGGTTT GATAAATTTT ACACATTGGG GTTTGTGTAG     240

ATCCCTGATC TCTCTCCTAT CCCCATTCTC TTTCAGAGAT GTGTCTCTGG ATTCTCAGAG     300

AGATTTTCTG GTCTCACATG TTTGGTCCCT TATGTTCTCA CTCTCTCTTC TTTATTCTCT     360

GATACATGTG CTCTTCCCCC TTGGGTCTTC TCTCTGTCTC TGTCTCCCCC CCCATGATAC     420

ATAGAGTGTG TTTTCTCCCC GGGGTTTCCC TTGTTCACAA GAAGAGCTCT GGGGAATCTC     480

TATCTTCTCA AGGGTATAGC CCCCCAGTCC CCAGGCCCTT TTTCTTGGAA TTTTGGAGGG     540

GGTTCCCCAT TTT                                                       553
```

(2) INFORMATION FOR SEQ ID NO: 59:

(i) SEQUENCE CHARACTERISTICS:
        (A) LENGTH: 904 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 59:

```
GGGATTTGCT CTCAGATGGT AGTTTACGTA AACTGTGGGT GTCTTGCCTC TCTCTCAAAA      60

CATGTGCGCG TTTCTGGGCC CGTGCGCGTT TTCTGTGCTC CTCCTTCTTC ACTTCTTTGT     120

CGCGGGGGCG CTCGCCCCTG TGTTTTCTGT GCTCCTCGGG GAGATGCTCT CCCTTGGGGC     180

TGTGGGGCTC TGTGGCGGTG GTGGCGGTGT CCTCGATACC GTGCTTTTTT GTTTTCTCGA     240

GATCTTACTT TTTCCTCTCC CCCTTGTGTG TTTCTTGGGT ATACACGAGA TTGTGTGTGT     300

CTCTTTTCTT ACCCCCTCTC TAGTTTATAT TCACACTTAC TCTCTCTCTT TTCTTTTTCT     360

CTTTAGATTC TATCCTTTGT GCACTTTTTC TATTGTGCTC TAGATTTCTC CCCTTTTTGT     420

TTATTTCTCT TCTCCCTGTG TCCAGTGTGG TGAAAAAGAC CCTTATTAAA TTTAGACTTG     480

TGCGCTCTCT TCTTAAATTT CATGTGTTCT ACAGTCTCTC TGCGCTTTAG ATATTTTTAG     540

AAGCGCCTAA ATCTTTTAAA AACGTGTGAG ATCTCTTTTT TTTTTTTACA CTCCTTTGTT     600

TTTTCTTACT CCTCAGGGGC ATATAAACCC CCCTCTCCTT TAATATTTCT CACTCTCTTT     660

CTTTTCAAAA AAATTTTTCA ATCTAAATCC AAATTTTTTT TTTTTTTGG TGGCCCCTAA      720

TTTTTGGGAA CGGCCCCCCC CCCTCCTCTG GGCCCTCATT GGGGGGATTT TTTTAATTCC     780

CGTAAATAAA AAGGGTCGGG CCCTTCTCCC CCCGTGGGGT AATTAATCAA GGATTTTAGG     840

GTTGGTAAAA ATTTCGGGTT TTGATGGTTT TGCCCCCCCC TTAACCCCTC TTTTTTTTTT     900

TTTT                                                                 904
```

(2) INFORMATION FOR SEQ ID NO: 60:

(i) SEQUENCE CHARACTERISTICS:
        (A) LENGTH: 698 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 60:

```
CTCAGCACTG AAAGAGATAG ATTAAAAACA AAACAAAACA ACAACCAAAA AAATACAAAC      60

AAACAAACAA AAAAAAACCC CAAACAAGTC GCTCAACTGT CTTGAGTCAA TAGATTTTAA     120

AAAATGAGTT AAGGTTAGGG TTAGGTTAGG GTTAGGGTAT AGCTCAGGCA GTAAGGTACT     180

TGCCAAGAAT GTTTGAGGAC CTAAGTTTGN CTTTTTTCTT TCTTTCTTNT GAAACAGGGT     240

TTCTCTGTGT AGCCTTTGNT ATAGACCAAG GCTGGCTTCG AACTCAGAGG ATCCACCTGC     300

CTCTGNCTCC GAGTGNCAGA ATTAAAGGCA TGTGCCATCA CTGTCCAGCT CTTAGGTATT     360

CATTTTTCAG CTTATAGTCT TTTGGCAAGG GATGCCAGGG NAGGAACCAG AGGCAGGGTT     420

GAAAAACAGG CCACNGNGGG GGGAACGCTG CTTCCCCGGG TTATTTTCTT GGGTCANATC     480

NTGTGGCCTT CCNGGGGGGT CTTTCCCCTT TCAAAATTNT TTGGGNTTGG GGNGGGGTCC     540

AAATNANTTT TTTNGGCCGG GTTTNGGGGN CCCCCCNNTT TGGNTTTTTT TTTAGAAGGC     600

CCGGNGGGGA NAAACCCCCC GGACTAAAAA AAAAAGGGGG GGANCCCCCC NGGGGNGGAA     660

TTTTTCCCGN CCCTNAAAAG NAAAAATTTT TNTTTTCC                             698
```

(2) INFORMATION FOR SEQ ID NO: 61:

(i) SEQUENCE CHARACTERISTICS:
        (A) LENGTH: 851 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 61:

```
GAAANAANTC GGGAGAAAAA NAAANNNCCN TTAAGAGCTT GCCCCCANAG AAAAANTANN      60

AANTNAAAAA CTGNTAGACC ANNNGAAAAG GAAGCGCAGT NANAAAATGG TTCCTACGGG     120

TTAANTAAGA AGCANGACNG AAAGANNGNN TNNATNTAAC CGGGGNTAGN AAACGGCCCN     180

CTTGTANNAG GACCNAATCG AANTAGTACG ATCATGNTAC ANAGGGAAGG GGACGTTACC     240

CNCGGANGAA ACCCGGCACA AGATCTCNNA AGGGAGAAGA TTCTGAACGN NANNAANCCA     300

CAAGGAAATT ACTGTGGANA CGGGAGGAAT CNATNGTNAT NNAGNNNAGC TGGNCACTTT     360

GANAAGGCAT CGATANAANT GATGATGGNT CAGGCGAAAA AGCATACGTA AAACCAAGCA     420

AGGNGGAATA GTCATANAAC CATGNAAAAA ACNTTCAATA AAAGATNNCC NGAATATTGA     480

TCNGTANNNA ANAACNCCCG GTGGCCGTGA TTCCTTTTTT AACGGCAAAC AGCANNTTAG     540

TTTCAGATCA CCCAGATCAT CGNTGNAGAT NCCATNGATG TTNTTGAAAC TNANCTNGAG     600

GATTCAAGAA NNGNTGACAT GGTGAAATGA TGTACAAATN ACAACANAGA NCGTCGAGAT     660

NNTATTCCCC CNGNATGNAN GGACNTCTTA TGATGAAAC CTTATACCAG ACTCAAGTAN     720

AACNATATGA TCCCATGAGG GNGGNNACCC AGGNAGTCAN GAANAAATAC CNGAGAGTTA     780

AATGCNTTTT TTTGTNTGNG AACCCANTGC CCGACCTNTC AAANAGAAGC ANAGCCCNAA     840

AATTAATCCA A                                                        851
```

(2) INFORMATION FOR SEQ ID NO: 62:

(i) SEQUENCE CHARACTERISTICS:
        (A) LENGTH: 936 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 62:

```
CTAAGGAAAA GGTTTTAGGA GGGAAAACCA ATAGGCCCTT GAGTTCTTAT TCTTAAGACA      60

TTGTAAAGGA AAGGTTTAGG GGAAAAATTA CCAGCCCGAT CCATTAGGGT TCCAAAAGAA     120

CCGTTCTTCC ATAAAGGCCA GAGTTCACCA TGAGTAACCA GGATGTTTCT TCGGACCTTA     180

TAAATATATT TTGAGGGGTT CATGGAATTG GGTTGCCATT TGGTAGTTGG TAGCCTACCC     240

TGCTCCTTCC CAGTGTTGGA TGCAGATATG CGCCCTGTTG GTTTTGAGTA GTTTTGAGAT     300

CAGTCAATTT TAGGTTTTAT GGCAAGCATT TATTCATCCC CACATTTTCT GCCAGGGTGT     360

AGTAAGTGAG TTCTTACAGA GCAGAGAGAA GGAGCAATCT GTGTTATCAA ATCAACTAGC     420

ACCAAGCACA CCAAGCAGCC AATCCTTAGA AGGAAGAAGC AAACACTTGG GTATCCTTCC     480

ATGGCTAGGA AATCTTCATG GCTCACGAAC CTTGGGATTT CCCTGTCAGG GTAGAATACA     540

AGCAGCTGAG ACCGAACAGG TATGGGTGGC ATGTCGAGAC AGGAAAAGAA CCTGTGTCTG     600

GGGAGAGGTG TGTGCTACAA AGCCAGAGAG GGAACAGAT AGGGAGGGGT GTGCTGCACC     660

ATCATGGAGG GGGACAGACG ATTTGTCCCC AAGGAAAAGC TCCCTTTATG AGAGTTCTTA     720

CTGAATTTGG GAATGACATG GGAGACCAAG GGCCAAAGTC CAGATGAGCA GAGTGGGGAG     780

GAGGGTTGGA AAGTTCCAAG GAGAGAGGCG TGGGGGTAAG GGAAGCTCGC AGGGCTCCGC     840

CTCTGCCAGT GACCTTGGAC CGCTTTCTCT GAGGATCAGA GTTATCTGTA GGGGAGATGA     900

GGTTGAAAGA TACCCACAAT AACTTTGGCA AGTAGA                              936

(2) INFORMATION FOR SEQ ID NO: 63:

(i) SEQUENCE CHARACTERISTICS:
         (A) LENGTH: 911 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO: 63:

GGGAATTTAA GGGNGATTTG GAGACTTTNG AATTTTCGAA NGTTCCAAAA TAGANNTTNA      60

GGNCAATGGG NTTGGGGCAG NGGNGCTTTT TTAAATCANA NAAGTATTAG ATTTNTATGG     120

AAACCCTGGG GGTTCCAGTT TAATCCCTTC ATCATCTTGA AATATNACTT GTTTATGGGA     180

ANGGTGNGAT AGCAGCCNGA AACAGAGGTT TTTATTATTA CTGTTAGAGA NGAGGATTGG     240

GGAATAGAAC AATGAGAGTC TTGGTAATAT TNTTCNGGAA ACAACNGACA TAATTGGAAC     300

ATTAAGGAAA TATATCCATG CATTCTGTAC TTGCAAATTG CTCCAAGGAA GATGGAGAGT     360

ATTGTATTTC AGATAGAGAT ANGACTATAC CTGTTATTTT TTTCATTATA GCAACATTAA     420

AAAAGATAGT AATCTAATTT CACATAACCA TTACTACTAA AGTATATATG TANTCTTTGT     480

TTATCAGGTT TTACTTCTCA GAAATTGCAG CATCTCCTAC AGAGCCTGTC AAATGAGACN     540

GCATAGATCC CCAGAGAACA GAGAGACTGG GAAATCATTG AAATTACACA ATCCTATCCC     600

AAATGTTTGC GTAGACTCAA GCTCGTATCA GCTCATAAGA TCAGTGTGTG TGTGTGTTTG     660

TGTGTGTGTG TGTCCCGCAC ATGCTTGAGT ATGCATGTGT GCATGCATGT GTGTATGTCT     720

ATTGCATTAG TAGAGATGTT AAGGTTGAAT GTATTTTCTG CTCATGGTCA TTGTAAGATA     780

TTGTGCTGTA TGTGATAAGA ATCAATGTAA CAAGGCTGGA GAGATGACTT CAGCTGTTAA     840

AGGCTAGACT CACTACCAAA AATAGNGCNA TCAGTGTGAA NTTCCCCACA GGAGCTTAGC     900

AAGNTAATAG G                                                         911
```

(2) INFORMATION FOR SEQ ID NO: 64:

(i) SEQUENCE CHARACTERISTICS:
        (A) LENGTH: 781 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 64:

```
TTCAGGGGTA ATCCTAAGGT AAACGGACAA AGTAAAGGGG AGGTTGGACC AATAAAGGGG      60

AAAAATAAAA GATTAACCGG ATGTTCCCTG GAACGACAAA TTGCCTTGGA AGTTTCCTAT     120

ACGGAAAAAA ATGAACAAGT TTCCTGTAAA GCAGGTAGCC GGAACGTTTC TAGGCTATAA     180

ATTTAACTGG CCTTATATTT ACAAAGTCTA AACATTTTAC TGGGGCATTA CAATTTTATA     240

ACACTAATTA GATCATGTGT GTACACCCAC AGTCTGACAG ACAGGGTATT TTTTCCTTCT     300

TATCCCAAGT GAGTTTAACC TTCCTTCTCC ACATTTATTG CCATGTGCAA TGCGTAGCTT     360

CTATTAACTC CTGATTATTG ATTGAACTTT ATGAGACATA AGAATGTACT TGACAACAGC     420

ATGTGAGAAA GGGAAAGTTG AGGGACTGAG TGTAATAGAG ACTGATAAGA AATGAATGGG     480

CTGTGTCTGA CTCTTATCCA ACATTCCAAT TCTTCAAGTC TAAAGGTGAA GGGTCATTTT     540

CAATCTACTA AGTTTGAATA TGATTTGTGC TCCTGGTGTC TACAGAGTAT TAGGAAATGT     600

TTGGTTTGTT AGGTCATTAG GGTAGGGCTC TTATGATAGA ATTCTTGTGG CTTTACATGG     660

AAAGGCAGAG AGAATACACC CACCCTAAAC ATTTCTGCCA TTGTGCAATA CAGTAAGGTA     720

TATTTCTTTC TTTTTATTAA CTATTTGGTG ATAGTGACAA ACAACTAGAC TTCATATGTG     780

A                                                                    781
```

(2) INFORMATION FOR SEQ ID NO: 65:

(i) SEQUENCE CHARACTERISTICS:
        (A) LENGTH: 389 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 65:

```
TTGCTCTTAG GAGTTTCCTA ATACATCCCA AACTCAAATA TATAAAGCAT TTGACTTGTT      60

CTATGCCCTA GGGGCGGGG GGAAGCTAAG CCAGCTTTTT TTAACATTTA AAATGTTAAT     120

TCCATTTTAA ATGCACAGAT GTTTTTATTT CATAAGGGTT TCAATGTGCA TGAATGCTGC     180

AATATTCCTG TTACCAAAGC TAGTATAAAT AAAAATAGAT AAACGTGGAA ATTACTTAGA     240

GTTTCTGTCA TTAACGTTTC CTTCCTCAGT TGACAACATA AATGCGCTGC TGAGAAGCCA     300

GTTTGCATCT GTCAGGATCA ATTTCCCATT ATGCCAGTCA TATTAATTAC TAGTCAATTA     360

GTTGATTTTT ATTTTTGACA TATACATGT                                      389
```

(2) INFORMATION FOR SEQ ID NO: 66:

(i) SEQUENCE CHARACTERISTICS:
        (A) LENGTH: 340 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 66:

```
AAATCGGGNT TNCGCGATTC GGTAATGACG NCNNATCCGT AAANNCATNC GCCGNNATNC      60

NATTNGAAAA TNCCGGGNGC AANNCGATGT CTNATTGAGG TNNCAGANCC ATCCGGCACA     120

GGCAATANGN AAAAAANGGG AGTTTCACAA TGTNTNTGAA TNTGNANCCA TTGGGCCCNA     180

AAAANTCCTN CGNTNNATGA ACCTTNNCGT NCAAAANTTT GGTNCGACNC AGCNGCTTTG     240

CNAGCNTTNA ATAAACACCG GNNTCCANAA TGNNACCAGN GNTGTTTNTN TCNANTNGCA     300

TNNCNNTTTG GAANCCCNCT TTTCCCAAAA CNTTNAAAAA                           340
```

(2) INFORMATION FOR SEQ ID NO: 67:

(i) SEQUENCE CHARACTERISTICS:
        (A) LENGTH: 557 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 67:

```
AGTCCGGGNA TGGTGGCANA TGCTTTTCAT NCCAGCACTT GGGAAGGCAA AAAACAGTTA      60

NACCTNAGGT TTANCCCAGN CTTTATTAGN ACCCCGTGTT CTNAAACACA AACNACAAAA     120

NTTTGNGGGN NTTTAAGTGN AAACACTGTG TAAAACCTTG GCCCTGATGN AGGGNTCTCC     180

TTTNGAACAG AAAATGTTTG AAGANTCCNA AAACATGTTG GGATGCCANA CGNGTTNTTG     240

NGCATCCATC TCAACGANGT TTTGNGAATA AATGGCAGGT NAAACTAGTA CATCATCATG     300

TNGNANCCAC CGGGCNTGCA GATTTGTGGT GGGAACCAAG TCCTCCCATA AAACAGGCTC     360

CTGTGGTACN AACAGGGCTG GANCCACNGA ATCAGTGCAG NTCTGGACAC CTGTCTGGCC     420

GGANGGNCTG GNCTAAGTNA ANNCAGGGGG GGCAAGAGCA TNGGANCNAA CGNCAGAAAN     480

CGNCCCNCCC GGTGAGCTNT TCCATGCCTN NCCTCGNTTT ATTTGGCACT GGGCATGTCC     540

CAACTNAACT TAGGATG                                                    557
```

(2) INFORMATION FOR SEQ ID NO: 68:

(i) SEQUENCE CHARACTERISTICS:
        (A) LENGTH: 302 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 68:

```
GCCTATAAGT TTTGATTCCA TTCGTGAAAA TTTTTCCTAT ATCCCGAANA GTCCACTTAT      60

TACTACTGCG GCCTATTTGG AAACTAACCG AAATTCAGTT AGTTCCCTAG TAGCCTGCTC     120

TTGTAATATG TGTACTTTTC AATATTATAA AAAATTGGTC AGCAGATCTG AGTAAAACAG     180

GTGAAATTCC GATCGGTAGT CCAATTTGGT TAAAGAACAG GATATCCAGT GGTCCAAGGC     240

TCCAGTTTTG AACTCAAACA ATTATCAACC AGCTGNAAGC CCTATAGNAG TACGNAGCCC     300

AT                                                                    302
```

(2) INFORMATION FOR SEQ ID NO: 69:

(i) SEQUENCE CHARACTERISTICS:
        (A) LENGTH: 820 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 69:

```
GACTGCCTTT TTTTTCTTCC CAAGGATACC CTGCAGCACC CAACAGTAAA AGACTTCATA    60

AATAGGCAGC TTGGAGAAGA AGGCATTACC ACTGAAGCCA TATTAAATTT CTTCCCTAAC   120

GGTCCCCGAG AGAACCAAGC TGATGACATG ACCAGCTTTG ACTGGAGGGA TATATTCAAC   180

ATCACTGACC GCTTCTGCGC CTGGCTAATC AATACCTGGA GGTAAGAGGC AGCAATCCAC   240

CCGAGGACCA TAGTGAACCT CTTAATGTCA TGGGTGAGGC TAGAGACCTG TTAGCCAGTC   300

AGCTGGCACT GGATTCAGTC TTTCATCCTT CGCACAAAGT GGTAAGGGTG CCATGGCCAT   360

CTGACAGACT TGCGTGCGAC TGTCCTCACA TCTCGATAAC TTCATGACTC CTCTGGCTCC   420

CCCTCTTTCC CTTCCAGCAC ACATCCATTC CCAGCTATCT CCGGGCTGCC ATTGTCTAAT   480

GACTTCTGTT GGCCGGTGTC CGCCAAACCT TTGAGTTGAG CTCATTGATT GTGGACACTT   540

TACTCAAAGT TTAACAGCAT GTGAAAGACC CCGCTGACGG GTAGNAATCA CTCAGAGGAN   600

CCTCCAAGGA ACAGCGGGCC ACAAGNGGTN AACTNAAANG GGTTATTGNT AACGGGNNCC   660

GGGANCNAGT AATCGGGNCT GGCCCCAANT AAGGGTTTGG GCTTTATTNN CNGGGACAAA   720

AACCGCAAAA AAANNAAACG CCTTNTTGTA TTAAAANGCA NGNTTTTAGC CTTGGCCTGA   780

AATGGNGNTA AGNTACGGCC CNCNGTCAAT TCCTACTATA                         820
```

(2) INFORMATION FOR SEQ ID NO: 70:

(i) SEQUENCE CHARACTERISTICS:
    (A) LENGTH: 955 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO: 70:

```
AANCCGANAN TTTNAAAAAA CAANNANAAN GGGCCANGAN NTNAATANTT TCTNAAAAAA    60

NGANTACANG NACACGGCAG GGNNGTTTAG TCAGAATANA ATNNAGNGNN AACCATTGNC   120

TTTTGAGCAG GGTTTATNGG NCTACGTTGA CCCAAGTCAC ANTGNTANCA GAGATNANNG   180

AGGGGGNGGG AAGGGGTTNG GNTTTCCACA GCNTTNAAGT CAGAANTNGG AGAGACATTT   240

NGCCNTGATT CANGNCTTTN CCTCCTTATT TCCNANCNTC NCATTAANAN NAGAAAAGAG   300

TNTTTTNTTG TNTTGNGNAC AGGTGCACAA GTTTAGNANA GAGGAGACAN TGTNTAGAGA   360

TCAGATACGA ATGAGAGTTT CCGGGGANAG TATGNGGGGA TTTTCAGTCA GNNCACTACC   420

CAGAANGGAT TCAGTCGNGA GGAGNCAGGG ANGGGGTGNT GGAGTTNAGA CCGANAGAGC   480

GGNTAGCATN TAATGNNNAG AGAACACACA TNTTTTGGAT TTNAGAGACG NCCAAANCGC   540

TATACANGAT NTNTCGNTAN AGGGTGAAGA GTGAAGAAAG TGATGTCTCC ANCGCANACN   600

GGAACANGCN GCGANTTTCT TAGAGACCNA GGTTTTGATA NAGGGAAAGT CTATTCAAGC   660

CTCCCGTANA CTTGTAGGNC AAGNAAATAN TGCNNATTAT GAGNCCGTTG TTNTCAAACC   720

ANGTCCCCTA TAGCAGCAAA NAGTTGNCAG AAANTCNCAC AGAGNTCCCC CGTGAGATNG   780

NNNTTATNGN GGACACGATG TCATCAAGAG GGAGTNNTGN ACTGTGACTC CAGTCCTGTT   840

GAAGNGCATA GTAGACCATT CGCCGTGTTC ACCNACANTC AGCCNCTACC AGCNGAAAGA   900

GNAAAGGAGA GAGTTCGCAT ATGANAGACC CCACGGGTAG TTTGCAAGTA ATGAG        955
```

(2) INFORMATION FOR SEQ ID NO: 71:

(i) SEQUENCE CHARACTERISTICS:
        (A) LENGTH: 886 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 71:

```
NTNGAAGNAN AAAATTNGNAA AAANNCCNAA AACCTCCAAA TTTGCTACCA NTCTTCNACG    60
GTNGACTTTT AAACAAAAGG AGGGGGGGGT TCTTNTTCAA ATGGGCCCCT TCCCAATCCT   120
GTTCCCNAGG CAATTGTTTC TTNTTTCANC NTTCAACGGT TTTTGGGTTC CATCCAACTT   180
TTATTTNACC CNTTGAGTTT CCTGGCCGGN GCCTAGGGAC CTCCTTTTTA CNTGGGCCAG   240
TTCCCGTTCA AGACNACCCG GCGGTTAGTG GNCATGGGGA GATGGCCCCA TGANTCCAAG   300
ACAACTGTAT TCCCGGTTTT TTAGTATTTC CAAGCTTCCC GCCAATTTTT CTTCCTTCCG   360
CTTCCAGACA GTTTTGCCAG TNACGTGATT CGGTTCCGAG GCCCCAGCAC CATGGAGANT   420
GCGCGCTGTA NTCTTAGAAG GGCATTCTTC CGCCCCACNT CCCGGTNTAG CCNGAAGGCC   480
CACGGAGCAA CGAGGAGAGC GACGNTNTCT CCACAGCCGT GGCTTTTTTA TGGTTGGCAC   540
TTAAGGNTTC GCCGCCATTT TGTCCGTTCN TNGAGTTATT GTGTTGAGGG CAAGATCTTA   600
CGATTGGGTT TTGAAGGCAT GGGTAGTGGC TTGTAGACGC ATGGCAGGAG TTGGGATTCG   660
TTTGGGGACA CTGAGGGGAA GCCGNTTCTT GGGGTGTGTC CCCTNGACGC TGTTGTGGGT   720
GGGGACCGGA ACTAGACGTG CCGGGCTGCG GCGCCCAGCG TGGGAGGACT CGCGCGGGCT   780
GGCAGCCGGG CTGGGTGTCC CGGCGCCTCA CTCACATTTT TTGCCACGAT TGTCGCCTGG   840
TTTGATTTCC CACCAATCCC CCAGACCGTG CACGAGGAGT AGAAGC              886
```

(2) INFORMATION FOR SEQ ID NO: 72:

(i) SEQUENCE CHARACTERISTICS:
        (A) LENGTH: 900 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 72:

```
GGGNGTTNGC TCTCAGATGC NAGNTACNNN TCAGGGGGNG TCTCACGAGA AAANCTNATG    60
TGTGGGGGNT ANTNTGTATC CCCTNNNCTC NCTCGAGANC CCNNNTCTCG ANATTTTGGN   120
GACCNGGGGC CGGGGCCCAG ANACTCNCCA CCCCATATGG NGACCCTNTA TAAGTGTCNN   180
CCAGGGNNTG TTTTGGGNAA AATATANCNN ANAGNGGTGT NTNTNANATC TCGGGGGGTG   240
ACAGACCCNN ATTTTTTTTT ATAAAGACCC GGGGCATNTT CTCNGCCCCN TCTCCTCNGC   300
TACANGNNAC CCACACACAG TGTGTCTCCT CTCAGCCCCC TGGCACACTT TNTNTNGANT   360
CNGNGGGGAT ATGAGATTCN CNAGACTGGG NCCGCNNTAN TANNCNCCCC CNTGTCTCCT   420
CTCATAGTGT NGTGTCCCCC CCTCACCCNN TNTTGNGGTN CCCTACACCC ACACAATNTA   480
GACTCTNCCC NCCNTCNGCT NTGNGACNCA CANCTGNAAA TCCCGNNNCN CAAAAAGGGC   540
TGTNCTCCTC TCTNTTACNG GGNGGTCNCC CNCNNNNGAC TCTNAAANGT CCCTCNCAAA   600
AGGGACNCTT TTCTATACAC NCTTANTTTN CCTCCTTTGT NTNGCAAAAA ANNANCCTGT   660
GTTNCCCCCC NCTTTATNAT NTTTNTTTTN TTCCCCAAAC TAANCTTTTA GGNNTNANCT   720
```

```
TCCGGGGCCC CAACCCCAAA ATCCCANTNT TCTTTTNTNT TGGTTGGGGT GTCAAAATTC      780

CTNCCCCTAA ANTTTTGAAC CCCCTTTAAT TCCCCCCCCC GGNTNAAGGC CCNACTTCCC      840

TNGGNTNTTT TCNCTAAAAA ATTTTTTGTN GCCCTCCCTG GGAAATCCCC GGTATTCCTC      900
```

(2) INFORMATION FOR SEQ ID NO: 73:

(i) SEQUENCE CHARACTERISTICS:
        (A) LENGTH: 1033 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 73:

```
CCTACGTTCA CCTATGCGTA ACAGATCTGC TGTGTCAGGA GCCTCCTACC CTCGCGCATC       60

CTGACCCCCA ACCACGTCCT CTTATCTGAT GACTGGTCAT CTTCCCAAGT CATACACCTC      120

ACCAGATCAC TCGTGGGGAT CTCTAGGCCA CCTCCTGTGG TACCCTAGGC CTTGGATCAC      180

TACTAACTCC TGCATCGTGG TAACCTCAAT GGCTGATCTT GAGGATGCAG TCTGGAGTTC      240

GACTCCATCA GGAAGCCACA TGGGGAGGTG GCTGAATGCC ACAGGCACCT ACCACATAAT      300

GCTTCATGTC CCCACAATAG TGTCATCAAG CANCGNTATC TCCCTTTGTA CCTGNCTATC      360

ACAGTAGGCC CTATGTGTTG AAGACAGAAA CGTTCTNATA CTCAAAATAG CTACCTACTT      420

TCATCTTTAG NAAAGTTATC ACCAGAGATT TCATCACATG NCTNGGCTTA NGTATTTTAT      480

CCCCTTTCTG AACTATTTAT CACGGGCAGA AAATNTACTG ATTATCCCTG TATCATGACA      540

TCGTGCTGNA GAGAAGACCC GAGTGGGCAG CATGGNGATC CAAGGAGACA AGGGAAACCA      600

AGCAGCTATA CATAGGATGT CAGCAGCAAG CCCTTCCCTG CCCACGTCAG ACTAAACCCT      660

TCAGTCCCTT CATCTTTTCC TAGAAGGGTT TGTAATTTCT GTTGATTGTG CACCAGCGCT      720

TCCCAATCGC TGAACATCTT TCTTCGAATG TGACTCAAAG TGAGTGCACC GAGTCTGGCT      780

AATGTCCTCT GCTCCTCTTA ACCTCTGTGG CACACTCCTC CTAACACATG TGTGTCGTCT      840

TGTTCCACAG TGGCCCCACG GTACTGGTTT CAATATAGCT TATGTATGAG CAATAAGGGC      900

TATGTATTTT TTTTTTTCAG ACACTGTTCC TTTTGTATTC AACAACCTCC TCACATACTC      960

AGCCGNACCA CATTTCTTCC AGGTCAAAAA CCATCTCTCC AATTTGTTAT GAATTACTCC     1020

TNCAAGTTCA GGT                                                      1033
```

(2) INFORMATION FOR SEQ ID NO: 74:

(i) SEQUENCE CHARACTERISTICS:
        (A) LENGTH: 883 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 74:

```
GGGGGGNNAA NAATTTCCCA AAAANNGNNG GNCCCNTTTT TTATCCAGTT TNNGGTTGAA       60

NATCTCNCCC CGGTTTNAAA ACCCNCAATG GGGAAAAAGG TACANCNGAT TNTTTATNGG      120

TTTGGGCGGA GGGGGAAATT TTTTTGGTTT TTTTNTTTNN GGGATTTTTG AAAAAAAAAN      180

GAANTTTTTA GGTTTCCCNN ANGTAATTTA TTTCAATGGA CCATTTTTGG GGTTCTCCCT      240

TTTGTAANAN GTTAAAAANA AGGGANTTCC AANNTTNCTT TTCAGTTTCC AGTTTCACCT      300

TCNGTAGCAG ACCCAGTTTT CATTTTGAGN TGGTNCCNAA AAGGNTTCCC AACTATGTTC      360
```

```
AATACCACAG GCAGCCTGCA GGAGGGAGAA TGGGTATGTA TTTAACAGCA TTTGACCAAA      420

TTATAAGAGC AGAGAGGAGC TTTACCAGGG ACAGGAAGGC AAAAGAGCTG AATNTTAAAC      480

AAAAGAATAA GAACAGGATN TCATCTGTGA GCTGTCACAG TGGGTTTGCA GAGCAGGAGA      540

ACACAGACAG GATTAGCTAT AAAGTTGTTA CATTAGTTAT TNTATTGGAG CATACAATAC      600

TTAAATAGTT CTAGGGCAAG AGAAATGAAC AGAAATGACC TTATAAGAGC CAGAGCTGTA      660

GCCACAGCTT TCTTTGTGCT TAGTTTGNTA GTTCANTCTT TCCAGGGCAG TCTGGTGGAT      720

NACACCAAAT TGCTTTAGAA AATGCTAGNT CTACTGTCCC TGTCTATTGT CAGCTTTGCA      780

ATGTGCATAG TGACAGGAGT TGCCTGGGAG CTTGGGGCTT ATGTTTTGCA GATCCATTGT      840

AATTAAAAAA GAATTGTAAG GAGATGGAGG CACGGGGTGA GGG                       883

(2) INFORMATION FOR SEQ ID NO: 75:

(i) SEQUENCE CHARACTERISTICS:
        (A) LENGTH: 892 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 75:

GGGCCCCCCT CGAGGTCGAC GGTATCGATA AGCTTGATAT CGAATTCAGC TCTTAGCAAT       60

CTGACACCCT CTTCTGGCCT CTTCAGGCAC CTGCATGGTT CCACAGGACT GTCACACCCA      120

CGTACATAGA TAGTCAAAAT CTAGAGCACT GTTTCTATAC CTGTGAGTTG CAACCCCTTT      180

GGGAGTGCGG TCAAATGACC CTATCACAGG GGTCTCAAAT GAGATATCCT GCATATCAAA      240

TATTTACATT ATGATTCATA GTAGTACCAG AATTACAGTT ATGAAGTTAC AAAATAATTT      300

TATAGCTGAG AGTCACCACA ACATGCATAA CTGTATTAAA ATGTTACAGC ATTAGCAAGG      360

TTGAGAAATA CTGGTCTAGA GCCATTCCTT GTGCTGATAA AGGTGGCAGT GAGCATTATC      420

TTTCTGTCTC CACACCACTA GCAAATTTTT TCTCTATATA TAAACATGTA ATATGAGACA      480

GTCTGAATCC ACTGAGGCAC GGTCTGACTC CAGAACAAAG GATCGTATTC CTGAAAAGCA      540

AAACGTGTGT TTGGCACTGA CTGTGTGNCC CAGGTTNTCT TTCTGNACTC CTAGAGGTCT      600

GTANTGGGTC TTGAAGCACA GATNCTCTAA CCTTACCCTG GNNGCTCAGT AGNATGCCCC      660

AAAACNCANG NTGTTCAACA TNGGGNNCCN CCCNGAAACA GNGNTGTNGG ATTTGGNAGA      720

AAGGTGNAAT NCTTTGGGCN NNTCGGTTTA GGAATTTTAA ACANNAACTG GCTTNCNAGG      780

TCCNTTCCGG AGTCATCCTT NCACTGGNGC CCNCTGGACC CGGNGNANNG GGCCANTTCG      840

CCAGTTCGTN CCCCTGGNAC CCNTCNCCGG GGGCNAAANG CCCCTNNNNT TC             892

(2) INFORMATION FOR SEQ ID NO: 76:

(i) SEQUENCE CHARACTERISTICS:
        (A) LENGTH: 884 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 76:

TGGGCCCCCC TCGAGGTCGA CGGTATCGAT AAGCTTGAGG GACCCACGTG ATGGAAAGGG       60

AGAAGCAATT TAGTGTCCTT TGTCCTCTGA CCTCCACAAG TGCTGTGGCA TGGGGACACA      120
```

```
GGACTGTACA CACACACACA CACACACACA CACACACACA CACACACGCA CGCACACACA      180

CCCCTCAAGT AACCGTGGAA TAAAGGTCCG ACCAGAAACC ACGCTGGAAC GGGAGATGCT      240

GGAGCACATC AGGGTGGTGC TAAGCAGCAG ATCGGCCTGT AACTGGCAGC AGAGGGGTGT      300

GGCTCTTTCA GAACCAGGAG GGCATCGCCC CTCCAGCCAG ACTCTCCAGC TTTCTTCCCC      360

TCCTTGCCTC CTGTTTTCCT TCTGCCTACC TTCCTTTGGC CTCAAACCAT AATGTGCAAC      420

ACATTCAAAC TGTAGTAAGT GTTTTAATTT TCTACTAAAC AATAAAACCT TTAGATTTTC      480

ACTGGGCCAG TGCTGGTAAC AGCAGACTGG GTGGAGTATC ACAGAGGGTG TGGAGCAAGC      540

TGGCTACCCA GGGCTGGGCA CACTCAACAC TCTGGCATTC TGTGGAAGTT CTGGGCAGTA      600

AAAACAGAAG CATACGTCAC GCACAGGTTC CATAGTGTTA GGCATCTTAA TCTATCTAGA      660

ATACCTGGTG TTTAGTTTGT TTACAAAATT GATTGTTGTA CTTGGACAGT GGTGTTTTTT      720

TCCCAGGGCT TCCAGGATTT AGGGGTATAC CAGGCCCATT ACATTGGGTA AACGTGTGTG      780

TTAATTTTTT CTTTTTAAAC CTCCTTGGTT GACTACTTGT TTTCCTTTTT AATGGTCCCA      840

GTTCCCCTTG GGGGTTTGT TTTGGAAAAA GGCTTTCCGG TTTC                       884

(2) INFORMATION FOR SEQ ID NO: 77:

(i) SEQUENCE CHARACTERISTICS:
        (A) LENGTH: 326 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 77:

AGCACACCAC AGAGAGGGGG TCTCCGTGCC CGAGAGGCAA AAGTCTCCCA CTGTGCTCCT       60

CTCCCCCCCT GGTGGGGGTT AAGAGATGGG GGCTCTGGGG GGTGATAGAA CCCCTGGCGG      120

GACACCCCCC CGCTCTCGTG GAGAGAGACA GAGGGGGGTG CCCCTGATAT CTCACTAGAG      180

GGGAGAGGTG AGAGGGCTCC ACAGTGTGGT GTGGTGGTGA GTGCTCTATC TCCAGGTGTC      240

TCACATATTT TCACAGCTCT TGACCACAGA GAGATCTTGT TGACTCTGTG CTCGCGGAAT      300

CTAATGTGCC CCACATCATA TACACA                                          326

(2) INFORMATION FOR SEQ ID NO: 78:

(i) SEQUENCE CHARACTERISTICS:
        (A) LENGTH: 557 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 78:

GGGGGGGTCT CACNNTANAN CACTCNGGNG TCTCCCATGT CTAGATCTCC CCCCNGCNCN       60

NGNGANGAGT GTGNGGAGAT CCCTCTCTGN TCTCTACACT CTAAAGGGTA NGCGGGGAGA      120

GAGAGAGAGC ACANTCTATA GANCACANAG CACACNCGCT CNANGTGCCC NANTNACANG      180

NNAGAGAGAN CCCCTCTCNC AGTATATNGG GGAGAGAGTN TGAGGGACNC TCCTCTTTTC      240

TCTCAACNCT GNGGGGGGAG NGNGAGTGTT CTCTCTGNGG GGNGGAGNGG NACACTCNGN      300

TCTNCGTNTG NGTGCNCNNG TNTTCTGGGG GTCACANAGA AATCNCCTNT CTCAACACAA      360

CAACAACAAC CCCCCGCACG NGCACACACC ACAACAACAA NGGGACANCG CGNGGGGGNT      420

NGNGCACACC CAGNGGAGAC ACTGTTTTCT GTTTNACACA CACACACACA CACACACACA      480
```

```
CNCNCCCCCC ACANAGTTTT TNGGAAAANC GCNGGGGGGG GNGGGNCTTT TTGCCNCAAG        540

CCTTTTTTNA NCNCCCA                                                      557

(2) INFORMATION FOR SEQ ID NO: 79:

(i) SEQUENCE CHARACTERISTICS:
        (A) LENGTH: 376 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 79:

GTCTCCCCCA AGGGGGGGT CTCACCCTCC CGGACACCAC ACATCTGTCT GTCTCTCTGA         60

TCTCTGACAC CCCACAGAGA TATATATAGG GACAACGCCG CTGTCCCCAT GATATAGAGA       120

GAAGCGAGAC AAACTCTCAG GTACACATGA CACATGATCC CCATGATCCC CGGCACACTC       180

TTCTAATATA GTTGAGAGAG TTGTGTCTCT CAAGTGTCTC TGGTATTTTC TAACCCCATG       240

TTTTCTCTCA CAATGTCACA CGGGGGAGCT CGGACGCGGT GCACATGGGG GAGAGTTCGT       300

GTCTATGACA CACTAGTCTT GCCCCCGAAC CACAGAGACC TCGACTCGGG TTTAGTCTCC       360

TCTGCCCCCC CAGCTC                                                      376

(2) INFORMATION FOR SEQ ID NO: 80:

(i) SEQUENCE CHARACTERISTICS:
        (A) LENGTH: 533 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 80:

ATNNCCCAAN ATCANATGNG GAANNNCCCA CATTTTNTAT NTAGAAAANGN GTTTTGTGTG        60

TGTGNGTNNA ATTTGAGNTT TCACAGAGNT NACATTCTCT GTGTCACAAN CCCTTTCTCT       120

CTACACTCCA CAGTGTGGTG NGAGATATAC TNTGANACAN ATGNGCTCTC TCCTCNCCCC       180

CCNNCATGTT NTNCCCCACA GTNTACNNCN NCNATATATN GNNCNCNGNA GANNGGTATG       240

NGNGNTGTNT TTNTTTAAAA AGATNTNANA NAGNGGGTAT GCGTGNGGGG TATGTNNANA       300

CATATATGTN NNAGAGGGTC TCTCTGNGGC CCNATGGAGG CANATCCCCC CCNCTCNGAG       360

NNATATAGAA AAGAGTNTTT NANGGTGTTT GTGGACACAG ATAAGGGGAG AGAGAGAGAG       420

AGAGANAGAG AGAGANAGAG AGAGAGAGAG AGAGAGANAN GGNGTNTTNG GNTTCNTCCC       480

CCCCNATATA CAGAAAAANC GGGGGGGGGT TAGGNGGNNG GGGGTTTNCT TTA              533

(2) INFORMATION FOR SEQ ID NO: 81:

(i) SEQUENCE CHARACTERISTICS:
        (A) LENGTH: 346 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 81:

TTTCACACGA GATGTCGCGA CTCTCGCGAG ACTCTCAGCG CGGAGATATA GACCCACAAG        60

GGGAATCCCC CGGGTTTTTT GCCACAGGAG AGCGCGAGGA GAGAGATATT CTTATTATGG       120
```

```
CTATAGACAC CCCCGTGGGT GGGGGACATT TGTGGTGTTT CCACAGGGGG GGGGATGTAC      180

CCCGGATATC AGAGTATTCT CTAAAAAAGG TGAGAAGAGG TCTTCTCTTT TGAGAGTATG      240

GGGACACTCG AGGAGAGCTC TCTATCTATC TCTCACAGCG CCCCTGTGTG GGCGGATCCT      300

CCACACCAGA TGTTAGTGTG NAGATCTCCC CATCTTCTAT ATTGAA                     346

(2) INFORMATION FOR SEQ ID NO: 82:

(i) SEQUENCE CHARACTERISTICS:
        (A) LENGTH: 461 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 82:

GAANACCCAA AATTGNGCTN GTGGGCAAAN NTTTTNCCGT TTCTTGTGCT TGNGCGGCNA       60

AGNNAAAAAT TCAAAACCAA NACCACANAA GCGCGTTATC CTGNCTNTCT GCCNTTNCCC      120

TGTCACACTG NGGCTGTACA GACATCNANC GCTTTCTAGA GAGACGNGAG AGTCAGGGGA      180

CTCTTTCCCC CANNCGCATT ATANCCACAT ATTAGNGTAN NANATTCAGC TGTGNTNCAC      240

TGGGNGTGTC TCCNTAGTGT GAAGCAACAC AGGGAAACTN TTCGCNCACA TGTCCTCTGG      300

TGTTCACAGA NATAAGNAGG CTCCTAGACC NNTATNACTG TGGGNAGAGN ATGTTACCTC      360

CCTATANNTC GGGGTCTATC TCTGTGAGAN AGAGNTTCCT TTCTCCCATN CCTACCTCAG      420

TGGGGTGNTA TNTACATCNC AGAGAGCAGA NAACTGTGAG C                         461

(2) INFORMATION FOR SEQ ID NO: 83:

(i) SEQUENCE CHARACTERISTICS:
        (A) LENGTH: 367 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 83:

GGGGTNTCAC AGAGANAGGG CACANCTCTC CCNAGAANGG GNCNNCCCTC TTTTTNNGGN       60

GTAACACCTC TCNCCGTGTC TCTTTCTTTC TTTTTTNTTT TTTGGGGGGC TCTTTTTCGN      120

GGAGGNGGAG NNCGNCCGAG GGTCGGGCNN NNCNGNGGAN AGCTCTNTCN CANNGATATA      180

TCNCCNNANC CCCCCTGTNT CTTATAANNN ACATCTCTTC NTCNCAGGGT CACACCNAGA      240

NTCTCNTTTC TACAACAACC CCCACACGCN AAAGCTCCCC ACNNNGNGNG GGGGTCTCNC      300

AAGAANATCT CNGCGGAGAG GTGGNGGAGA GAGTGANATC TGNATNTCTG GNTTCCCCNC      360

ANTGCCC                                                                367
```